(12) United States Patent
Schmalz et al.

(10) Patent No.: US 8,927,750 B2
(45) Date of Patent: Jan. 6, 2015

(54) ACYLOXY- AND PHOSPHORYLOXY-BUTADIENE-FE(CO)₃ COMPLEXES AS ENZYME-TRIGGERED CO-RELEASING MOLECULES

(75) Inventors: Hans-Guenther Schmalz, Bruehl (DE); Steffen Romanski, Cologne (DE); Sabine Amslinger, Regensburg (DE); Benito Yard, Dackenheim (DE); Birgit Kraus, Siegenburg (DE)

(73) Assignees: Universitaet Zu Koeln, Cologne (DE); Universitaet Regensburg, Regensburg (DE)

( * ) Notice: Subject to any disclaimer, the term of this patent is extended or adjusted under 35 U.S.C. 154(b) by 611 days.

(21) Appl. No.: 13/020,933

(22) Filed: Feb. 4, 2011

(65) Prior Publication Data

US 2012/0202774 A1     Aug. 9, 2012

(51) Int. Cl.
    *C07F 15/02*        (2006.01)
    *C07F 7/08*         (2006.01)
    *C07F 17/02*        (2006.01)
    *C07F 7/18*         (2006.01)

(52) U.S. Cl.
    CPC .............. *C07F 7/0809* (2013.01); *C07F 17/02* (2013.01); *C07F 7/1852* (2013.01)
    USPC ....................................................... 556/142

(58) Field of Classification Search
None
See application file for complete search history.

(56) References Cited

U.S. PATENT DOCUMENTS

| | | |
|---|---|---|
| 7,011,854 B2 | 3/2006 | Haas et al. |
| 7,045,140 B2 | 5/2006 | Motterlini et al. |
| 7,238,469 B2 | 7/2007 | Bach et al. |
| 7,678,390 B2 | 3/2010 | Choi et al. |
| 2006/0127501 A1 | 6/2006 | Motterlini et al. |
| 2006/0147548 A1 | 7/2006 | Motterlini et al. |
| 2006/0148900 A1 | 7/2006 | Haas et al. |
| 2006/0233890 A1 | 10/2006 | Haas et al. |
| 2007/0065485 A1 | 3/2007 | Motterlini et al. |
| 2007/0202083 A1 | 8/2007 | Bach et al. |
| 2007/0207217 A1 | 9/2007 | Haas et al. |
| 2010/0105770 A1 | 4/2010 | Motterlini et al. |
| 2011/0015263 A1 | 1/2011 | Motterlini et al. |

FOREIGN PATENT DOCUMENTS

| | | |
|---|---|---|
| WO | WO 03/000114 A2 | 1/2003 |
| WO | WO 03/094932 A1 | 11/2003 |
| WO | WO 2007/085806 A2 | 8/2007 |

OTHER PUBLICATIONS

Howell et al., J. Organometallic Chem. 1996, 4247-4257.*

A. M. K. Choi et al.: "Emerging Role of Carbon Monoxide in Physiologic and Pathophysiologic States", Antioxidants & Redox Signaling, vol. 4, No. 2, pp. 227-228 (2002).
S.W. Ryter et al.: "Heme Oxygenase-1/Carbon Monoxide: From Basic Science to Therapeutic Applications", Physiol. Rev. 86, pp. 583-650 (2006).
R. Motterlini et al.: "Bioactivity and Pharmacological Actions of Carbon Monoxide-Releasing Molecules", Current Pharmaceutical Design, vol. 9, pp. 2525-2539 (2003).
B. E. Mann et al.: "CO and NO medicine", Chem. Commun., pp. 4197-4208 (2007).
R. Alberto et al.: "Chemistry and biological activities of CO-releasing molecules (CORMs) and transition metal complexes", Dalton Transactions., pp. 1651-1660 (2007).
R. Motterlini et al.: "The therapeutic potential of carbon monoxide", Nature Reviews Drug Discovery, vol. 9, pp. 728-743 (Sep. 2010).
T.R. Johnson et al.: "Metal carbonyls as pharmaceuticlas? [Ru(CO)₃Cl(glycinate)], a CO-releasing molecule with an extensive acqueous solution chemistry", Dalton Trans., pp. 1500-1508 (2007).
R. Motterlini et al.: "Therapeutic applications of carbon monoxide-releasing molecules", Expert. Opinion Investig. Drugs, vol. 14(11), pp. 1305-1318 (2005).
R. Foresti et al.: "Use of carbon monoxide as a therapeutic agent: promises and challenges", Intensive Care Med., vol. 34, pp. 649-658 (2008).
R. Motterlini et al.: "CORM-A1: a new pharmacologically active carbon monoxide-releasing molecule", The FASEB Journal, vol. 19, pp. 284-286 (2005).
T.S. Pitchumony et al.: " Syntheses, structural characterization and CO releasing properties of boranocarbonate (H₃BCO₂H)⁻derivatives", Organic & Biomolecular Chemistry., vol. 8, pp. 4849-4854 (2010).
J. Niesel et al.: "Photoinduced CO release, cellular uptake and cytotoxicity of a tris(pyrazolyl)methane (tpm) manganese tricarbonyl comlex", Chem. Commun., pp. 1798-1800 (2008).
R.D. Rimmer et al.: "A Photochemical Precursor for Carbon Monoxide Release in Aerated Aqueous Media", Inorg. Chem., vol. 49, pp. 1180-1185 (2010).
U. Schatzschneider: "Photoactivated Biological Activity of Transition-Metal Complexes", Eur. J. Inorg. Chem., pp. 1451-1467 (2010).
A. Bohác et al.: "Cyclic β-diketones—precursors of chiral 1,3-cyclohexadiene iron carbonyl complexes. Ligand exchange—(--)-PPh₂(O-HC*(Me)-CooEt)—new, chiral, diastereomer-seperating ligand in organoiron chemistry", Journal of Organometallic Chemistry, vol. 507, pp. 23-29 (1996).
A. Bohac et al.: "A Convenient Synthesis of 1,3-Diacetoxy-1,3-cycloalkadienes from Cyclic β-Diketones", Synthesis, pp. 881-882 (Oct. 1991).
M.C.P. Yeh et al.: "Bromination and alkylation of tricarbonyl(η¹, η²-but-3-en-1-yl)iron(0) anion complexes" Journal of Organometallic Chemistry, vol. 419, p. 341-355 (1991).

(Continued)

*Primary Examiner* — Brandon Fetterolf
*Assistant Examiner* — Ana Z Muresan
(74) *Attorney, Agent, or Firm* — Norman B. Thot

(57) ABSTRACT

The present invention provides acyloxy- and phosphoryloxy-butadiene-Fe(CO)₃ complexes which can deliver carbon monoxide to a physiological target, wherein release of carbon monoxide can be enzymatically-triggered. The present invention also provides for methods of manufacturing the enzymatically-triggered carbon monoxide releasing molecules and methods for their use.

9 Claims, 13 Drawing Sheets

(56) References Cited

OTHER PUBLICATIONS

R. E. Ireland et al.: "Homogeneous Catalytic Hydrogenation: Dihydrocarvone", Organic Syntheses, Coll., vol. 6, p. 459 (1988); vol. 53, p. 63 (1973).

W. Miller et al.: "Sonogashira Coupling of 2-Iodo-2-cycloalkenones: Synthesis of (+)- and (−)-Harveynone and (−)-Tricholomenyn A", Journal of Organic Chemistry, vol. 62, p. 1582 (1997).

K. Winska et al.: "Enzymatic resolution of racemic secondary cyclic allylic alcohols", Tetrahedron: Asymmetry, 21, pp. 670-678 (2010).

R. Motterlini et al.: "Carbon Monoxide-Releasing Molecules: Characterization of Biochemical and Vascular Activities", Circulation Research, 90, pp. e17-e24 (2002).

W. C. Raschke et al.: "Functional Macrophage Cell Lines Transported by Abelson Leukemia Virus", Cell, vol. 15, pp. 261-267 (Sep. 1978).

T. Mosmann: "Rapid Colorimetric Assay for Cellular Growth and Survival: Application to Proliferation and Cytotoxicity Assays", Journal of Immunological Methods, vol. 65, pp. 55-63 (1983).

R. J. Gillies et al.: "Determination of Cell Number In Monolayer Cultures", Analytical Biochemistry 159, pp. 109-113 (1986).

E. Park et al.: "Taurine chloramine inhibits the synthesis of nitric oxide and the release of tumor necrosis factor in activated RAW 264.7 cells", Journal of Leukocyte Biology, vol. 54, pp. 119-124 (Aug. 1993).

H. Pfeiffer et al.: "Sonogashira and "Click" reactions for the N-terminal and side-chain functionalization of peptides with [Mn(CO)$_3$(tpm)]$^+$-based CO releasing molecules (tpm = tris(pyrazolyl)methane)", Dalton Trans., pp. 4292-4298 (2009).

J. Dulak et al.: "Heme Oxygenase Activity Modulates Vascular Endothelial Growth Factor Synthesis in Vascular Smooth Muscle Cells", Antioxidants & Redox Signaling, vol. 4, pp. 229-240 (Nov. 2, 2002).

J. M. Sethi et al.: "Differential Modulation by Exogenous Carbon Monoxide of TNF-α Stimulated Mitogen-Activated Protein Kinases in Rat Pulmonary Artery Endothelial Cells", Antioxidants & Redox Signaling, vol. 4, pp. 241-240 (Nov. 2, 2002).

P. Gong et al.: "Activation of the Mouse Heme Oxygenase-1 Gene by 15-Deoxy-D$^{12,14}$-Prostaglandin J$_2$ Is Mediated by the Stress Response Elements and Transcription Factor Nrf2", Antioxidants & Redox Signaling, vol. 4, pp. 249-257 (Nov. 2, 2002).

C. A. Piantadosi: Biological Chemistry of Carbon Monoxide, Antioxidants & Redox Signaling, vol. 4, pp. 259-270 (Nov. 2, 2002).

G. S. Marks et al.: "Measurement of Endogenous Carbon Monoxide Formation in Biological Systems", Antioxidants & Redox Signaling, vol. 4, pp. 271-277 (Nov. 2, 2002).

R. C. Koehler et al.: "Cerebrovascular Effects of Carbon Monoxide", Antioxidants & Redox Signaling, vol. 4, pp. 279-290 (Nov. 2, 2002).

S. Kiourembanas: "Hypoxia and Carbon Monoxide in the Vasculature", Antioxidants & Redox Signaling, vol. 4, pp. 291-299 (Nov. 2, 2002).

C. L. Hartsfield: "Cross Talk Between Carbon Monoxide and Nitric Oxide", Antioxidants & Redox Signaling, vol. 4, pp. 301-307 (Nov. 2, 2002).

L. E. Otterbein: "Carbon Monoxide: Innovative Anti-inflammatory Properties of an Age-Old Gas Molecule", Antioxidants & Redox Signaling, vol. 4, pp. 309-319 (Nov. 2, 2002).

M. P. Soares et al.: "Modulation of Endothelial Cell Apoptosis by Heme Oxygenase-l-Derived Carbon Monoxide", Antioxidants & Redox Signaling, vol. 4, pp. 321-329 (Nov. 2, 2002).

D. Morse et. al.: "Carbon Monoxide and Human Disease", Antioxidants & Redox Signaling, vol. 4, pp. 331-338 (Nov. 2, 2002).

T. Asami et al.: "Synthesis and Activity of 3-(1-Alkylaminoalylidene)-2H-pyran-2,4(3H)-diones as New Photosynthetic Electron Transport Inhibitors", Agric. Biol. Chem., 51 (10), pp. 2775-2780 (1987).

* cited by examiner

ACYLOXY- AND PHOSPHORYLOXY-BUTADIENE-FE(CO)₃ COMPLEXES AS ENZYME-TRIGGERED CO-RELEASING MOLECULES

FIELD

The present invention provides acyloxy- and phosphoryloxy-butadiene-Fe(CO)$_3$ complexes which can deliver carbon monoxide to a physiological target, wherein release of carbon monoxide can be enzymatically-triggered. The present invention also provides for methods of manufacturing the enzymatically-triggered carbon monoxide releasing molecules and methods for their use.

BACKGROUND

Carbon monoxide (CO) is a colorless, odorless, tasteless, non-corrosive gas of about the same density of air. It is well known that carbon monoxide gas is poisonous in high concentrations. Like nitric oxide (NO), carbon monoxide is an important, yet only recently recognized biological signaling molecule, as is described, for example, by M. K. Choi, L. E. Otterbein (eds.), Antioxidants & Redox signaling, 4, pp 227-338 (2002). It has also been suggested that carbon monoxide acts as a neuronal messenger molecule in the brain and as a neuro-endocrine modulator in the hypothalamus. Like nitric oxide, carbon monoxide is also a smooth muscle relaxant and inhibits platelet aggregation.

Carbon monoxide is constantly produced in small doses in the human body in the course of heme degradation by the heme-oxygenase (HO) enzymes. Carbon monoxide exhibits cytoprotective, anti-inflammatory, vasodilatory and other effects, which are of importance, for instance, in our body's response to injuries as described, for example, in S. W. Ryter, J. Alam, A. M. K. Choi: Physiol. Rev., 86, pp 583-650 (2006). Despite these beneficial biological properties, the application of carbon monoxide as a therapeutic agent has only recently garnered attention. The application of carbon monoxide as a therapeutic agent is described in various patents and in the literature.

WO 03/000114 A2 describes the use of carbon monoxide as a gas, liquid or dissolved in aqueous solution to promote the survival and function of organ, tissue and individual cell transplants. The carbon monoxide can thereby be delivered via inhalation, intravenously or via perfusion through the blood vessels of an organ or tissue. WO 03/094932 A1 and U.S. Pat. No. 7,678,390 B2 describe the use of carbon monoxide as a biomarker and therapeutic agent of heart, lung, liver, spleen, brain, skin and kidney diseases and other conditions and disease states including, for example, asthma, emphysema, bronchitis, adult respiratory distress syndrome, sepsis, cystic fibrosis, pneumonia, interstitial lung diseases, idiopathic pulmonary diseases, other lung diseases including primary pulmonary hypertension, secondary pulmonary hypertension, cancers, including lung, larynx and throat cancer, arthritis, wound healing, Parkinson's disease, Alzheimer's disease, peripheral vascular disease and pulmonary vascular thrombotic diseases such as pulmonary embolism. The use of carbon monoxide is also described to provide anti-inflammatory relief in patients suffering from oxidative stress and other conditions especially including sepsis and septic shock and as a biomarker or therapeutic agent for reducing respiratory distress in lung transplant patients and to reduce or inhibit oxidative stress and inflammation in transplant patients. U.S. Pat. No. 7,678,390 B2 thereby describes the delivery of carbon monoxide as a gaseous composition while WO 03/094932 A1 describes delivery in both gaseous and liquid form.

U.S. Pat. No. 7,238,469 B2 describes the administration of carbon monoxide to enhance the survival of cells following transplantation. The carbon monoxide is thereby administered as a gas, liquid or as a composition.

The use of gaseous carbon monoxide is risky and is strongly limited by the high affinity of carbon monoxide towards hemoglobin and the resulting systemic effects on oxygen transport and low bioavailability. This affinity to bind to hemoglobin in the blood stream rapidly decreases the oxygen transport capability of the cardiovascular system.

A strategy to circumvent these problems and to deliver controlled amounts of carbon monoxide directly to a tissue is the use of carbon monoxide-releasing molecules (so called CORMs). Roberto A. Motterlini has identified a series of transition-metal carbonyl complexes fulfilling this function as is described, for example, in R. Motterlini, B. E. Mann, T. R. Johnson, J. E. Clark, R. Foresti, C. J. Green: Curr. Pharm. Design, 9, pp 2525-2539 (2003); B. E. Mann, R. Motterlini, Chem. Commun., pp 4197-4208 (2007); R. Alberto, R. Motterlini: Dalton Trans., pp 1651-1660 (2007); and in R. Motterlini, L. E. Otterbein, NatureRev. Drug Discov., 9, pp 728-743 (2010). The first CORMs, such as $Mn_2(CO)_{10}$, required UV activation. The dinuclear Ru-complex 1 (CORM-2), having the formula

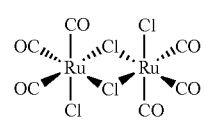

CORM 2 liberates carbon monoxide upon ligand exchange with dimethyl sulfoxide (DMSO).

The related mononuclear glycinato complex 2 (CORM-3) having the formula

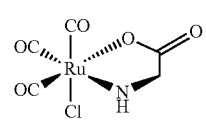

CORM 3 has better solubility in water and releases carbon monoxide under physiological conditions as described, for example, by T. R. Johnson, B. E. Mann, I. P. Teasdale, H. Adams, R. Foresti, C. J. Green, R. Motterlini: Dalton Trans., pp 1500-1508 (2007).

Existing CORM compounds suffer from serious limitations. For example, the carbon monoxide release from CORM 3 is very fast ($t_{1/2} \approx 1$ min) and unspecific as is described by R. Motterlini, B. E. Mann, R. Foresti: Expert. Opin. Investig. Drugs, 14, pp 1305-1318 (2005). This hampers the delivery of controlled amounts of carbon monoxide to a target tissue.

Various approaches have been suggested to overcome this problem. For example, R. Foresti, M. G. Bani-Hani, R. Motterlini: Intensive Care Med., 34, pp 649-658 (2008) describes the use of stable molecules as precursors which are then converted into CORMs by means of a trigger. One such possible trigger is pH which leads to a pH-dependent carbon monoxide liberation from a boranocarbonate as described by R. Motterlini, P. Sawle, J. Hammad, S. Bains, R. Alberto, R.

Foresti, C. J. Green: FASEB, 19, pp 284-286 (2005) or from amino derivatives of boranocarbonates as is described in T. S. Pitchumony, B. Spingler, R. Motterlini, R. Alberto: Org. Biomol. Chem., 8, pp 4849-4854 (2010). Another approach is the photo-induced carbon monoxide release of transition-metal carbonyl complexes of UV-absorbing organic ligands. This approach is described, for example, in J. Niesel, A. Pinto, H. W. Peindy N'Dongo, K. Merz, I. Ott, R. Gust, U. Schatzschneider: Chem. Commun., pp 1798-1800 (2008); H. Pfeiffer, A. Rojas, J. Niesel, U. Schatzschneider: Dalton Trans., pp 4292-4298 (2009); R. D. Rimmer, H. Richter, P. C. Ford: Inorg. Chem., 49, pp 1180-1185 (2010); and in U. Schatzschneider: Eur. J. Inorg. Chem., pp 1451-1467 (2010).

The patent literature also describes various CORMs and releasing mechanisms. U.S. Pat. No. 7,011,854 B2, US 2006/0148900 A1 and US 2006/0233890 A1 describe CORMs and a method for treating a mammal by administration thereof. The preferred CORMs comprise two components, a carbon monoxide releasing moiety, and a second pharmaceutically important molecule, such as a known drug carrier, and/or a known anti-inflammatory agent. A preferred class of conjugation partners for the carbon monoxide-donors include non-steroidal anti-inflammatory drugs (NSAIDs), such as aspirin and anti-inflammatory agents, such as steroids and inhibitors of phosphodiesterases (PDE), such as inhibitors of PDE4. US 2006/0148900 A1 thereby concentrates on organic substances while US 2006/0233890 A1 seeks to disclaim CORMs which include, for example, an Fe or Ru complex. Release of carbon monoxide occurs either spontaneously or by a metabolic process involving one or more enzymes. Release mechanisms for spontaneous release include thermal, chemical, oxydatively induced release and release by reactions induced by light. Enzymes for metabolic process release can include, for example, cytochrome P450 and glutathione S-transferase.

US 2007/0207217 A1 describes molybdenum carbonyl CORM complexes useful for inhibiting tumor necrosis factor (TNF) production and for treating inflammatory diseases. Release mechanisms for the molybdenum carbonyl CORM complexes include both spontaneous release means and release by metabolic process means via the involvement of one or more enzymes.

None of U.S. Pat. No. 7,011,854 B2, US 2006/0148900 A1, US 2006/0233890 A1 and US 2007/020717 A1 provide a proof of concept of how a CORM can release carbon monoxide using an enzyme as a trigger. Each of U.S. Pat. No. 7,011,854 B2, US 2006/0148900 A1 and US 2006/0233890 A1 merely describe that certain organic substances, such as polyhalomethanes, produce dichlorocarbene which, under physiological conditions, will in turn be metabolized to carbon monoxide.

U.S. Pat. No. 7,045,140 B2 describes metal carbonyl CORMs to deliver carbon monoxide. The described CORMs typically have Ru or Fe as the complexing metal, whereby Fe is combined with a cyclopentadiene, and preferably has one or more ligands other than carbon monoxide, such as an amino acid. Various release mechanisms such as dissociation of the metal carbonyl, contact with a solvent, contact with a tissue organ or cell, and via irradiation are described. US 2007/0065485 A1 describes boranocarbonate CORMs which can be administered with a guanylate cyclase stimulate or stabilizer. US 2006/0127501 A1 describes metal carbonyls as CORMs to deliver carbon monoxide to limit post-ischaemic damage. The majority of the specifically disclosed CORMs contain ruthenium as the complexing metal and preferably contain one or more other ligands apart from carbon monoxide such as amino acids. US 2006/0147548 A1 describes CORMs comprising metal carbonyls used in combination with at least one guanylate cyclase stimulate or stabilizer. The majority of the specifically disclosed CORMs contain ruthenium as the complexing metal. WO 2007/085806 A2 describes CORMs that employ transition metal complexes having at least a substituted cyclopentadenyl, indenyl or fluorenyl ligand and two or more carbonyl ligands. US 2010/0105770 A1 describes CORMs comprising Mn complexes having carbon monoxide ligands which can be used for the therapeutic delivery of carbon monoxide.

None of the CORMs described to date have provided a satisfactory solution for the target-specific release of carbon monoxide.

SUMMARY

An aspect of the present invention was to provide a CORM as an active ingredient which would enable the delivery of carbon monoxide to a physiological target wherein the release of carbon monoxide is more precise than that described in the prior art. A further, alternative aspect of the present invention is to provide a CORM wherein the more precise release of the carbon monoxide is enzymatically triggered. An additional, alternative aspect of the present invention is to provide for a method of manufacturing the CORMs as well as methods for their use.

In an embodiment, the present invention provides $\eta^4$-1,3-diene-Fe(CO)$_3$ complex having the formula (I):

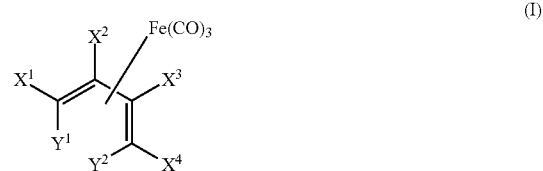

where, $X^1, X^2, X^3, X^4, Y^1$ and $Y^2$ are, independently of each other, H, halogen, N$_3$, cyano, alkyl, alkenyl, alkynyl, aryl, hetero-aryl, alkoxy, aryloxy, alkylsulfido, arylsulfido, alkylamino, arylamino, acyl, alkoxylcarbonyl, acylsulfanyl, acyloxy (—OC(=O)R$^1$, acylamino (—N(R$^2$)C(=O)R$^3$ or phosphoryloxy (OP(=O)(R$^4$)(R$^5$), wherein, $R^1$ is H, alkyl, alkenyl, alkynyl, aryl, hetero-aryl, alkoxy, aryloxy, alkylamino, arylamino, alkylacyl, or arylacyl, $R^2$ and $R^3$ are, independently of each other, H, alkyl, alkenyl, alkynyl, aryl, hetero-aryl, alkoxy, aryloxy, alkylamino, arylamino, alkylacyl, or arylacyl, $R^4$ and $R^5$ are, independently of each other, OH, O$^-$ (as a salt), H, alkyl, alkenyl, alkynyl, aryl, hetero-aryl, alkoxy, aryloxy, alkylamino, arylamino, each of the alkyl, the alkenyl, the alkylnyl, the aryl, the hetero-aryl, the alkoxy, the aryloxy, the alkylsulfido, the arylsulfido, the alkylamino, the arylamino, the acyl and the acylsulfanyl can be substituted by at least one of alkyl, alkenyl, alkynyl, aryl, heteroaryl, alkoxy, aryloxy, acyl, hydroxy, amino, alkylamino, arylamino, halogeno, azido, oxo, imino, cyano and sulfanyl, two or more of $X^1, X^2, X^3, X^4, Y^1$ and $Y^2$ may be connected to form a cyclic or polycyclic structure with an overall ring size of 5 to 20, at least one of $X^1, X^2, X^3, X^4, Y^1$ and $Y^2$ contains at least one of acyloxy (—OC(=O)R$^1$) and phosphoryloxy (OP(=O)(R$^4$)(R$^5$), and the following complexes are specifically excluded:

a) complexes having the formula (II):

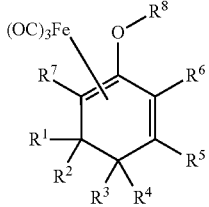

(II)

wherein $R^1, R^2, R^3, R^4, R^5, R^6, R^7$ and $R^8$ are, with respect to complexes 1-15, as set forth in Table 1:

TABLE 1

| No. | $R^1$ | $R^2$ | $R^3$ | $R^4$ | $R^5$ | $R^6$ | $R^7$ | $R^8$ |
|---|---|---|---|---|---|---|---|---|
| 1 | H | H | $CH_3$ | $CH_3$ | H | H | H | COMe |
| 2 | H | H | $CH_3$ | $CH_3$ | H | H | H | $P(O)(OEt)_2$ |
| 3 | H | H | $CH_3$ | $CH_3$ | H | H | H | $P(O)(Oi-Pr)_2$ |
| 4 | H | H | $CH_3$ | $CH_3$ | H | H | H | $P(O)(OPh)_2$ |
| 5 | H | H | $CH_3$ | $CH_3$ | H | H | H | $P(O)(NMe_2)_2$ |
| 6 | H | H | H | H | $CH_3$ | H | H | $P(O)(OEt)_2$ |
| 7 | $CH_3$ | H | H | H | $CH_3$ | H | H | $P(O)(OEt)_2$ |
| 8 | $CH_3$ | $CH_3$ | H | H | $CH_3$ | H | H | $P(O)(OEt)_2$ |
| 9 | H | H | H | H | H | H | H | $P(O)(OEt)_2$ |
| 10 | H | H | H | H | H | H | H | R* |
| 11 | H | H | H | H | H | H | H | ent-R* |
| 12 | H | H | H | H | OAc | H | H | COMe |
| 13 | $CH_3$ | $CH_3$ | H | H | OAc | H | H | COMe |
| 14 | H | H | $CH_3$ | H | H | H | H | R* |
| 15 | H | H | $CH_3$ | H | H | H | H | ent-R* | b) complexes having the formula (III):

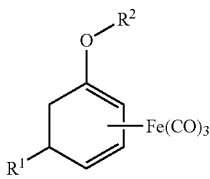

(III)

wherein $R^1$ and $R^2$ are, with respect to complexes 16-18, as set forth in Table 2:

TABLE 2

| No | $R^1$ | $R^2$ |
|---|---|---|
| 16 | H | R* |
| 17 | H | ent-R* |
| 18 | $CH_3$ | COMe | c) complexes having the formula (IV):

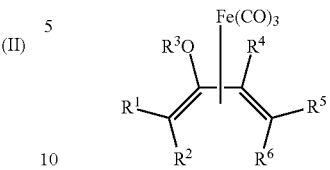

(IV)

wherein $R^1, R^2, R^3, R^4, R^5$ and $R^6$ are, with respect to complexes 19-29, as set forth in Table 3:

TABLE 3

| No. | $R^1$ | $R^2$ | $R^3$ | $R^4$ | $R^5$ | $R^6$ |
|---|---|---|---|---|---|---|
| 19 | $CH_3$ | H | $P(O)(OEt)_2$ | H | $C_6H_5$ | H |
| 20 | $CH_3$ | H | $P(O)(OEt)_2$ | H | $CH_3$ | H |
| 21 | H | H | $P(O)(OEt)_2$ | H | H | H |
| 22 | H | H | $P(O)(OEt)_2$ | H | i-Pr | H |
| 23 | H | H | $P(O)(OEt)_2$ | H | $C_6H_5$ | H |
| 24 | H | H | COMe | H | H | H |
| 25 | H | H | COPh | H | H | H |
| 26 | H | H | R* | H | i-Pr | H |
| 27 | H | H | R* | H | $C_6H_5$ | H |
| 28 | H | H | ent-R* | H | i-Pr | H |
| 29 | H | H | ent-R* | H | $C_6H_5$ | H | d) complexes having the formula (V):

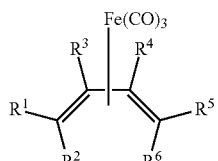

(V)

wherein $R^1, R^2, R^3, R^4, R^5$ and $R^6$ are, with respect to complexes 30-36, as set forth in Table 4:

TABLE 4

| No. | $R^1$ | $R^2$ | $R^3$ | $R^4$ | $R^5$ | $R^6$ |
|---|---|---|---|---|---|---|
| 30 | H | $CO_2Me$ | H | H | COMe | H |
| 31 | H | COMe | H | H | COME | H |
| 32 | H | COPh | H | H | COME | H |
| 33 | H | H | H | H | COMe | H |
| 34 | H | H | H | H | COPh | H |
| 35 | $CH_3$ | H | H | H | R* | H |
| 36 | $CH_3$ | H | H | H | ent-R* | H | e) complexes having the formula (VI):

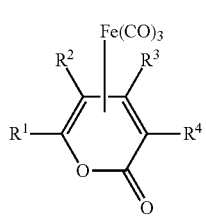

(VI)

wherein $R^1$, $R^2$, $R^3$ and $R^4$ are, with respect to complexes 37-46, as forth in Table 5:

TABLE 5

| No. | $R^1$ | $R^2$ | $R^3$ | $R^4$ |
|---|---|---|---|---|
| 37 | H | H | H | H |
| 38 | CH$_3$ | H | Cl | H |
| 39 | CH$_3$ | H | CH$_3$ | H |
| 40 | CH$_3$ | H | I | H |
| 41 | H | H | Cl | H |
| 42 | CH$_3$ | H | H | H |
| 43 | CH$_3$ | H | Br | H |
| 44 | H | Br | H | H |
| 45 | H | C$_6$H$_5$ | H | H |
| 46 | H | C$_6$H$_5$-4-OMe | H | H | f) complexes having the formula (VII):

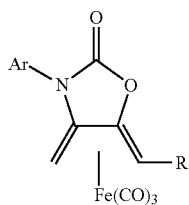
(VII)

wherein Ar and R are, with respect to complexes 47-63, as set forth in Table 6:

TABLE 6

| No. | Ar | R |
|---|---|---|
| 47 | C$_6$H$_5$ | H |
| 48 | C$_6$H$_5$ | H |
| 49 | C$_6$H$_5$ | H |
| 50 | C$_6$H$_4$-2-Me | H |
| 51 | C$_6$H$_4$-4-Me | H |
| 52 | C$_6$H$_4$-3-Cl | H |
| 53 | C$_6$H$_4$-4-Cl | H |
| 54 | C$_6$H$_5$ | Me |
| 55 | C$_6$H$_4$-2-Me | Me |
| 56 | C$_6$H$_4$-4-Me | Me |
| 57 | C$_6$H$_4$-3-Cl | Me |
| 58 | C$_6$H$_4$-4-Cl | Me |
| 59 | C$_6$H$_5$ | Et |
| 60 | C$_6$H$_4$-2-Me | Et |
| 61 | C$_6$H$_4$-4-Me | Et |
| 62 | C$_6$H$_4$-3-Cl | Et |
| 63 | C$_6$H$_4$-4-Cl | Et | g) complexes having the formula (VIII):

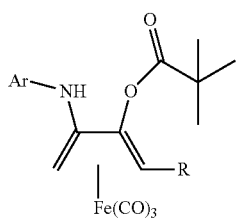
(VIII)

wherein Ar and R are, with respect to complexes 64-67, as set forth in Table 7:

TABLE 7

| No. | Ar | R |
|---|---|---|
| 64 | C$_6$H$_5$ | H |
| 65 | C$_6$H$_5$ | Me |
| 66 | C$_6$H$_4$-4-Cl | Me |
| 67 | C$_6$H$_5$ | Et | h) complexes having the formula (X):

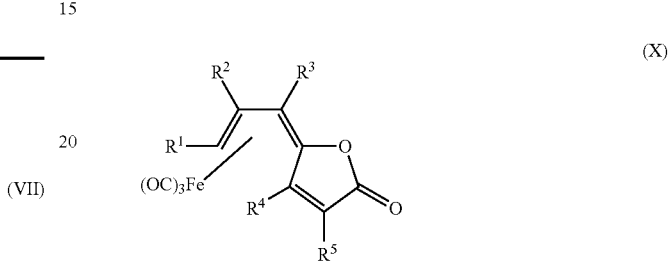
(X)

wherein $R^1$, $R^2$, $R^3$, $R^4$ and $R^5$ are, with respect to complexes 68-70, as set forth in Table 8:

TABLE 8

| Nr. | $R^1$ | $R^2$ | $R^3$ | $R^4$ | $R^5$ |
|---|---|---|---|---|---|
| 68 | H | C$_6$H$_5$ | C$_6$H$_5$ | C$_6$H$_5$ | C$_6$H$_5$ |
| 69 | C$_6$H$_5$ | H | t-Bu | C$_6$H$_5$ | CO$_2$Et |
| 70 | C$_6$H$_5$ | H | t-Bu | C$_6$H$_5$ | SO$_2$Me | and i) complexes 71-73 below:

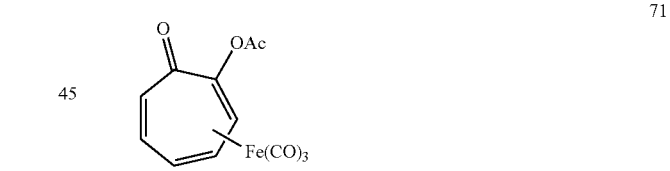
71

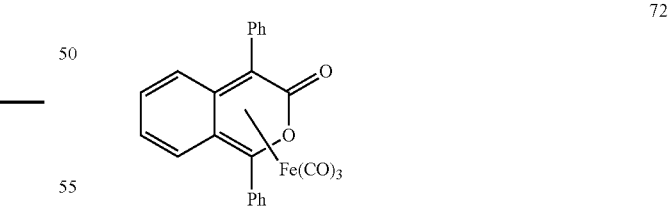
72

73 wherein for complexes 1-73, Ac is acetyl, Bu is butyl, Me is methyl, Et is Ethyl, NME is N-methylamide, i-Pr is isopro pyl, Pr is propyl, Ph is phenyl, R* is a substituent of the formula

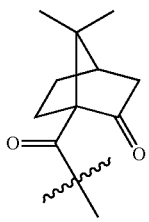

and ent-R* is an enantiomer of R*. The complexes are hereinafter referred to as the "inventive complex(es)".

BRIEF DESCRIPTION OF THE DRAWINGS

The present invention is described in greater detail below on the basis of embodiments and of the drawings in which.

DETAILED DESCRIPTION

Figure 1:
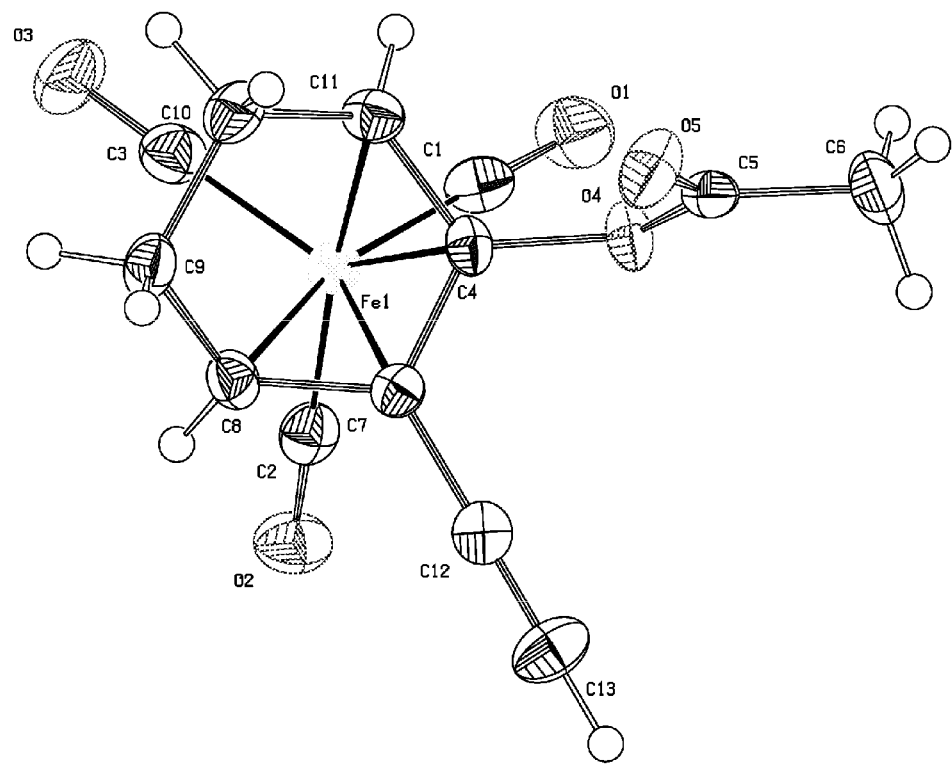
FIG. 1 shows the molecular structure for (RS)-[$\eta^4$-6-ethynylcyclohexa-1,5-dien-1-yl-tricarbonyliron(0)]acetate (rac-91) obtained by X-ray crystallography.

In an embodiment of the present invention, two or more of $X^1$, $X^2$, $X^3$, $X^4$, $Y^1$ and $Y^2$ may be connected in formula (I) to form a cyclic or polycyclic structure with an overall ring size of 5 to 10, for example, 6 to 7.

Examples of inventive complexes having the aforementioned cyclic or polycyclic structure are inventive complexes 74 to 76:

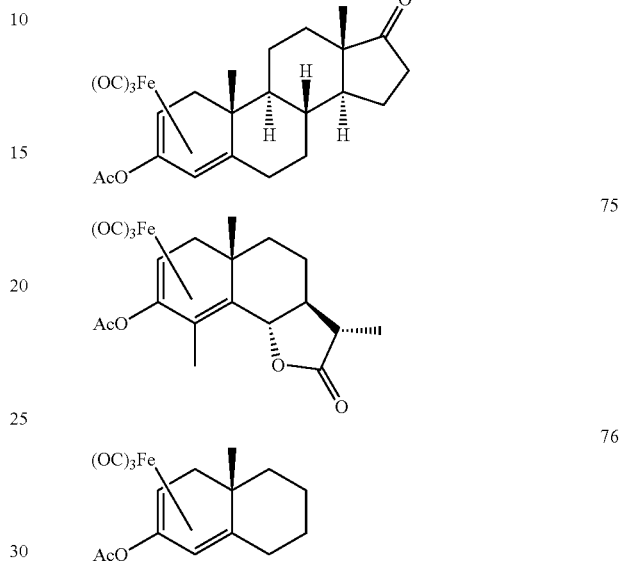

In an embodiment of the present invention, $Y^1$ and $Y^2$ can be connected to each other in formula (I) to form a carbocyclic or a heterocyclic ring with a ring size of 5 to 20; for example, 5 to 10, or more specifically, 6 to 7.

Examples of inventive complexes having the aforementioned carbocyclic or heterocyclic ring are inventive complexes 77 to 79:

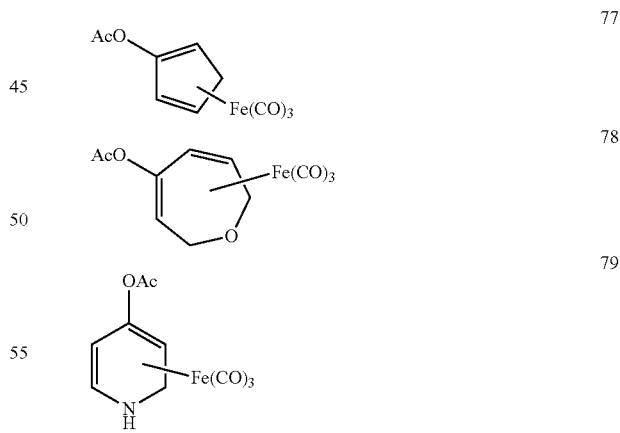

In an embodiment of the present invention, formula (I) can include stereoisomers and enantiomers arising from the complexation of non-symmetric diene ligands.

In an embodiment of the present invention, inventive complexes included under formula (I) include, for example, one or more of inventive complexes 80 to 99 as well as any stereoisomers thereof:

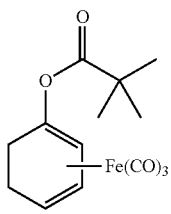
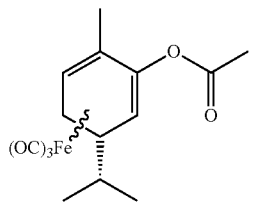
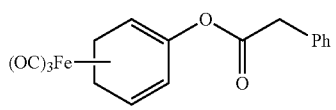
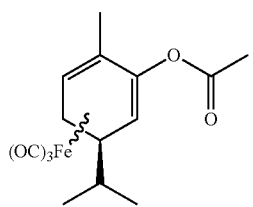
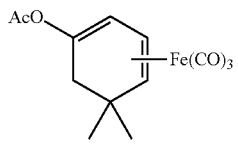
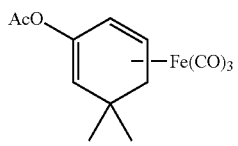
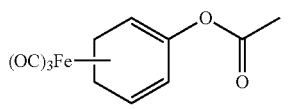
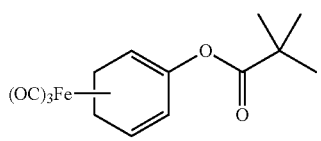
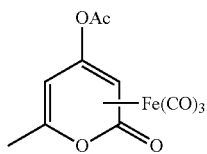
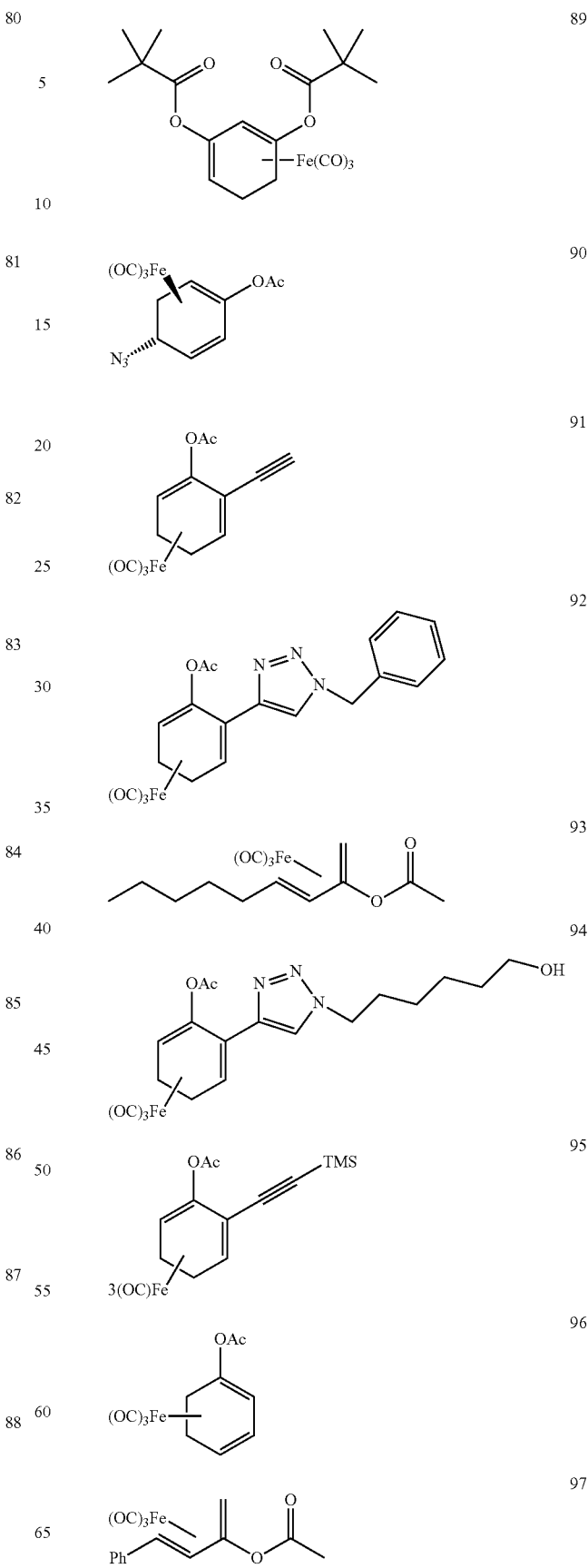

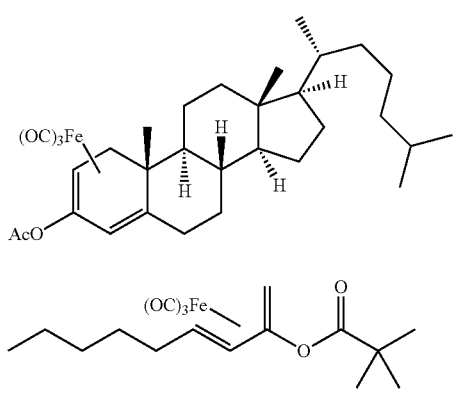

wherein Ph is phenyl, Ac is acetyl and TMS is trimethylsilyl.

Unless otherwise specified, a reference to a particular inventive complex also includes salt forms thereof to the extent chemically relevant. Such relevance would be present, for example, if an inventive complex possesses a functional group, such as a carboxyl group, which is capable of forming a salt.

The present invention also provides for methods of manufacturing the inventive complexes.

In an embodiment of the present invention, an inventive complex can be prepared by providing a dienylester ligand, providing a Fe(CO)$_3$ transfer reagent, and complexing the dienylester ligand with the Fe(CO)$_3$ transfer reagent to obtain an inventive complex. The dienylester ligand can, for example, be an acyloxy-diene or a phosphoryloxydiene.

Examples of dienylester ligands which can be complexed with the Fe(CO)$_3$ transfer reagent to obtain an inventive complex include compounds L1 to L16:

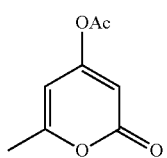
L1

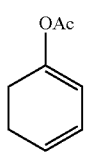
L2

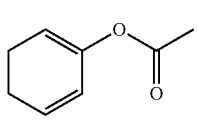
L3

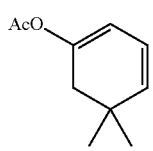
L4

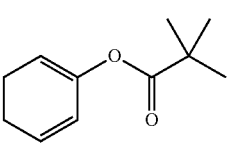
L5

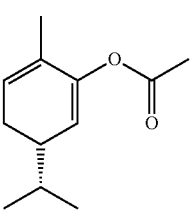
L6

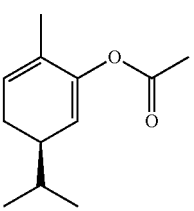
L7

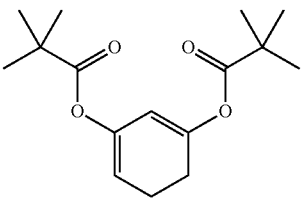
L8

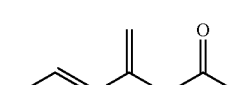
L9

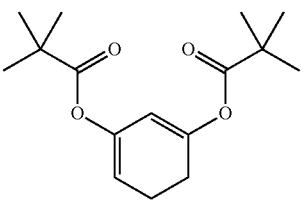
L10

L11

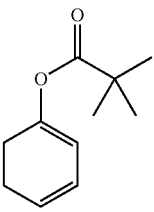
L12

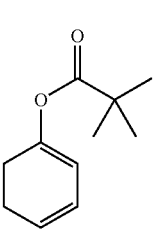
L13

L14

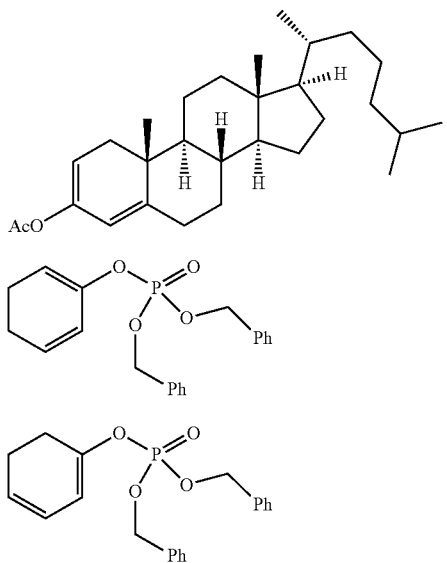

L15

L16

In an embodiment of the present invention, an inventive complex can be prepared by providing an intermediate dienol-Fe(CO)₃ complex, and acylating and/or phosphorylating the intermediate dienol-Fe(CO)₃ complex to obtain an inventive complex.

The preparation of inventive complexes rac-82 and rac-99 are but two examples of acylating and/or phosphorylating the intermediate dienol-Fe(CO)₃ complex to obtain an inventive complex:

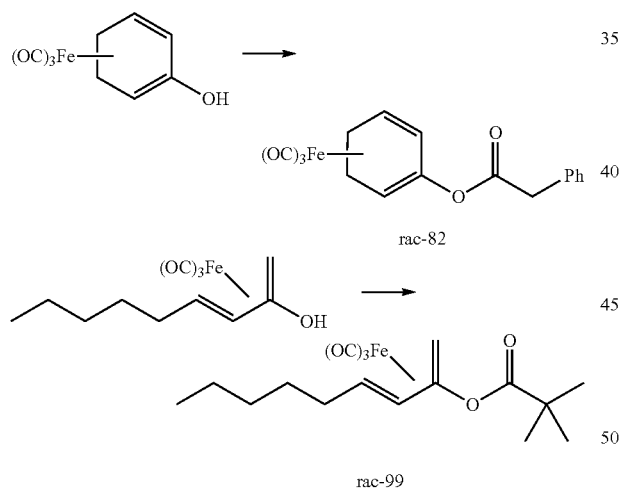

Complexes in this application which form racemic mixtures have been designated with the abbreviation "rac" and the complex number. "rac-82" is, for example, a racemic mixture of inventive complex 82.

The intermediate dienol-Fe(CO)₃ complex, can, for example, be a complex having the formula (I):

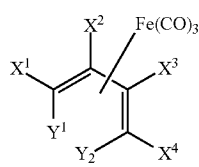

(I)

where, $X^1, X^2, X^3, X^4, Y^1$ and $Y^2$ are, independently of each other, H, halogen, $N_3$, cyano, alkyl, alkenyl, alkynyl, aryl, heteroaryl, alkoxy, aryloxy, alkylsulfido, arylsulfido, alkylamino, arylamino, acyl, alkoxylcarbonyl, acylsulfanyl, acyloxy (—OC(=O)R¹), acylamino (—N(R²)C(=O)R³ or phosphoryloxy (OP(=O)(R⁴)(R⁵)), wherein, $R^1$ is H, alkyl, alkenyl, alkynyl, aryl, hetero-aryl, alkoxy, aryloxy, alkylamino, arylamino, alkylacyl, or arylacyl, $R^2$ and $R^3$ are, independently of each other, H, alkyl, alkenyl, alkynyl, aryl, hetero-aryl, alkoxy, aryloxy, alkylamino, arylamino, alkylacyl, or arylacyl, $R^4$ and $R^5$ are, independently of each other, OH, O⁻ (as a salt), H, alkyl, alkenyl, alkynyl, aryl, hetero-aryl, alkoxy, aryloxy, alkylamino, arylamino, each of the alkyl, the alkenyl, the alkynyl, the aryl, the hetero-aryl, the alkoxy, the aryloxy, the alkylsulfido, the arylsulfido, the alkylamino, the arylamino, the acyl and the acylsulfanyl can be substituted by at least one of alkyl, alkenyl, alkynyl, aryl, heteroaryl, alkoxy, aryloxy, acyl, hydroxy, amino, alkylamino, arylamino, halogeno, azido, oxo, imino, cyano and sulfanyl, two or more of $X^1, X^2, X^3, X^4, Y^1$ and $Y^2$ may be connected to form a cyclic or polycyclic structure with an overall ring size of 5 to 20, and at least one of $X^1, X^2, X^3, X^4$ is OH.

In an embodiment of the present invention, an inventive complex can be prepared by providing an intermediate acyloxy-diene complex and transesterifying the intermediate acyloxy-diene complex to obtain an inventive complex.

The preparation of inventive complex rac-86 from rac-87 shown below is but one example of providing an intermediate acyloxy-diene complex and transesterifying the intermediate acyloxy-diene complex to obtain an inventive complex:

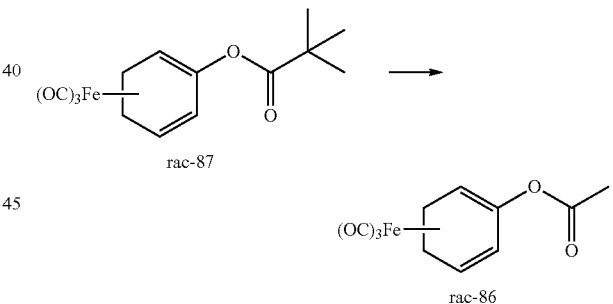

The intermediate acyloxy-diene complex can, for example, be a complex having the formula (I):

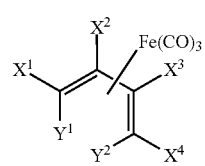

(I)

where, $X^1, X^2, X^3, X^4, Y^1$ and $Y^2$ are, independently of each other, H, halogen, $N_3$, cyano, alkyl, alkenyl, alkynyl, aryl, heteroaryl, alkoxy, aryloxy, alkylsulfido, arylsulfido, alkylamino, arylamino, acyl, alkoxylcarbonyl, acylsulfanyl, acyloxy (—OC(=O)R$^1$, acylamino (—N(R$^2$)C(=O)R$^3$ or phosphoryloxy (OP(=O)(R$^4$)(R$^5$), wherein, R$^1$ is H, alkyl, alkenyl, alkynyl, aryl, hetero-aryl, alkoxy, aryloxy, alkylamino, arylamino, alkylacyl, or arylacyl, R$^2$ and R$^3$ are, independently of each other, H, alkyl, alkenyl, alkynyl, aryl, hetero-aryl, alkoxy, aryloxy, alkylamino, arylamino, alkylacyl, or arylacyl, R$^4$ and R$^5$ are, independently of each other, OH, O$^-$ (as a salt), H, alkyl, alkenyl, alkynyl, aryl, heteroaryl, alkoxy, aryloxy, alkylamino, arylamino, each of the alkyl, the alkenyl, the alkynyl, the aryl, the hetero-aryl, the alkoxy, the aryloxy, the alkylsulfido, the arylsulfido, the alkylamino, the arylamino, the acyl and the acylsulfanyl can be substituted by at least one of alkyl, alkenyl, alkynyl, aryl, heteroaryl, alkoxy, aryloxy, acyl, hydroxy, amino, alkylamino, arylamino, halogeno, azido, oxo, imino, cyano and sulfanyl, two or more of X$^1$, X$^2$, X$^3$, X$^4$, Y$^1$ and Y$^2$ may be connected to form a cyclic or polycyclic structure with an overall ring size of 5 to 20, and at least one of X$^1$, X$^2$, X$^3$, X$^4$ contains at least one of acyloxy (—OC(=O)R$^1$).

In an embodiment of the present invention, an inventive complex can be prepared by providing an acyl- or phosphoryloxy-substituted cationic pentadienyl-Fe(CO)$_3$ complex, and reacting the acyl- or phosphoryloxy-substituted cationic pentadienyl-Fe(CO)$_3$ with a nucleophile to obtain an inventive complex. A person skilled in the art will know which type of nucleophile can be used to obtain an inventive complex. The nucleophile can be, for example, morpholine, hydroxide, azide or cyanide, organometallic reagents or stabilized carbanion equivalents.

An example of reacting the acyl- or phosphoryloxy-substituted cationic pentadienyl-Fe(CO)$_3$ with a nucleophile to obtain an inventive complex is shown for the preparation of rac-90 below:

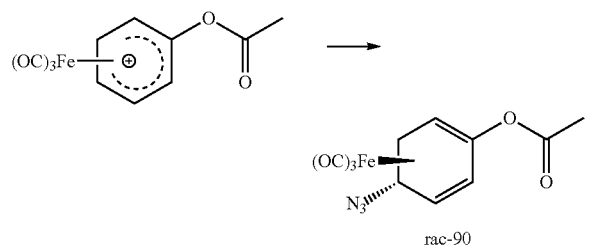

rac-90

In an embodiment of the present invention, an inventive complex can be prepared by providing an intermediate acyloxy- or phosphoryloxy-diene-Fe(CO)$_3$ complex substituted with a reactive functional group, and further reacting the intermediate acyloxy- or phosphoryloxy-diene-Fe(CO)$_3$ complex substituted with a reactive functional group to obtain an inventive complex. The reactive functional group with which the intermediate acyloxy- or phosphoryloxy-diene-Fe(CO)$_3$ complex is substituted can, for example, be an alkynyl, a carboxyl, a ketone, an aldehyde, an amino, an azido and/or a hydroxy group.

Examples of providing an intermediate acyloxy- or phosphoryloxy-diene-Fe(CO)$_3$ complex substituted with a reactive functional group, and further reacting the intermediate acyloxy- or phosphoryloxy-diene-Fe(CO)$_3$ complex substituted with a reactive functional group to obtain an inventive complex is the reaction of inventive complex rac-91 to inventive complex rac-94 and the reaction of inventive complex rac-90 to inventive complex rac-100 below:

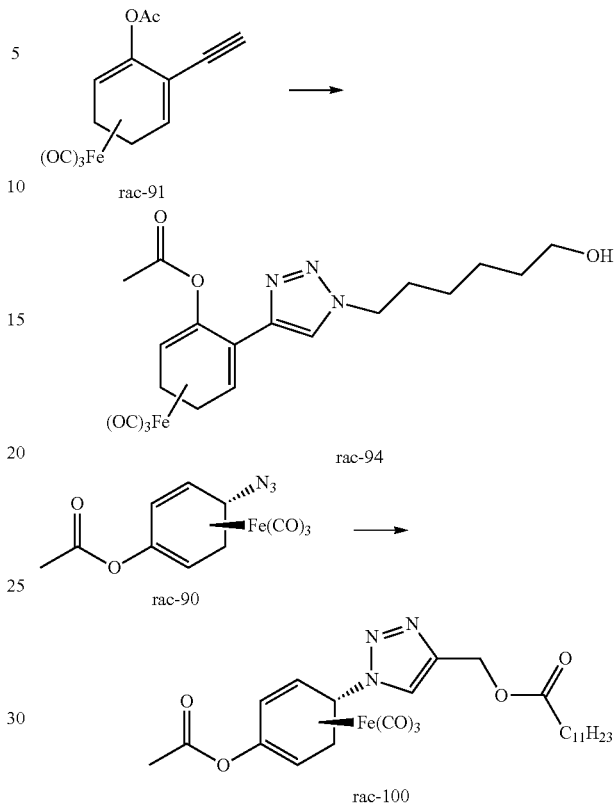

The present invention also provides a method of introducing carbon monoxide into a mammal as a physiologically effective agent. In an embodiment, the method includes providing a pharmaceutical composition for delivery of carbon monoxide to a physiological target comprising as an active ingredient at least one of the η$^4$-1,3-diene-Fe(CO)$_3$ complexes having the formula (I) as defined above, administering the pharmaceutical composition to an area of the mammal requiring treatment, and triggering a release of carbon monoxide by hydrolysis, wherein no complexes are specifically excluded from the η$^4$-1,3-diene-Fe(CO)$_3$ complexes having the formula (I) as defined above except for those having the formula (VI):

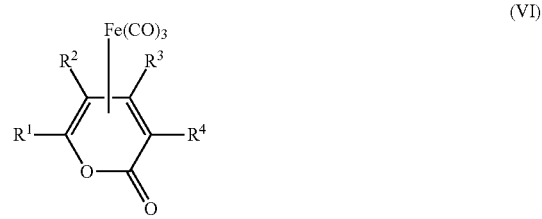

(VI)

wherein R$^1$, R$^2$, R$^3$ and R$^4$ are, with respect to complexes 37-46, as set forth in Table 5:

TABLE 5

| No. | R$^1$ | R$^2$ | R$^3$ | R$^4$ |
|---|---|---|---|---|
| 37 | H | H | H | H |
| 38 | CH$_3$ | H | Cl | H |
| 39 | CH$_3$ | H | CH$_3$ | H |
| 40 | CH$_3$ | H | I | H |

TABLE 5-continued

| No. | R¹ | R² | R³ | R⁴ |
|---|---|---|---|---|
| 41 | H | H | Cl | H |
| 42 | CH₃ | H | H | H |
| 43 | CH₃ | H | Br | H |
| 44 | H | Br | H | H |
| 45 | H | C₆H₅ | H | H |
| 46 | H | C₆H₅-4-OMe | H | H |

In an embodiment of the present invention, the hydrolysis can, for example, be triggered by a hydrolytic enzyme such as, for example, an esterase, a lipase, an amylase, a protease, a phosphatase and/or a phosphodiesterase.

In an embodiment of the present invention, the administering can, for example, be oral, intravenous, subcutaneous, transdermal, nasal, inhalatory, intermuscular, intraperitoneal and/or as a suppository.

The present invention also provides a method of treatment using a pharmaceutical composition for a mammal. In an embodiment, the method includes providing a pharmaceutical composition comprising as an active ingredient at least one of the $\eta^4$-1,3-diene-Fe(CO)$_3$ complexes having the formula (I) as defined above and administering the pharmaceutical composition to an area of the mammal requiring treatment. In an alternative embodiment, the method includes providing a pharmaceutical composition for delivery of carbon monoxide to a physiological target comprising as an active ingredient at least one of the $\eta^4$-1,3-diene-Fe(CO)$_3$ complexes having the formula (I) as defined above, administering the pharmaceutical composition to an area of a mammal requiring treatment, and triggering a release of carbon monoxide by hydrolysis in the area so as to treat the mammal, wherein no complexes are specifically excluded from the $\eta^4$-1,3-diene-Fe(CO)$_3$ complexes having the formula (I) as defined above except for those having the formula (VI):

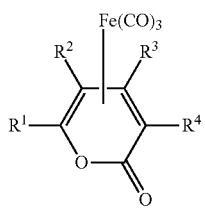

(VI)

wherein R¹, R², R³ and R⁴ are, with respect to complexes 37-46, as set forth in Table 5:

TABLE 5

| No. | R¹ | R² | R³ | R⁴ |
|---|---|---|---|---|
| 37 | H | H | H | H |
| 38 | CH₃ | H | Cl | H |
| 39 | CH₃ | H | CH₃ | H |
| 40 | CH₃ | H | I | H |
| 41 | H | H | Cl | H |
| 42 | CH₃ | H | H | H |
| 43 | CH₃ | H | Br | H |
| 44 | H | Br | H | H |
| 45 | H | C₆H₅ | H | H |
| 46 | H | C₆H₅-4-OMe | H | H |

In an embodiment of the present invention, the mammal can, for example, be a human.

In an embodiment of the present invention, the hydrolysis can be triggered by a hydrolytic enzyme such as, for example, an esterase, a lipase, an amylase, a protease, a phosphatase and/or a phosphodiesterase.

In an embodiment of the present invention, the administering can, for example, be oral, intravenous, subcutaneous, transdermal, nasal, inhalatory, intramuscular, intraperitoneal and/or as a suppository.

The pharmaceutical composition can comprise the inventive complex, a carrier, a buffer, a stabilizer or other materials well known to those skilled in the art. Such materials should be non-toxic and should not interfere unduly with the efficacy of the inventive complex. The precise nature of the carrier or other material may depend on the route of administration (for example, oral, intravenous, subcutaneous, transdermal, nasal, inhalatory, intramuscular, intraperitoneal and/or as a suppository).

The pharmaceutical composition for oral administration may, for example, be provided in tablet, capsule, powder or liquid form. A tablet may include a solid carrier such as gelatin or an adjuvant or slow-release polymer. The pharmaceutical composition in liquid form can, for example, include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Pharmaceutically acceptable amounts of other solvents may also be included, for example, where they are required for dissolving the particular inventive complex contained in the pharmaceutical composition.

For intravenous or subcutaneous injection, or injection of the pharmaceutical composition at the site of affliction, the inventive complex can, for example, be in the form of a parenterally acceptable solution which is pyrogen-free and has a suitable pH, isotonicity and stability. Those skilled in the art will be able to prepare suitable solutions using, for example, isotonic vehicles such as Sodium Chloride Injection, Ringer's Injection, and Lactated Ringer's Injection. Preservatives, stabilisers, buffers, antioxidants and/or other additives may be included as required. Delivery systems for needle-free injection are also known, and compositions for use with such systems may be prepared accordingly.

For a pharmaceutical composition intended for delivery by any route including but not limited to oral, intravenous, subcutaneous, transdermal, nasal, inhalatory, intramuscular, intraperitoneal and/or as a suppository, the inventive complexes may be microencapsulated within polymeric spheres such that exposure to body fluids and subsequent carbon monoxide release is delayed.

Administration of the pharmaceutical composition can occur, for example, in a prophylactically effective amount or a therapeutically effective amount sufficient to show benefits to the mammal, such as, for example, a human. The actual amount administered, and rate and time-course of administration, will depend on the nature and severity of what is being treated. Prescription of treatment, such as decisions on dosage, is within the responsibility of general practitioners and other medical doctors, and typically takes account of the disorder to be treated, the condition of the individual patient, the site of delivery, the method of administration and other factors known to practitioners.

In an embodiment of the present invention, the area to be treated can, for example, be an organ and/or tissue which is contained within the body of the mammal and not isolated from a blood supply, contained within the body of the mammal and isolated from a blood supply, and/or extracorporeal. The treatment can, for example, be used during the transplantation of an organ.

The term "organ" includes, for example, any anatomical part or member having a specific function in a mammal. Further included within the meaning of this term are substantial portions of organs, such as cohesive tissues obtained from an organ. Such organs include but are not limited to kidney, liver, heart, intestine, such as a large or small intestine, pancreas, and lungs. Further included in this definition are bones and blood vessels such as aortic transplants.

The term "transplantation" includes, for example, the process of implanting an organ, tissue, mass of cells, or individual cells into a patient. The term "transplantation" also includes the transfer of living tissues or cells from a donor to a recipient, with the intention of maintaining the functional integrity of the transplanted tissue or cells in the recipient. Transplantation can also include "cell transplantation," i.e., the process of transferring at least one cell, such as an islet cell(s), to a patient. For example, such transplantation can be performed by removing the beta cells (or intact islets) from a donor's pancreas and putting them into a recipient patient whose pancreas cannot produce sufficient insulin. The terms include all categories of transplants known in the art. Transplants are categorized by site and genetic relationship between donor and recipient. The term includes, for example, autotransplantation (removal and transfer of cells or tissue from one location on a patient to the same or another location on the same patient), allotransplantation (transplantation between members of the same species), and xenotransplantation (transplantations between members of different species).

The temperature at which the treatment is carried out can, for example, be between 15 and 37° C. for an organ which is contained within the body of the mammal and not isolated from a blood supply and/or an organ contained within the body of the mammal and isolated from a blood supply. The treatment can, for example, be carried out at between 2 and 4° C. for extracorporeal organs.

The amount of carbon monoxide delivered to the organ in the treatment can, for example, be an amount sufficient to enhance survival and/or function of the organ or tissue. The actual amount administered, and rate and time-course of administration, will depend on the nature of the organ.

In an embodiment of the present invention, the treatment can, for example, be for or to stimulate neurotransmission, stimulate vasodilation, hypertension, radiation damage, endotoxic shock, inflammation such as a vascular inflammation, an inflammatory-related disease such as rheumathoid arthritis, osteoarthritis, atherosclerosis, stroke, coronary disease, restenosis, pulmonary arterial hypertension and Alzheimer's disease, a hyperoxia-induced injury, apoptosis, cancer, organ transplant rejection and organ transplantation preservation such as for a liver, a kidney, a heart, a pancreas, a small intestine and skin, acute lung injury, acute kidney injury, acute liver injury, arteriosclerosis, post-ischemic organ damage, a myocardial infarction, chronic obstructive pulmonary disease (COPD), cardiovascular disease, heart failure, an angina, a hemorrhagic shock, a sepsis, an autoimmune neuroinflammation, sickle cell disease, diabetes, acute hepatitis, a colitis, a penile erectile dysfunction, asthma, emphysema, bronchitis, pneumonia, interstitial lung disease, an adult respiratory distress syndrome, a suffocation, a panic and related conditions such as the sensation of suffocation, Parkinson's disease and/or to promote wound healing. The treatment can, for example, include inhibiting a pro-inflammatory acting enzyme such as inducible nitric oxide synthase (iNOS) and/or a heme-containing enzyme such as NADPH oxidase.

The term "inflammation" is used to describe the fundamental pathological process consisting of a dynamic complex of cytologic and histologic reactions that occur in the affected blood vessels and adjacent tissues in response to an injury or abnormal stimulation caused by a physical, chemical or biological agent, including the local reactions and resulting morphologic changes, the destruction or removal of the injurious material, and the responses that lead to repair and healing. The so-called cardinal signs of inflammation are redness, heat, swelling, pain and, in certain cases, inhibited or lost function. The redness and warmth result from an increased amount of blood in the affected tissue, which is usually congested; swelling ordinarily occurs from the congestion and exudation; pressure on (or stretching of) nerve endings as well as changes in osmotic pressure and pH which may lead to significant pain; the disturbance in function may result in impairment in movement or the actual destruction of an anatomic part or organ. The term inflammation includes various types of inflammation such as acute, allergic, alternative (degenerative), atrophic, catarrhal (most frequently in the respiratory tract), croupous, fibrinopurulent, fibrinous, immune, hyperplastic or proliferative, subacute, serous and serofibrinous. Inflammation localized in the kidneys, liver, heart, skin, spleen, brain, kidney and pulmonary tract, especially the lungs, and that associated with sepsis or septic shock can be treated by the methods according to the present invention.

The term "cancer" is used as a general term to describe any of various types of malignant neoplasms, most of which invade surrounding tissues, may metastasize to several sites and are likely to recur after attempted removal and to cause death of the patient unless adequately treated. Cancers which may be treated using the present compositions and methods include, for example, stomach, colon, rectal, liver, pancreatic, lung, breast, cervix uteri, corpus uteri, ovary, prostate, testis, bladder, renal, brain/cns, head and neck, throat, Hodgkins disease, non-Hodgkins leukemia, skin melanoma, various sarcomas, small cell lung cancer, choriocarcinoma, mouth/pharynx, oesophagus, larynx, melanoma, kidney and lymphoma, among others.

The present invention also provides for a kit for producing a pharmaceutical solution. In an embodiment, the kit includes an inventive complex in solid form and a pharmaceutically acceptable solvent.

The term "pharmaceutically acceptable solvent" is used herein in the conventional sense to refer to a complex of solute, such as an inventive complex and the salt of the inventive complex, and solvent. If the solvent is water, the solvate may be referred to as a hydrate. Unless otherwise specified, a reference to a particular inventive complex also includes solvate forms thereof.

EXPERIMENTAL

Section I
General Experimental
Synthesis Procedures and Characteristic Data

Unless otherwise stated, all $^1$H and $^{13}$C NMR spectra were recorded at room temperature in $CDCl_3$ on Bruker instruments (Avance DPX 300, Avance DRX 500 or Avance II 600).

Chemical shifts (δ) are reported in parts per million (ppm) from tetramethylsilane using the residual solvent resonance as the internal standard ($CDCl_3$: 7.24 ppm for $^1$H NMR, 77.0 ppm for $^{13}$C NMR). Multiplicities are abbreviated as follows: s=singlet, d=doublet, t=triplet, q=quartet, m=multiplet, b=broad). A Ψ in front of the multiplet indicates a pseudo multiplicity. The $^{13}$C NMR signals of the Fe(CO)$_3$ carbon atoms could not be detected in some cases.

UV/V is spectra were recorded in phosphate buffer 0.1 M (pH=7.4) on a Beckmann Coulter DU 800 spectrometer (cell length 1 cm).

IR spectra were recorded on a Perkin-Elmer Paragon 1000 FT-IR spectrometer in the ATR mode at room temperature. Relative intensities of the signals are given as strong (s), medium (m), weak (w) and broad (b).

Mass spectra were recorded on Finnigan instruments (MAT Inocs 50 galaxy system (for EI) and a MAT 900 (for ESI and HR-MS). An Agilent Technologies Model GC 6890N gas chromatograph coupled with an HP 5973N series mass selective detector and an HP 7683 GC autosampler was employed for all GCMS analyses. Samples were separated on a 30-m×0.25-mm, HP-5 MS column. The column temperature was initially held at 50° C. for 2 min, then the temperature was raised to 300° C. at a rate of 25° C. per min and held for 5 min. The total run-time was 17 min. Injector temperature was maintained at 300° C., and the injection volume was 1.0 µL in the split mode. Mass spectra were scanned from m/z=35-500. Electron impact ionization energy was 70 eV.

Enantiomeric analyses through GC were performed on an Agilent (HP 6890) instrument with FID detection using either a BGB-176SE column (A) or a 6TBDMS-2,3-Me-β-CD column (B).

Enantiomeric analyses through High Performance Liquid Chromatography (HPLC) were conducted with HPLC instruments from Merck-Hitachi and Knauer (UV-detection at 220 nm and 254 nm) using one of the following columns: Diacel Chiracel OD-H (1), Diacel Chiracel OJ (2), Diacel Chiralpak AD-H (3), Macherey Nagel Nucleocell (4) and n-Hex/i-PrOH (99:1, 98:2 or 95:5) as a solvent.

CHN analyses were measured on an Elementar Vario EL machine.

X-ray crystal structure measurement was carried out with a Nonius KAPPA CCD instrument.

Structure solution was carried out with SHELXS97 and refinement with SHELXL97.

Melting points (uncorrected) were determined on a Büchi B-545 instrument.

Analytical TLC was carried out using precoated silica gel plates (Merck TLC plates silica gel 60F$_{254}$).

Flash column chromatography was performed using silica gel (particle size 40-63 mM, Acros).

All sensitive reactions were carried out in flame dried glassware under an argon atmosphere.

Chemicals were purchased from Merck, Sigma-Aldrich, Fluka, Acros, Lancaster or Strem and used without further purification.

Solvents were dried as follows: THF and Et$_2$O were distilled from sodium/benzophenone under an argon atmosphere. Methyl tert-butyl ether (MtBE) was distilled prior to use. Cyclohexenone was distilled and stored under argon. Acetic anhydride was shaken with P$_2$O$_5$ and K$_2$CO$_3$ prior to distillation under argon. Diisopropylamine was refluxed over KOH and stored on KOH. Trispyrrolidino-phosphoric acid triamide (TPPA, 98%), Lipase from *Candida rugosa* (>2 units/mg; 90860) and esterase from porcine liver (PLE, >130 units/mg; 46058) were purchased from Sigma-Aldrich. Complexes rac-13 (as described in A. Boháč, M. Lettrichová, P. Hrnčiac, M. Hutta, J.: Organomet. Chem., 507, pp 23-29 (1996); and in A. Boháč, M. Lettrichová, P. Hrnčiac: Synthesis, pp 881-882 (1991)), 2-methoxycyclohexa-1,3-dienetricarbonyliron (0) (as described in: M. C. P. Yeh, C.-C. Hwu: J. Organomet. Chem., 419, pg 341 (1991)), (R)-5-isopropyl-2-methylcyclohex-2-enone and (S)-5-isopropyl-2-methylcyclohex-2-enone (as described in: R. E. Ireland, P. Bey: Organic Syntheses, Coll. Vol. 6, pg 459 (1988); Vol. 53, pg 63 (1973)), 2-((trimethylsilyl)ethynyl)cyclohex-2-enone (as described in: W. Miller, C. R. Johnson: J. Org. Chem., 62, pg 1582 (1997)), 5,5-dimethylcyclohex-2-enone (as described in: K. Wińska, A. Grudniewska, A. Chojnacka, A. Bialońska, C. Wawrzeńczyk: Tetrahedron: Asymmetry, 21, pg 670 (2010)), L1 (as described in: K. E. Schulte, J. Reisch, A. Mock: Archiv der Pharmazie, 295, pg 645 (1962)) and (cyclohexa-1,5-dien-1-yloxy)trimethylsilane (as described in: M. C. P. Yeh, C.-C. Hwu: J. Organomet. Chem., 419, pg 341 (1991)) were prepared according to the literature procedures.

General Dienylester Formation Protocol I

To a solution of diisopropylamine in THF was added n-butyllithium at −78° C. After stirring the mixture for 10 min, a solution of the respective enone in THF was added dropwise (for approximately 1 h). Stirring was continued for 1 h at −78° C. The respective acid chloride or acid anhydride in THF was then added dropwise (for approximately 1 h). After 30 min at −78° C., the reaction mixture was allowed to warm to 25° C. before being quenched by addition of saturated aqueous NH$_4$Cl. After 10 min, the mixture was extracted with MtBE (50 mL) and the organic layer was washed with water (3×50 mL) and brine (50 mL) and dried over anhydrous MgSO$_4$. The solvent was then evaporated and the crude product purified.

Example 1

Preparation of Cyclohexa-1,5-dienyl acetate (L3)

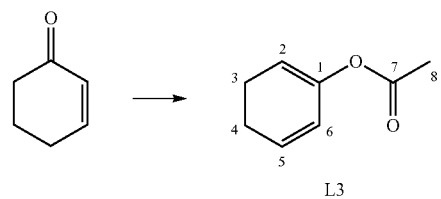

L3

Pursuant to Dienylester Formation Protocol I, diisopropylamine (2.6 mL, 18.4 mmol, 1.5 eq) and n-butyllithium (11.6 mL, 16.7 mmol, 1.3 eq, 1.44 M in hexane) in THF (12 mL) were reacted with a solution of cyclohex-2-enone (1.2 mL, 12.6 mmol, 1.0 eq) in THF (10 mL) and acetic anhydride (3.0 mL, 31.8 mmol, 2.5 eq) in THF (50 mL). The raw product was purified by column chromatography (silica gel, EtOAc/CyHex=1:20) to yield 990 mg (7.2 mmol, 57%) of the dienyl acetate L3 as a colorless oil.

TLC:R$_f$(CyHex/EtOAc=10:1)=0.54.

$^1$H NMR (500 MHz, CDCl$_3$): δ=5.85-5.82 (m, 1H, H5), 5.64-5.62 (m, 1H, H6), 5.30 (Ψbs, 1H, H2), 2.26-2.21 (m, 2H, H3), 2.16-2.14 (m, 2H, H4), 2.07 (s, 3H, H8).

$^{13}$C NMR (125 MHz, CDCl$_3$): δ=169.1 (C7), 145.6 (C1), 128.7 (C5), 122.9 (C6), 110.7 (C2), 21.7 (C4), 21.1 (C3), 20.7 (C8).

FT-IR (ATR): ṽ [cm$^{-1}$]=3080 (w, ν(C$_{sp2}$—H)), 2935 (w, ν(C$_{sp3}$—H)), 2875 (w, ν(C$_{sp3}$—H)), 2830 (w, ν(C$_{sp3}$—H)), 1751 (s, ν(C═O)), 1659 (m), 1426 (m), 1400 (m), 1367 (m), 1206 (s), 1137 (s), 1075 (m), 1009 (m), 951 (m), 908 (s), 864 (m), 825 (m), 725 (m), 692 (m).

LR-MS (GC-MS): m/z (%)=138 (18, [M]⁺), 96 (100, [M-(CH₂CO)]⁺), 67 (24), 43 (52).

Example 2

Preparation of Cyclohexa-1,5-dienyl pivalate (L8)

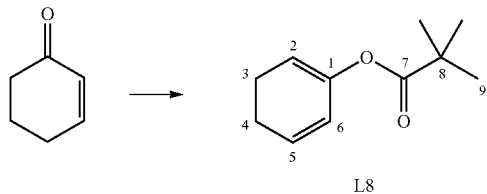

L8

Pursuant to Dienylester Formation Protocol I, diisopropylamine (1.2 mL, 8.7 mmol, 1.7 eq) and n-butyllithium (6.0 mL, 8.6 mmol, 1.7 eq, 1.44 M in hexane) in THF (8 mL) were reacted with a solution of cyclohex-2-enone (0.51 mL, 5.2 mmol, 1.0 eq) in THF (10 mL) and pivaloyl chloride (1.6 mL, 13.1 mmol, 2.5 eq) in THF (30 mL). The raw product was purified by column chromatography (silica gel, EtOAc/CyHex=1:20) to yield 448 mg (2.5 mmol, 48%) of dienyl pivalate L8 as a colorless oil.

TLC:R$_f$(CyHex/EtOAc=10:1)=0.43.

$^1$H NMR (300 MHz, CDCl₃): δ=5.86-5.80 (m, 1H, H5), 5.58 (Ψddd, J=1.8, 3.6, 10.0 Hz, 1H, H6), 5.27 (Ψbs, 1H, H2), 2.28-2.20 (m, 2H, H3), 2.17-2.10 (m, 2H, H4), 1.18 (s, 9H, H9).

$^{13}$C NMR (75 MHz, CDCl₃): δ=177.0 (C7), 145.9 (C1), 128.8 (C5), 123.1 (C6), 110.5 (C2), 38.7 (C8), 27.0 (C9), 21.9 (C4), 21.3 (C3).

FT-IR (ATR): $\tilde{\nu}$ [cm$^{-1}$]=3037 (w, ν(C$_{sp2}$—H)), 2970 (s, ν(C$_{sp3}$—H)), 2827 (m, ν(C$_{sp3}$—H)), 1747 (s, ν(C=O)), 1659 (m), 1479 (m), 1456 (m), 1425 (w), 1401 (m), 1364 (m), 1276 (s), 1232 (m), 1119 (bs), 1075 (m), 977 (w), 948 (m), 897 (m), 868 (w), 831 (w), 797 (w), 780 (m), 761 (m), 729 (m), 688 (w).

LR-MS (GC-MS): m/z (%)=180 (24, [M]⁺), 96 (100), 77 (14), 57 (73, [C(CH₃)₃]⁺), 41 (31).

Example 3

Preparation of Cholesta-2,4-dien-3-yl acetate (L14)

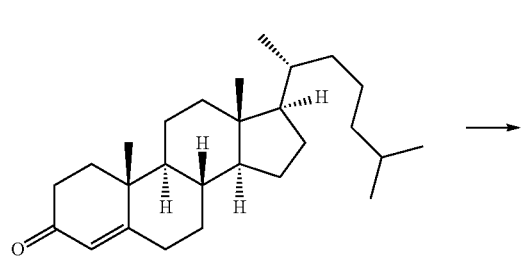

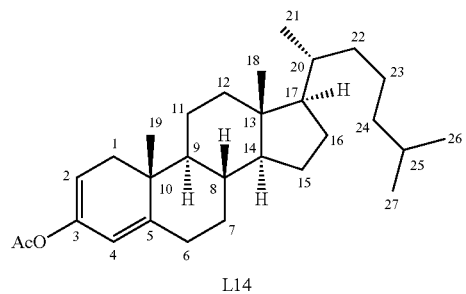

L14

Pursuant to Dienylester Formation Protocol I, diisopropylamine (0.86 mL, 6.13 mmol, 1.5 eq) and n-butyllithium (4.5 mL, 2.90 mmol, 1.40 eq, 1.56 M in hexane) in THF (16 mL) were reacted with a solution of cholestenone (1.73 g, 4.10 mmol, 1.00 eq) in THF (25 mL) and acetic anhydride (0.86 mL, 9.21 mmol, 2.20 eq) in THF (60 mL). The raw product was purified by column chromatography (silica gel, EtOAc/CyHex=1:8) to yield 1.23 g (2.88 mmol, 70%) of dienyl acetate L14 as a white solid.

TLC:R$_f$(CyHex/EtOAc=4:1)=0.8.

$^1$H-NMR (300 MHz, CDCl₃): δ=5.30 (t, J=2.0 Hz, 1H), 5.19-5.17 (m, 1H), 2.28-2.17 (m, 4H), 2.11 (s, 3H), 1.97 (dt, J=3.1, 12.4 Hz, 1H), 1.84-1.75 (m, 1H), 1.70-1.65 (m, 1H), 1.61-1.45 (m, 3H), 1.39-1.30 (m, 6H), 1.25-1.19 (m, 1H), 1.13-1.06 (m, 6H), 0.98 (s, 6H), 0.88 (d, J=6.6 Hz, 3H), 0.85 (d, J=1.3 Hz, 3H), 0.83 (d, J=1.3 Hz, 3H), 0.67 (s, 3H).

$^{13}$C-NMR (75 MHz, CDCl₃): δ=169.5 (COOCH₃), 149.8 (C$_q$), 144.9 (C$_q$), 115.5 (CH), 107.3 (CH), 56.2 (CH), 56.0 (CH), 54.5 (CH), 42.5 (C$_q$), 39.9 (CH₂), 39.5 (CH₂), 37.8 (C$_q$), 37.0 (CH₂), 36.3 (CH), 36.1 (CH₂), 35.8 (CH), 31.2 (CH₂), 31.1 (CH₂), 28.2 (CH₂), 28.0 (CH), 24.3 (CH₂), 23.8 (CH₂), 22.8 (CH₃), 22.6 (CH₃), 21.6 (CH₂), 21.0 (CH₃), 18.7 (CH₃), 17.2 (CH₃), 11.9 (CH₃).

FT-IR (ATR): ν [cm$^{-1}$]=2932 (m, ν(C$_{sp3}$—H)), 2869 (m, ν(C$_{sp3}$—H)), 1754 (m, ν(C=O)), 1505 (w), 1456 (m), 1367 (m), 1275 (m), 1217 (s), 1182 (m), 1171 (m), 1100 (w), 1027 (w), 912 (w), 875 (w), 749 (s), 700 (m).

LR-MS (GC-MS): m/z (%)=426 (10, [M]⁺), 384 (100, [M-(CH₂CO)]⁺), 370 (61), 355 (36), 257 (36), 247 (8), 229 (12), 215 (25), 201 (10), 189 (9), 175 (12), 161 (22), 147 (44), 135 (41), 122 (47), 107 (47), 95 (51), 81 (47), 67 (22), 55 (58), 43 (86).

T$_m$ (EtOH)=88.1° C.

Example 4

Preparation of (E)-Nona-1,3-dien-2-yl acetate (L7)

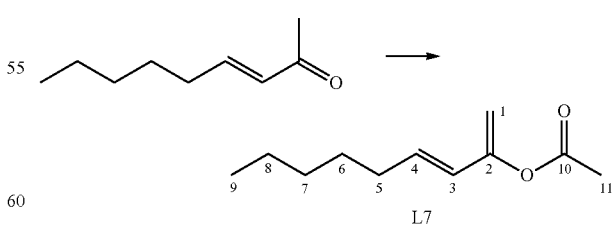

L7

Pursuant to Dienylester Formation Protocol I, diisopropylamine (2.6 mL, 18.4 mmol, 1.5 eq) and n-butyllithium (12.4 mL, 17.1 mmol, 1.4 eq, 1.38 M in hexane) in THF (12 mL) were reacted with a solution of (E)-non-3-en-2-one (2.1 mL, 12.6 mmol, 1.0 eq) in THF (10 mL) and acetic anhydride (2.6 mL, 27.6 mmol, 2.25 eq) in THF (50 mL). The raw product was purified by column chromatography (silica gel, EtOAc/CyHex=1:20) to yield 1.43 g (7.8 mmol, 62%) of the dienyl acetate L7 as a colorless oil.

TLC:$R_f$(CyHex/EtOAc=10:1)=0.5.

$^1$H-NMR (300 MHz, CDCl$_3$): δ=5.89 (Ψtd, J=1.2, 15.6 Hz, 1H, H3), 5.74-5.64 (m, 1H, H4), 4.81 (s, 1H, H1), 4.69 (s, 1H, H1), 2.14 (s, 3H, H11), 2.03 (Ψq, J=7.0 Hz, 2H, H5), 1.37-1.31 (m, 2H, H6), 1.26-1.22 (m, 4H, H7, H8), 0.82 (t, J=6.8 Hz, 3H, H9).

$^{13}$C-NMR (75 MHz, CDCl$_3$): δ=168.4 (C10), 151.7 (C2), 132.6 (C4), 123.8 (C3), 103.2 (C1), 32.0 (C5), 31.2 (C7), 28.4 (C6), 22.3 (C8), 20.6 (C11), 13.8 (C9).

FT-IR (ATR): $\tilde{v}$ [cm$^{-1}$]=3017 (w, ν(C$_{sp2}$—H)), 2962 (m, ν(C$_{sp3}$—H)), 2927 (s, ν(C$_{sp3}$—H)), 2853 (m, ν(C$_{sp3}$—H)), 1763 (s, ν(C═O)), 1657 (m), 1611 (m), 1456 (m), 1435 (m), 1368 (s), 1276 (w), 1194 (s), 1019 (s), 957 (s), 919 (w), 866 (m), 766 (w), 725 (w), 701 (w).

LR-MS (GC-MS): m/z (%)=182 (3, [M]$^+$), 140 (31, [M-(CH$_2$CO)]$^+$), 125 (8), 111 (6), 97 (32), 82 (19), 70 (47), 58 (51), 43 (100).

HR-MS (DIP-MS, EI, 70 eV): m/z 182.131±0.0007 (calculated: m/z 182.1307).

Example 5

Preparation of (E)-trimethyl(nona-1,3-dien-2-yloxy)silane

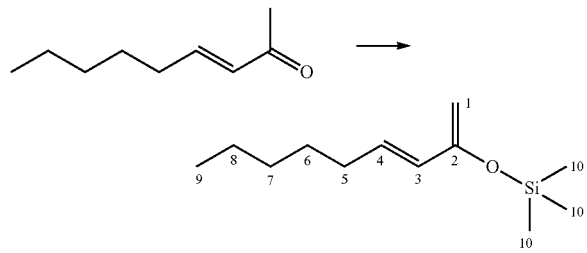

Pursuant to Dienylester Formation Protocol I, diisopropylamine (7.0 mL, 50.0 mmol, 1.4 eq) and n-butyllithium (32.4 mL, 46.5 mmol, 1.3 eq, 1.44 M in hexane) in THF (33 mL) were reacted with a solution of (E)-non-3-en-2-one (5.9 mL, 35.6 mmol, 1.0 eq) in THF (10 mL) and trimethylsilylchloride (8.0 mL, 62.6 mmol, 1.8 eq) in THF (30 mL). For the silylenolether, no aqueous workup was undertaken. n-Hexane (100 mL) was added to the reaction mixture, the residue filtered off and the solvent evaporated. The raw product was purified by distillation to yield 5.54 g (26.1 mmol, 74%) of (E)-trimethyl(nona-1,3-dien-2-yloxy)silane as a colorless oil.

$^1$H-NMR (300 MHz, CDCl$_3$): δ=5.98-5.82 (m, 2H, H3, H4), 4.20 (s, 2H, H1), 2.07 (Ψdd, J=6.7, 13.9 Hz, 2H, H5), 1.43-1.34 (m, 2H, H6), 1.33-1.23 (m, 4H, H7, H8), 0.87 (t, J=6.8 Hz, 3H, H9), 0.21 (s, 9H, Si(CH$_3$)$_3$).

$^{13}$C-NMR (75 MHz, CDCl$_3$): δ=155.0 (C2), 131.9 (C4), 127.5 (C3), 94.1 (C1), 32.1 (C5), 31.5 (C7), 28.9 (C6), 22.5 (C8), 14.0 (C9), 0.0 (Si(CH$_3$)$_3$).

FT-IR (ATR): $\tilde{v}$ [cm$^{-1}$]=3106 (w, ν(C$_{sp2}$—H)), 2953 (m, ν(C$_{sp3}$—H)), 2925 (m, ν(C$_{sp3}$—H)), 2853 (w, ν(C$_{sp3}$—H)), 1651 (m), 1590 (m), 1456 (m), 1373 (w), 1316 (s), 1250 (s), 1173 (w), 1123 (w), 1096 (w), 1017 (s), 961 (s), 962 (s), 847 (bs), 751 (s), 685 (m).

LR-MS (GC-MS): m/z (%)=212 (8, [M]$^+$), 197 (6, [M-(CH$_3$)]$^+$), 169 (6), 155 (5), 141 (100), 127 (5), 115 (4), 73 (22), 55 (5), 41 (8).

HR-MS (DIP-MS, EI, 70 eV): m/z 212.159±0.0008 (calculated: m/z 212.1596).

Example 6

Preparation of (E)-4-Phenylbuta-1,3-dien-2-yl acetate (L12)

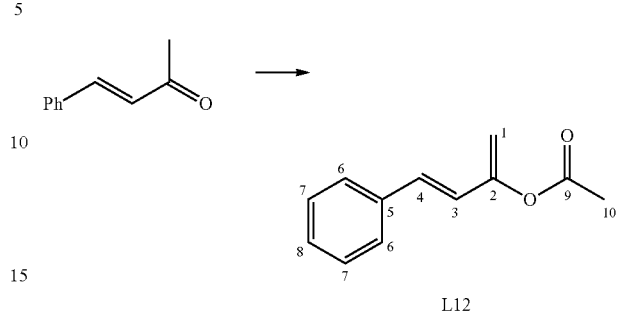

L12

Pursuant to Dienylester Formation Protocol I, diisopropylamine (2.6 mL, 18.4 mmol, 1.5 eq) and n-butyllithium (12.4 mL, 17.1 mmol, 1.4 eq, 1.38 M in hexane) in THF (12 mL) were reacted with a solution of (E)-phenylbut-3-en-2-one (1.85 g, 12.3 mmol, 1.0 eq) in THF (10 mL) and acetic anhydride (2.6 mL, 31.8 mmol, 2.25 eq) in THF (50 mL). The raw product was purified by column chromatography (silica gel, EtOAc/CyHex=1:20) to yield 1.50 g (7.9 mmol, 65%) of dienyl acetate L12 as a colorless oil.

TLC:$R_f$(CyHex/EtOAc=10:1)=0.29.

$^1$H-NMR (300 MHz, CDCl$_3$): δ=7.41-7.38 (m, 2H, CH$_{ar}$), 7.34-7.23 (m, 2H, CH$_{ar}$), 7.28-7.24 (m, 1H, CH$_{ar}$), 6.65 (d, J=16.0 Hz, 1H, H3), 6.58 (d, J=16.0 Hz, 1H, H4), 5.12 (Ψd, J=1.6 Hz, 1H, H1), 4.97 (Pd, J=1.6 Hz, 1H, H1), 2.29 (s, 3H, H10).

$^{13}$C-NMR (75 MHz, CDCl$_3$): δ=168.7 (C9), 151.8 (C2), 135.9 (C5), 129.8 (C4), 128.8 (CH$_{ar}$), 128.2 (CH$_{ar}$), 127.8 (CH$_{ar}$), 122.5 (C3), 106.1 (C1), 20.9 (C10).

FT-IR (ATR): $\tilde{v}$ [cm$^{-1}$]=3086 (w, ν(C$_{sp2}$—H)), 3053 (w, ν(C$_{sp2}$—H)), 3013 (w, ν(C$_{sp2}$—H)), 1760 (s, ν(C═O)), 1640 (m), 1603 (w), 1490 (w), 1448 (w), 1369 (m), 1290 (w), 1196 (s), 1126 (w), 1073 (w), 1020 (m), 958 (m), 933 (w), 872 (w), 754 (m), 692 (m).

LR-MS (GC-MS): m/z (%)=188 (12, [M]$^+$), 146 (100, [M-(CH$_2$CO)]$^+$), 131 (31), 117 (32), 103 (17), 91 (15), 77 (20), 43 (41).

HR-MS (DIP-MS, 70 eV): m/z 188.083±0.0008 (calculated: m/z 188.0837).

$T_m$ (DCM)=27° C.

Example 7

Preparation of (S)-3-isopropyl-6-methylcyclohexadienyl acetate (L9)

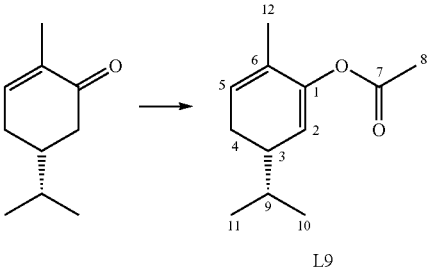

L9

Pursuant to Dienylester Formation Protocol I, diisopropylamine (1.1 mL, 18.4 mmol, 1.5 eq) and n-butyllithium (5.3 mL, 7.4 mmol, 1.4 eq, 1.39 M in hexane) in THF (12 mL) were reacted with a solution of (R)-5-isopropyl-2-methylcyclohex-2-enone (731 mg, 4.8 mmol, 1.0 eq) in THF (10 mL) and acetic anhydride (1.1 mL, 28.3 mmol, 2.25 eq) in THF (50 mL). The raw product was purified by column chromatography (silica gel, EtOAc/CyHex=1:40) to yield 536 mg (2.8 mmol, 58%) of dienyl acetate L9 as a colorless oil.

TLC: $R_f$(CyHex/EtOAc=10:1)=0.6.

$^1$H-NMR (300 MHz, CDCl$_3$): δ=5.58 (Ψbs, 1H, H5), 5.28 (d, J=3.6 Hz, 1H, H2), 2.36-2.22 (m, 1H, H3), 2.14 (s, 3H, H8), 1.6-1.58 (m, 1H, H9), 1.61 (Ψd, J=1.4 Hz, 3H, H12), 1.23 (Ψbs, 2H, H4), 0.89 (d, J=4.3 Hz, 3H, H10/H11), 0.87 (d, J=4.3 Hz, 3H, H10/H11).

$^{13}$C-NMR (75 MHz, CDCl$_3$): δ=169.6 (C7), 147.1 (C1), 128.8 (C6), 124.6 (C5), 115.8 (C2), 39.9 (C3), 31.4 (C9), 29.7 (C4), 20.7 (C8), 19.9 (C10/C11), 19.7 (C10/C11), 16.6 (C12).

LR-MS (GC-MS): m/z (%)=194 (5, [M]$^+$), 151 (4), 109 (100), 91 (13), 79 (14), 63 (4), 43 (35).

Example 8

Preparation of (R)-3-isopropyl-6-methylcyclohexa-1,5-dien-1-yl acetate (L10)

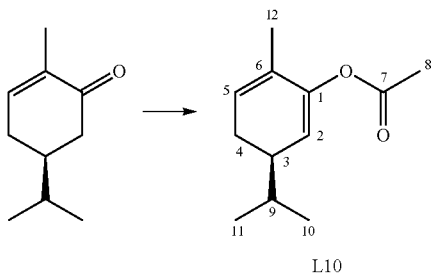

L10

Pursuant to Dienylester Formation Protocol I, diisopropylamine (2.6 mL, 18.4 mmol, 1.5 eq) and n-butyllithium (11.6 mL, 16.7 mmol, 1.3 eq, 1.44 M in hexane) in THF (12 mL) were reacted with a solution of (S)-5-isopropyl-2-methylcyclohex-2-enone (1.92 g, 12.6 mmol, 1.0 eq) in THF (10 mL) and acetic anhydride (3.0 mL, 31.8 mmol, 2.5 eq) in THF (50 mL). The raw product was purified by column chromatography (silica gel, EtOAc/CyHex=1:20) to yield 1.17 g (6.0 mmol, 48%) of dienyl acetate L10 as a colorless oil.

TLC: $R_f$(CyHex/EtOAc=10:1)=0.6.

LR-MS (GC-MS): m/z (%)=194 (19, [M]$^+$), 151 (19), 109 (100), 91 (20), 79 (16), 65 (7), 43 (30).

Example 9

Preparation of 3,3-dimethylcyclohexa-1,5-dien-1-yl acetate (L5)

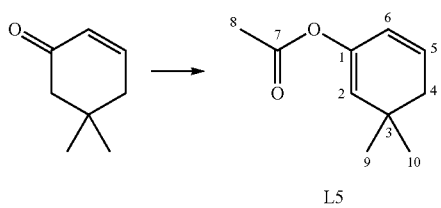

L5

Pursuant to Dienylester Formation Protocol I, diisopropylamine (2.6 mL, 18.4 mmol, 1.5 eq) and n-butyllithium (11.6 mL, 16.7 mmol, 1.3 eq, 1.44 M in hexane) in THF (12 mL) were reacted with a solution of 5,5-dimethylcyclohex-2-enone (1.561 g, 12.6 mmol, 1.0 eq) in THF (10 mL) and acetic anhydride (3.0 mL, 31.8 mmol, 2.5 eq) in THF (50 mL). The raw product was purified by column chromatography (silica gel, EtOAc/CyHex=1:10) to yield 1.361 g (8.1 mmol, 65%) of dienyl acetate L5 as a colorless oil.

TLC: $R_f$(CyHex/EtOAc=5:1)=0.61.

$^1$H NMR (300 MHz, CDCl$_3$): δ=5.83-5.74 (m, 1H, H6), 5.66 (ddd, J=9.9, 3.7, 1.9 Hz, 1H, H5), 5.10 (Ψd, J=1.7 Hz, 1H, H2), 2.12 (Ψdd, J=4.3, 1.9 Hz, 2H, H4), 2.10 (s, 3H, H8), 1.02 (s, 6H, H9, H10).

$^{13}$C NMR (75 MHz, CDCl$_3$): δ=169.2 (C7), 144.4 (C1), 127.7 (C6), 122.0 (C5), 121.9 (C2), 37.5 (C4), 31.7 (C3), 28.1 (C9, C10), 21.0 (C8).

FT-IR (ATR): $\tilde{v}$ [cm$^{-1}$]=2955 (m, ν(C$_{sp3}$—H)), 2923 (m, ν(C$_{sp3}$—H)), 2865 (w, ν(C$_{sp3}$—H)), 1759 (s, ν(C=O)), 1659 (m), 1464 (m), 1400 (m), 1368 (s), 1212 (s), 1196 (s), 1112 (s), 1044 (w), 1009 (m), 1001 (m), 948 (w), 910 (m), 899 (m), 874 (w), 835 (m), 729 (w), 703 (w).

LR-MS (GC-MS): m/z (%)=166 (9, [M]$^+$), 124 (10, [M-(CH$_2$CO)]$^+$), 109 (100), 91 (9), 79 (10), 68 (8), 43 (20).

Example 10

Preparation of 6-((trimethylsilyl)ethynyl)cyclohexa-1,5-dien-1-yl acetate (L6)

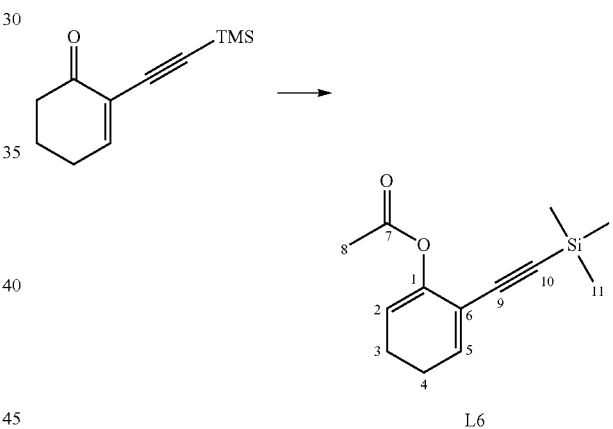

L6

Pursuant to Dienylester Formation Protocol I, diisopropylamine (2.6 mL, 18.4 mmol, 1.5 eq) and n-butyllithium (11.6 mL, 16.7 mmol, 1.3 eq, 1.44 M in hexane) in THF (12 mL) were reacted with a solution of 2-((trimethylsilyl)ethynyl)cyclohex-2-enone (2.42 g, 12.6 mmol, 1.0 eq) in THF (10 mL) and acetic anhydride (3.0 mL, 31.8 mmol, 2.5 eq) in THF (50 mL). The raw product was purified by column chromatography (silica gel, EtOAc/CyHex=1:10) to yield 1.69 g (7.2 mmol, 57%) of dienyl acetate L6 as a colorless oil.

TLC: $R_f$(CyHex/EtOAc=5:1)=0.52.

$^1$H NMR (300 MHz, CDCl$_3$): δ=6.30 (Ψbs, 1H, H5), 5.42 (Ψbs, 1H, H2), 2.31-2.22 (m, 4H, H3, H4), 2.15 (s, 3H, H8), 0.14 (s, 9H, H11).

$^{13}$C NMR (75 MHz, CDCl$_3$): δ=169.2 (C7), 143.5 (C1), 136.6 (C5), 118.4 (C6), 112.8 (C2), 100.2 (C9), 95.2 (C10), 22.6 (C3/C4), 20.8 (C3/C4), 20.6 (C8), −0.16 (C11).

FT-IR (ATR): $\tilde{v}$ [cm$^{-1}$]=2957 (m, ν(C$_{sp3}$—H)), 2893 (m, ν(C$_{sp3}$—H)), 2829 (w, ν(C$_{sp3}$—H)), 2151 (m), 1762 (s, ν(C=O)), 1650 (w), 1424 (w), 1364 (m), 1248 (s), 1204 (bs), 1110 (m), 1082 (m), 1006 (m), 981 (w), 917 (m), 834 (bs), 758 (s), 699 (m).

LR-MS (GC-MS): m/z (%)=234 (4, [M]⁺), 219 (3), 192 (29, [M-(OCC(CH₃)₃—H)]⁺), 177 (20), 149 (9), 107 (5), 73 (12), 43 (100).

Example 11

Preparation of 3-oxocyclohex-1-en-1-yl pivalate

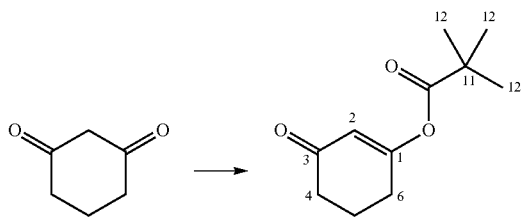

A solution of cyclohexa-1,3-dion (4.00 g, 35.6 mmol, 1.0 eq) and pyridine (5.8 ml, 71.4 mmol, 2.0 eq) in DCM (80 mL) was cooled to 0° C. Pivaloylchloride (6.6 mL, 53.6 mmol, 1.5 eq) was added dropwise and the reaction mixture was stirred (for approximately 1 h). Water was then added, the phases separated and the aqueous phase extracted with DCM. The combined organic phases were dried over anhydrous MgSO₄, the solvent was evaporated and the raw product was purified by column chromatography (silica gel, EtOAc/CyHex=1:3) to yield 11.5 g (29.2 mmol, 82%) of 3-oxocyclohex-1-en-1-yl pivalate as a yellow oil.

TLC:$R_f$(CyHex/EtOAc=1:1)=0.78.

¹H NMR (300 MHz, CDCl₃): δ=5.80 (s, 1H, H2), 2.46 (t, J=6.1 Hz, 2H, H6), 2.35 (t, J=6.7 Hz, 2H, H4), 2.08-1.93 (Ψq, J=6.4 Hz, 2H, H5), 1.22 (s, 9H, H9).

¹³C NMR (75 MHz, CDCl₃): δ=199.4 (C3), 175.1 (C7), 170.3 (C1), 117.4 (C2), 39.2 (C8), 36.6 (C4), 28.1 (C6), 26.8 (C9), 21.2 (C5).

FT-IR (ATR): $\tilde{\nu}$ [cm⁻¹]=2971 (m, ν($C_{sp3}$—H)), 2874 (m, ν($C_{sp3}$—H)), 1748 (s, ν(C=O)), 1681 (s), 1642 (s), 1479 (s), 1456 (m), 1427 (m), 1396 (m), 1363 (s), 1344 (m), 1325 (9), 1303 (m), 1271 (s), 1229 (m), 1140 (s), 1116 (bs), 1075 (s), 1025 (s), 965 (s), 941 (m), 906 (m), 878 (w), 831 (w), 789 (w), 754 (m), 662 (m).

LR-MS (GC-MS): m/z (%)=196 (1, [M]⁺), 153 (3), 125 (4), 113 (35), 96 (4), 85 (71), 83 (43), 69 (21), 57 (100).

Example 12

Preparation of Cyclohexa-1,3-diene-1,3-diyl bis(2,2-dimethylpropanoate) (L11)

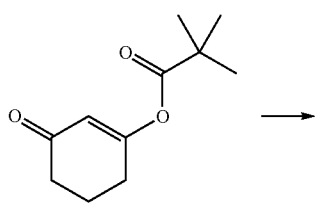

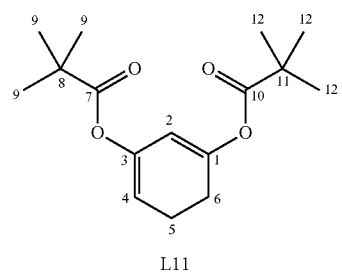

Pursuant to Dienylester Formation Protocol I, diisopropylamine (1.2 mL, 8.7 mmol, 1.7 eq) and n-butyllithium (6.0 mL, 8.6 mmol, 1.7 eq, 1.44 M in hexane) in THF (8 mL) were reacted with a solution of cyclohex-2-enone (1.02 g, 5.2 mmol, 1.0 eq) in THF (10 mL) and pivaloyl chloride (1.6 mL, 13.1 mmol, 2.5 eq) in THF (30 mL). The raw product was purified by column chromatography (silica gel, EtOAc/CyHex=1:5) to yield a raw product containing approximately 583 mg (2.08 mmol, 40%) of diene L11 as a yellow oil. L11 was used for further transformations without additional purification.

LR-MS (GC-MS): m/z (%)=280 (4, [M]⁺), 196 (10), 112 (39), 85 (10), 57 (100), 41 (22) 77 (14), 57 (73, [C(CH₃)₃]⁺), 41 (31).

General Dienylester Formation Protocol II

To a solution of hexamethyldisilazane in THF was added n-butyllithium at −78° C. After 10 min, TPPA was added and stirring was continued (for approximately 20) min at −78° C. The respective enone in THF was then added dropwise (for approximately 1 h). After another hour at −78° C., the respective acid chloride or acid anhydride in THF was added dropwise (for approximately 1 h). The mixture was stirred (for approximately 30 min) at −78° C. and then allowed to warm to 25° C. before being quenched with saturated aqueous NH₄Cl. After extraction with MtBE (50 mL), the organic solution was washed with water (3×50 mL) and brine (50 mL) and dried over anhydrous MgSO₄. The solvent was then evaporated and the crude product purified by column chromatography.

Example 13

Preparation of Cyclohexa-1,3-dienyl acetate (L2)

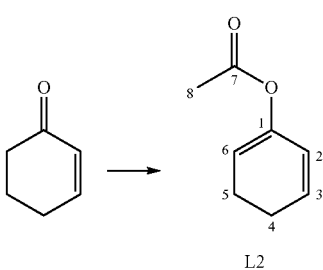

Pursuant to Dienylester Formation Protocol II, hexamethyldisilazane (2.6 mL, 12.1 mmol, 1.5 eq), n-butyllithium (7.3 mL, 10.5 mmol, 1.3 eq, 1.44 M in hexane) and TPPA (5.0 mL, 18 mmol, 2.5 eq) in THF (100 mL) were reacted with a solution of cyclohex-2-enone (0.8 mL, 8.1 mmol, 1.0 eq) in THF (10 mL) and acetic anhydride (1.8 mL, 18.4 mmol, 2.27 eq) in THF (50 mL). The raw product was purified by column chromatography (silica gel, EtOAc/CyHex=1:20) to yield 731 mg (5.3 mmol, 65%) of dienyl acetate L2 as a colorless oil.

TLC:$R_f$(CyHex/EtOAc=10:1)=0.54.

$^1$H NMR (500 MHz, CDCl$_3$): δ=5.84-5.81 (m, 1H, H3), 5.63-5.59 (m, 2H, H2, H4), 2.33 (Ψbs, 4H, H5, H6), 2.11 (s, 3H, H8).

$^{13}$C NMR (125 MHz, CDCl$_3$): δ=169.0 (C7), 149.1 (C1), 123.5 (C4), 122.7 (C3), 110.9 (C2), 25.4 (C6), 23.6 (C5), 21.0 (C8).

FT-IR (ATR): ṽ[cm$^{-1}$]=3045 (w, ν(C$_{sp2}$—H)), 2932 (m, ν(C$_{sp3}$—H)), 2871 (m, ν(C$_{sp3}$—H)), 1755 (s, ν(C═O)), 1665 (w), 1593 (w), 1495 (w), 1365 (m), 1205 (s), 1137 (m), 1010 (m), 912 (s), 747 (s), 692 (m).

LR-MS (GC-MS): m/z (%)=138 (17, [M]$^+$), 96 (100, [M-(CH$_2$CO)]$^+$), 79 (60), 67 (44), 54 (29), 43 (50).

Example 14

Preparation of Cyclohexa-1,3-dienyl pivalate (L13)

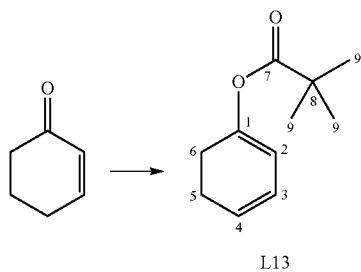

L13

Pursuant to Dienylester Formation Protocol II, hexamethyldisilazane (2.6 mL, 12.1 mmol, 1.5 eq), n-butyllithium (7.3 mL, 10.5 mmol, 1.3 eq, 1.44 M in hexane) and TPPA (5.0 mL, 18 mmol, 2.5 eq) in THF (100 mL) were reacted with a solution of cyclohex-2-enone (0.8 mL, 8.1 mmol, 1.0 eq) in THF (10 mL) and pivaloylchloride (2.2 mL, 2.22 g, 18.4 mmol, 2.27 eq) in THF (50 mL). The raw product was purified by column chromatography (silica gel, EtOAc/CyHex=1:20) to yield 900 mg (5.0 mmol, 62%) of dienylpivalate L13 as a colorless oil.

$^1$H NMR (500 MHz, CDCl$_3$): δ=5.94-5.77 (m, 1H, H3), 5.70-5.51 (m, 2H, H2, H4), 2.43-2.21 (m, 4H, H5, H6), 1.23 (s, 9H, H9).

$^{13}$C NMR (125 MHz, CDCl$_3$): δ=176.7 (C7), 149.4 (C1), 123.3 (C3/C4), 122.9 (C3/C4), 110.6 (C2), 38.9 (C8), 27.0 (C9), 25.3 (C5/C6), 23.6 (C5/C6).

LR-MS (GC-MS): m/z (%)=180 (10, [M]$^+$), 96 (98), 79 (12), 67 (15), 57 (100, [C(CH$_3$)$_3$]$^+$), 41 (47).

Example 15

Preparation of 5,5-dimethylcyclohexa-1,3-dien-1-yl acetate (L4)

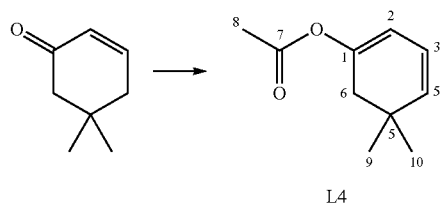

L4

Pursuant to Dienylester Formation Protocol II, hexamethyldisilazane (2.6 mL, 12.1 mmol, 1.5 eq), n-butyllithium (7.3 mL, 10.5 mmol, 1.3 eq, 1.44 M in hexane) and TPPA (5.0 mL, 18 mmol, 2.5 eq) in THF (100 mL) were reacted with a solution of 5,5-dimethylcyclohex-2-enone (1.00 g, 8.1 mmol, 1.0 eq) in THF (10 mL) and acetic anhydride (1.8 mL, 18.4 mmol, 2.27 eq) in THF (50 mL). The raw product was purified by column chromatography (silica gel, EtOAc/CyHex=1:20) to yield 881 mg (5.3 mmol, 65%) of dienyl acetate L4 as a colorless oil.

TLC:$R_f$(CyHex/EtOAc=5:1)=0.58.

$^1$H NMR (300 MHz, CDCl$_3$): δ=5.70 (dd, J=9.4, 5.8 Hz, 1H, H3), 5.57 (d, J=5.8 Hz, 1H, H4), 5.37 (d, J=9.4 Hz, 1H, H2), 2.22 (Ψd, J=1.1 Hz, 2H, H6), 2.11 (s, 3H, H8), 1.04 (s, 6H, H9, H10).

$^{13}$C NMR (75 MHz, CDCl$_3$): δ=169.0 (C7), 148.7 (C1), 135.2 (C2), 119.8 (C3), 109.6 (C4), 40.3 (C6), 33.8 (C5), 27.9 (C9, C10), 21.0 (C8).

FT-IR (ATR): ṽ [cm$^{-1}$]=2946 (m, ν(C$_{sp3}$—H)), 2920 (s, ν(C$_{sp3}$—H)), 2851 (m, ν(C$_{sp3}$—H)), 1756 (s, ν(C═O)), 1673 (w), 1593 (w), 1464 (w), 1366 (m), 1209 (s), 1117 (s), 1066 (w), 1011 (m), 802 (w), 727 (w).

LR-MS (GC-MS): m/z (%)=166 (17, [M]$^+$), 124 (26, [M-(CH$_2$CO)]$^+$), 109 (100), 91 (9), 79 (10), 43 (25).

General Complexation Protocol for Preparation of Diene-Fe(CO)$_3$ Complexes

A Schlenk tube was charged with the diene and Fe$_2$(CO)$_9$ and set under argon by three evacuation/argon flush cycles. Degassed diethylether was then added and the reaction mixture was heated to reflux under argon. The solvent was then evaporated and the crude mixture purified by column chromatography (silica gel, EtOAc/CyHex=1:40, if not otherwise stated) to yield the complex.

Example 16

Preparation of (RS)-[η$^4$-Cyclohexa-1,5-dien-1-yl-tricarbonyliron(0)]acetate (rac-86)

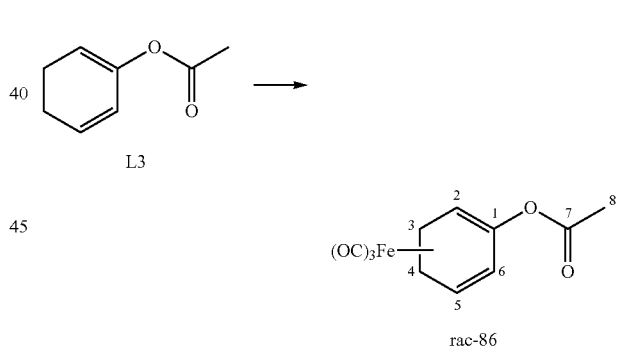

rac-86

Pursuant to the General Complexation Protocol, diene L3 (500 mg, 3.6 mmol, 1.0 eq) and Fe$_2$(CO)$_9$ (3.90 g, 10.7 mmol, 3.0 eq) were heated in Et$_2$O (30 mL) for 16 h. After purification, 687 mg (2.5 mmol, 69%) of inventive complex rac-86 were isolated as a yellow oil.

TLC:$R_f$(CyHex/EtOAc=10:1)=0.51.

$^1$H NMR (500 MHz, CDCl$_3$): δ=5.49 (Ψdd, J=1.9, 6.6, 1H, H6), 3.34 (Ψtd, J=2.3, 4.5 Hz, 1H, H2), 2.83 (dt, J=3.0, 6.30 Hz, 1H, H5), 2.17 (s, 3H, H8), 1.86-1.67 (m, 2H, H3), 1.6-1.50 (m, 2H, H4).

$^{13}$C NMR (125 MHz, CDCl$_3$): δ=210.8 (Fe(CO)$_3$), 170.1 (C7), 128.2 (C1), 79.8 (C6), 59.0 (C2), 52.0 (C5), 24.5 (C3), 23.4 (C4), 21.0 (C8).

FT-IR (ATR): ṽ [cm$^{-1}$]=2921 (w, ν(C$_{sp3}$—H)), 2839 (w, ν(C$_{sp3}$—H)), 2047 (s, ν(Fe(CO)$_3$)), 1967 (bs, ν(Fe(CO)$_3$)), 1764 (s, ν(C═O)), 1452 (m), 1428 (m), 1367 (m), 1206 (s), 1170 (s), 1123 (w), 1085 (w), 1011 (w), 899 (w).

Example 17

Preparation of (RS)-[θ⁴-Cyclohexa-1,3-dien-1-yl-tricarbonyliron(0)]acetate (rac-96)

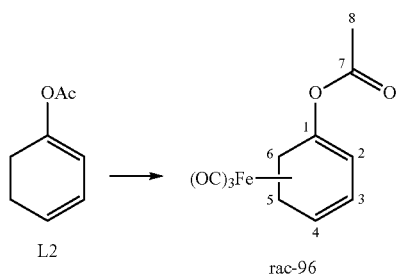

Pursuant to the General Complexation Protocol, diene L2 (800 mg, 5.8 mmol, 1.0 eq) and Fe₂(CO)₉ (6.30 g, 17.1 mmol, 3.0 eq) were heated in Et₂O (50 mL) for 16 h. After purification, 1.258 g (4.6 mmol, 79%) of inventive complex rac-96 were isolated as a yellow crystalline solid.

TLC: $R_f$(CyHex/EtOAc=10:1)=0.51.

¹H NMR (500 MHz, CDCl₃): δ=5.36 (d, J=4.2 Hz, 1H, H2), 3.34 (t, J=5.0 Hz, 1H, H3), 3.08-3.06 (m, 1H, H4), 2.17-1.62 (m, 4H, H5, H6), 2.17 (s, 3H, H8).

¹³C NMR (125 MHz, CDCl₃): δ=169.2 (C7), 103.3 (C1), 80.6 (C2), 80.3 (C3), 60.3 (C4), 24.5 (C5/C6), 23.4 (C5/C6), 21.2 (C8).

FT-IR (ATR): ṽ [cm⁻¹]=2929 (m, ν($C_{sp3}$—H)), 2852 (m, ν($C_{sp3}$—H)), 2047 (s, ν(Fe(CO)₃)), 1967 (bs, ν(Fe(CO)₃)), 1751 (s, ν(C=O)), 1470 (m), 1427 (m), 1366 (s), 1328 (m), 1266 (m), 1209 (s), 1180 (m), 1014 (m), 909 (m), 890 (m), 865 (w), 759 (m).

LR-MS (DIP-MS, 70 eV): m/z (%)=278 (1, [M]⁺), 250 (15, [M-CO]⁺), 222 (34, [M-2CO]⁺¹, ¹⁹⁴ (35, [M-3CO]⁺]), 192 (100), 164 (11), 150 (19), 134 (20), 121 (10), 56 (26, [Fe]⁺).

HR-MS (DIP-MS, 70 eV): m/z 277.9883±0.0005 (calculated ([M]⁺) m/z 277.9878).

EA: Calculated for C₁₁H₁₀FeO₅: C, 47.52; H, 3.63. Found: C, 48.09; H, 3.80.

$T_m$ (DCM)=53.2° C.

Example 18

Preparation of (RS)-[η⁴-Cyclohexa-1,5-dien-1-yl-tricarbonyliron(0)] pivalate (rac-87)

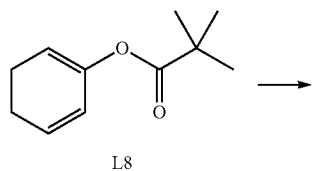

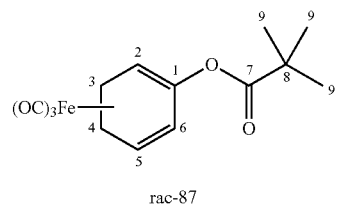

Pursuant to the General Complexation Protocol, diene L8 (500 mg, 2.8 mmol, 1.0 eq) and Fe₂(CO)₉ (2.0 g, 5.5 mmol, 2.0 eq) were heated in Et₂O (30 mL) for 16 h. After purification, 699 mg (2.2 mmol, 78%) of inventive complex rac-87 were isolated as a yellow oil.

TLC: $R_f$(CyHex/EtOAc=10:1)=0.78.

¹H NMR (600 MHz, CDCl₃): δ=5.47 (Ψdd, J=1.5, 6.6 Hz, 1H, H6), 3.31 (Ψtd, J=2.2, 4.08 Hz, 1H, H2), 2.82 (td, J=3.0, 6.2 Hz, 1H, H5), 1.85-1.79 (m, 1H, H3), 1.77-1.71 (m, 1H, H3), 1.58-1.50 (m, 2H, H4), 1.242 (s, 9H, H9).

¹³C NMR (150 MHz, CDCl₃): δ=210.8 (Fe(CO)₃), 177.9 (C7), 128.8 (C1), 79.3 (C6), 59.4 (C2), 51.8 (C5), 39.1 (C8), 26.9 (C9), 24.6 (C3), 23.5 (C4).

FT-IR (ATR): ṽ [cm⁻¹]=2970 (m, ν($C_{sp3}$—H)), 2950 (m, ν($C_{sp3}$—H)), 2900 (m, ν($C_{sp3}$—H)), 2042 (s, ν(Fe(CO)₃)), 1965 (bs, ν(Fe(CO)₃)), 1750 (s, ν(C=O)), 1457 (m), 1428 (m), 1396 (m), 1275 (m), 1171 (s), 1108 (s), 1022 (m), 885 (m), 759 (w), 672 (m).

LR-MS (DIP-MS, 70 eV): m/z (%)=292 (1, [M-CO]⁺), 264 (21, [M-2CO]⁺], 236 (17, [M-3CO]⁺), 234 (100), 149 (32), 134 (60), 121 (10), 95 (15), 84 (14), 71 (7), 57 (40, [C(CH₃)₃]⁺), 56 (30, [Fe]⁺).

HR-MS (DIP-MS, 70 eV): m/z 292.040±0.0012 (calculated ([M-CO]⁺): m/z 292.0398).

EA: Calculated for C₁₄H₁₆FeO₅: C, 52.53; H, 5.04. Found: C, 53.08; H, 5.19.

Example 19

Preparation of (RS)-[η⁴-3,3-dimethylcyclohexa-1,5-dien-1-yl-tricarbonyliron(0)]acetate (rac-85)

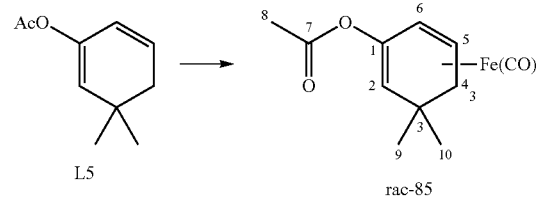

Pursuant to the General Complexation Protocol, diene L5 (500 mg, 3.01 mmol, 1.0 eq) and Fe₂(CO)₉ (2.75 g, 7.53 mmol, 2.4 eq) were heated in Et₂O (30 mL) for 20 h. After purification (silica gel, EtOAc/CyHex=1:20), 525 mg (1.72 mmol, 57%) of inventive complex rac-85 were isolated as a yellow oil. The yellow oil solidified when cooled in a refrigerator after several days.

TLC: $R_f$(CyHex/EtOAc=5:1)=0.65.

¹H NMR (600 MHz, CDCl₃): δ=5.62 (d, J=6.0 Hz, 1H, H6), 3.07 (Ψd, J=2.0 Hz, 1H, H2), 2.75-2.72 (m, 1H, H5), 2.17 (s, 3H, H8), 1.56-1.41 (m, 2H, H4), 1.08 (s, 3H, H9/H10), 1.03 (s, 3H, H9/H10).

¹³C NMR (150 MHz, CDCl₃): δ=211.0 (Fe(CO)₃), 169.7 (C7), 126.6 (C1), 81.1 (C6), 71.1 (C2), 51.4 (C5), 42.1 (C4), 36.14 (C3), 34.6 (C9/C10), 30.8 (C9/C10), 21.2 (C8).

FT-IR (ATR): $\tilde{\nu}$ [cm$^{-1}$]=2953 (m, $\nu$(C$_{sp3}$—H)), 2866 (w, $\nu$(C$_{sp3}$—H)), 2043 (s, $\nu$(Fe(CO)$_3$)), 1961 (bs, $\nu$(Fe(CO)$_3$)), 1767 (s, $\nu$(C=O)), 1446 (m), 1367 (m), 1192 (s), 1146 (s), 1120 (m), 1020 (m), 893 (m).

EA: Calculated for C$_{13}$H$_{14}$FeO$_5$: C, 51.01; H, 4.61. Found: C, 51.00; H, 4.65.

Example 20

Preparation of (RS)-[$\eta^4$-5,5-dimethylcyclohexa-1,3-dien-1-yl-tricarbonyliron(0)]acetate (rac-84)

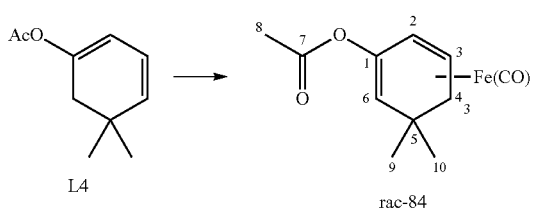

Pursuant to the General Complexation Protocol, diene L4 (500 mg, 3.01 mmol, 1.0 eq) and Fe$_2$(CO)$_9$ (2.75 g, 7.53 mmol, 2.4 eq) were heated in Et$_2$O (30 mL) for 20 h. After purification (silica gel, EtOAc/CyHex=1:20), 525 mg (1.72 mmol, 57%) of inventive complex rac-84 were isolated as a yellow oil.

TLC:R$_f$(CyHex/EtOAc=5:1)=0.65.

$^1$H NMR (500 MHz, CDCl$_3$): δ=5.40-5.35 (m, 1H, H2), 5.07 (dd, J=4.5, 6.5 Hz, 1H, H3), 2.76 (Ψdd, J=1.0, 6.5 Hz, 1H, H4), 2.20-2.10 (m, 1H, H6), 2.02 (s, 3H, H8), 1.76-1.70 (m, 1H, H6), 1.09 (s, 3H, H9/H10), 0.96 (s, 3H, H9/H10).

$^{13}$C NMR (125 MHz, CDCl$_3$): δ=169.7 (C7), 101.9 (C1), 81.3 (C2), 77.4 (C3), 72.6 (C4), 44.9 (C6), 34.9 (C9/C10), 30.9 (C9/C10), 20.9 (C8).

FT-IR (ATR): $\tilde{\nu}$ [cm$^{-1}$]=2957 (m, $\nu$(C$_{sp3}$—H)), 2860 (w, $\nu$(C$_{sp3}$—H)), 2044 (s, $\nu$(Fe(CO)$_3$)), 1962 (bs, $\nu$(Fe(CO)$_3$)), 1752 (s, $\nu$(C=O)), 1470 (w), 1440 (m), 1366 (s), 1212 (s), 1184 (s), 1095 (s), 1052 (m), 1013 (w), 908 (m).

Example 21

Preparation of (RS)-[$\eta^4$-6-methyl-2-oxo-2H-pyran-4-yl-tricarbonyliron(0)]acetate (rac-88)

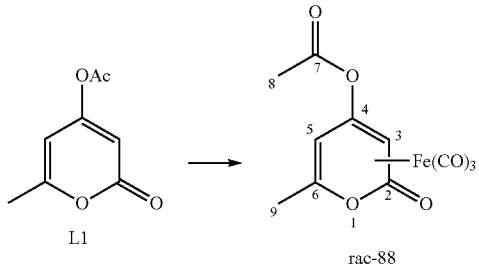

Pursuant to the General Complexation Protocol, diene L1 (500 mg, 2.97 mmol, 1.0 eq) and Fe$_2$(CO)$_9$ (2.18 g, 6.0 mmol, 2.0 eq) were heated in Et$_2$O (30 mL) for 30 h. After purification (silica gel, EtOAc/CyHex=1:3), 118 mg (0.38 mmol, 13%) of inventive complex rac-88 were isolated as a yellow oil.

TLC: R$_f$(CyHex/EtOAc=1:1)=0.70.

$^1$H NMR (300 MHz, CDCl$_3$): δ=5.96 (s, 1H, H5), 3.20 (s, 1H, H3), 2.28 (s, 3H, H8), 1.87 (s, 3H, H9).

$^{13}$C NMR (75 MHz, CDCl$_3$): δ=170.0 (C2), 168.0 (C7), 128.1 (C4), 94.8 (C6), 70.6 (C5), 46.2 (C3), 22.5 (C9), 21.2 (C8).

FT-IR (ATR): $\tilde{\nu}$ [cm$^{-1}$]=2067 (s, $\nu$(Fe(CO)$_3$)), 1991 (bs, $\nu$(Fe(CO)$_3$)), 1781 (s, $\nu$(C=O)), 1748 (s, $\nu$(C=O)), 1480 (m), 1403 (w), 1369 (m), 1251 (w), 1179 (s), 1113 (m), 1044 (w), 1013 (m), 923 (m), 881 (m).

Example 22

Preparation of (RS)-[$\eta^4$-6-((trimethylsilyl)ethynyl)cyclohexa-1,5-dien-1-yl-tricarbonyliron(0)]acetate (rac-95)

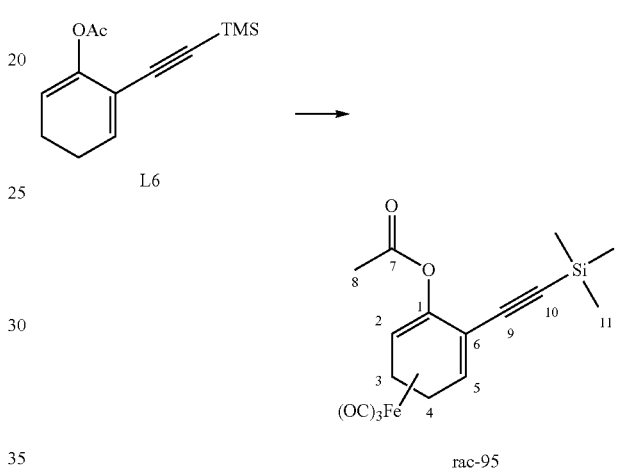

Pursuant to the General Complexation Protocol, diene L6 (630 mg, 2.69 mmol, 1.0 eq) and Fe$_2$(CO)$_9$ (1.96 g, 5.4 mmol, 2.0 eq) were heated in toluene (30 mL) for 30 h. After purification, 250 mg (0.67 mmol, 25%) of inventive complex rac-95 were isolated as a yellow oil.

$^1$H NMR (600 MHz, CDCl$_3$): δ=3.31-3.26 (m, 1H, H5), 3.02-2.99 (m, 1H, H2), 2.22 (s, 3H, H8), 1.82-1.64 (m, 2H, H4), 1.62-1.55 (m, 2H, H3), 0.18 (s, 9H, H11).

$^{13}$C NMR (150 MHz, CDCl$_3$): δ=169.7 (C7), 129.4 (C1), 99.2 (C10), 96.3 (C6), 79.7 (C9), 58.0 (C5), 55.7 (C2), 24.6 (C3), 23.9 (C4), 20.7 (C8), −0.24 (C11).

FT-IR (ATR): $\tilde{\nu}$ [cm$^{-1}$]=2957 (m, $\nu$(C$_{sp3}$—H)), 2852 (w, $\nu$(C$_{sp3}$—H)), 2050 (s, $\nu$(Fe(CO)$_3$)), 1972 (bs, $\nu$(Fe(CO)$_3$)), 1768 (s, $\nu$(C=O)), 1455 (w), 1419 (m), 1367 (m), 1249 (m), 1194 (s), 1134 (s), 1082 (w), 1012 (w), 892 (m), 844 (s), 760 (m).

Example 23

Preparation of (RS)-[$\eta^4$-(E)-Nona-1,3-dien-2-yl-tricarbonyliron(0)]acetate (rac-93)

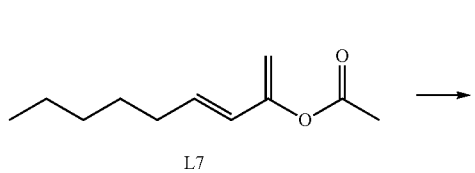

-continued

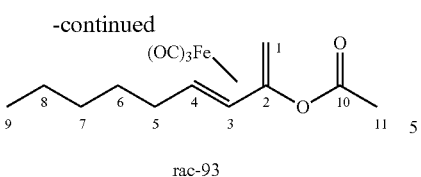

rac-93

Pursuant to the General Complexation Protocol, diene L7 (500 mg, 2.7 mmol, 1.0 eq) and $Fe_2(CO)_9$ (2.0 g, 5.5 mmol, 2.0 eq) were heated in $Et_2O$ (20 mL) for 40 h. After purification, 250 mg (0.78 mmol, 29%) of inventive complex rac-93 were isolated as a yellow oil.

TLC: $R_f$(CyHex/EtOAc=10:1)=0.53.

$^1$H NMR (600 MHz, $CDCl_3$): δ=5.44 (d, J=8.2 Hz, 1H, H3), 2.18 (s, 3H, H11), 1.97 (Ψdd, J=1.7, 4.6 Hz, 1H, H1$_{exo}$), 1.72-1.66 (m, 1H, H5), 1.57-1.50 (m, 1H, H5), 1.43-1.35 (m, 2H, H6), 1.31-1.22 (m, 4H, H7, H8), 0.86 (t, J=7.0 Hz, 3H, H9), 0.53 (d, J=4.3 Hz, 1H, H1$_{endo}$), 0.50 (Ψg, J=7.3 Hz, 1H, H4).

$^{13}$C NMR (150 MHz, $CDCl_3$): δ=170.2 (C10), 126.2 (C2), 83.0 (C3), 56.2 (C4), 36.8 (C1), 34.1 (C5), 31.8 (C6), 31.4 (C7), 22.4 (C8), 21.0 (C11), 13.9 (C9).

FT-IR (ATR): $\tilde{v}$ [cm$^{-1}$]=2930 (s, $v(C_{sp3}$—H)), 2859 (m, $v(C_{sp3}$—H)), 2048 (s, $v(Fe(CO)_3)$), 1965 (bs, $v(Fe(CO)_3)$), 1766 (s, $v(C=O)$), 1490 (w), 1461 (w), 1368 (m), 1195 (bs), 1109 (w), 1012 (w), 924 (m).

LR-MS (DIP-MS, 70 eV): m/z (%)=294 (5, [M-CO]$^+$), 266 (23, [M-2CO]$^+$], 238 (56, [M-3CO]$^+$), 209 (14), 195 (24), 182 (32, [M-Fe(CO)$_3$]$^+$), 178 (62), 140 (10, [M-Fe(CO)$_3$—$CH_2CO$)]$^+$), 139 (42, [M-Fe(CO)$_3$—$CH_3CO$)]$^+$), 134 (53), 124 (33), 122 (50), 121 (63), 115 (75), 97 (31), 84 (35), 71 (50), 57 (39. [$C_4H_9$]$^+$), 56 (100, [Fe]$^+$).

HR-MS (DIP-MS, 70 eV): m/z 294.055±0.0012 (calculated ([M-CO]$^+$): m/z 294.0555).

Example 24

Preparation of (RS)-[η$^4$-(E)-4-phenylbuta-1,3-dien-2-yl-tricarbonyliron(0)]acetate (rac-97)

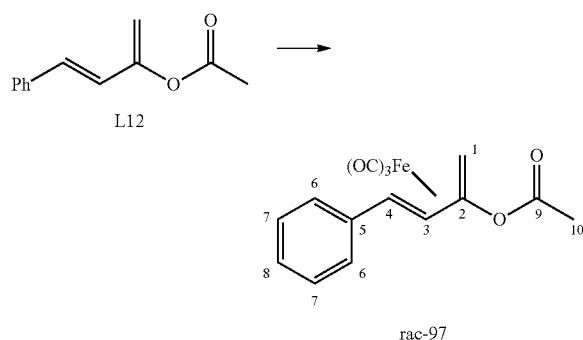

rac-97

Pursuant to the General Complexation Protocol, diene L12 (300 mg, 1.9 mmol, 1.0 eq) and $Fe_2(CO)_9$ (1.8 g, 4.8 mmol, 2.5 eq) were heated in $Et_2O$ (30 mL) for 40 h. After purification, 70 mg (0.21 mmol, 11%) of inventive complex rac-97 was isolated as a yellow solid.

TLC: $R_f$(CyHex/EtOAc=10:1)=0.43.

$^1$H NMR (500 MHz, $CDCl_3$): δ=7.24 (Ψt, J=7.4 Hz, 2H, H7), 7.19 (d, J=7.3 Hz, 2H, H6), 7.15 (t, J=7.0 Hz, 1H, H8), 6.10 (d, J=8.6 Hz, 1H, H3), 2.24 (s, 3H, H10), 2.17 (d, J=3.5 Hz, 1H, H1$_{exo}$), 1.54 (d, J=8.7 Hz, 1H, H4), 0.89 (d, J=4.5 Hz, 1H, H1$_{endo}$).

$^{13}$C NMR (125 MHz, $CDCl_3$): δ=170.2 (C9), 139.5 (C5), 128.5 ($CH_{ar}$), 126.6 ($CH_{ar}$), 126.3 ($CH_{ar}$), 126.3 (C2), 78.4 (C3), 53.2 (C4), 36.9 (C1), 21.1 (C10).

FT-IR (ATR): $\tilde{v}$ [cm$^{-1}$]=3070 (w, $v(C_{sp2}$—H)), 2960 (w, $v(C_{sp3}$—H)), 2045 (s, $v(Fe(CO)_3)$), 1980 (s, $v(Fe(CO)_3)$), 1963 (s, $v(Fe(CO)_3)$), 1757 (s, $v(C=O)$), 1486 (w), 1367 (w), 1323 (w), 1212 (m), 1185 (m), 1011 (m), 926 (w), 848 (w), 759 (m), 694 (m).

LR-MS (DIP-MS, 70 eV): m/z (%)=300 (3, [M-CO]$^+$), 272 (16, [M-2CO]$^+$), 244 (17, [M-3CO]$^+$), 201 (9, [M-3CO—$COCH_3$]$^+$), 185 (12, [M-3CO—$OCOCH_3$]$^+$), 184 (100), 159 (7), 133 (17), 128 (39), 91 (5, [$C_7H_7$]$^+$), 84 (5), 77 (6), 71 (5), 57 (7), 56 (45, [Fe]$^+$).

$T_m$(DCM)=97.7° C.

Example 25

Preparation of [η$^4$-((S)-3-isopropyl-6-methylcyclohexa-1,5-dien-1-yl-tricarbonyliron(0)]acetate (81)

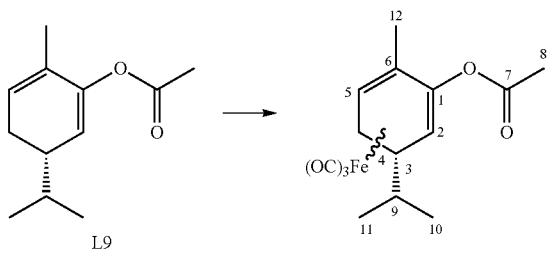

Pursuant to the General Complexation Protocol, diene L9 (250 mg, 1.29 mmol, 1.0 eq) and $Fe_2(CO)_9$ (940 mg, 2.57 mmol, 2.0 eq) were heated in $Et_2O$ (40 mL) for 48 h. After purification, 85 mg (0.25 mmol, 19%) of inventive complex 81 was isolated as a yellow oil as a single diastereomer whose relative configuration could not be more exactly determined.

TLC: $R_f$(CyHex/EtOAc=10:1)=0.8.

$^1$H NMR (500 MHz, $CDCl_3$): δ=3.24 (d, J=2.5 Hz, 1H, H5), 2.71 (Ψd, J=1.5 Hz, 1H, H2), 2.20 (s, 3H, H12), 2.06 (s, 3H, H8), 1.78-1.72 (m, 1H, H4), 1.66-1.61 (m, 1H, H3), 1.34-1.23 (m, 2H, H4, H9), 0.85 (d, J=6.6 Hz, 3H, H10/H11), 0.76 (d, J=6.6 Hz, 3H, H10/H11).

$^{13}$C NMR (125 MHz, $CDCl_3$): δ=210.8 (Fe(CO)$_3$), 169.5 (C7), 126.4 (C1), 96.7 (C6), 58.9 (C2), 54.4 (C5), 48.2 (C3), 36.0 (C9), 29.7 (C4), 22.2 (C10/C11), 21.0 (C10/C11/C12), 20.8 (C10/C11/C12), 17.2 (C8).

FT-IR (ATR): $\tilde{v}$ [cm$^{-1}$]=2959 (m, $v(C_{sp3}$—H)), 2866 (w, $v(C_{sp3}$—H)), 2042 (s, $v(Fe(CO)_3)$), 1960 (bs, $v(Fe(CO)_3)$), 1764 (s, $v(C=O)$), 1490 (w), 1440 (m), 1416 (m), 1367 (m), 1203 (s), 1135 (s), 1010 (m), 899 (m).

LR-MS (DIP-MS, 70 eV): m/z (%)=306 (7, [M-CO]$^+$), 278 (18, [M-2CO]$^+$), 248 (100, [M-3CO]$^+$), 233 (24), 207 (12), 191 (4), 163 (16), 149 (15), 57 (62, [Fe]$^+$).

Example 26

Preparation of [η⁴-((R)-3-isopropyl-6-methylcyclo-hexa-1,5-dien-1-yl-tricarbonyliron(0)]acetate (83)

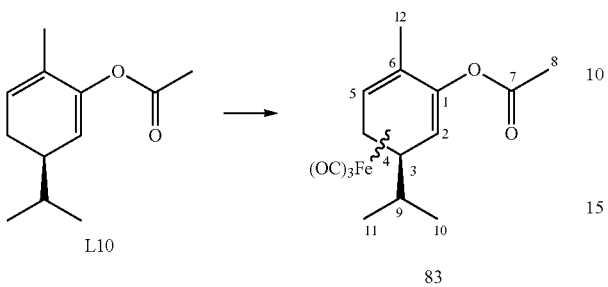

Pursuant to the General Complexation Protocol, diene L10 (700 mg, 3.6 mmol, 1.0 eq) and $Fe_2(CO)_9$ (3.3 g, 9.0 mmol, 2.5 eq) were heated in $Et_2O$ (50 mL) for 40 h. After purification, 364 mg (1.09 mmol, 31%) of inventive complex 83 were isolated as a yellow oil as a single diastereomer whose relative configuration could not be more exactly determined.

TLC: $R_f$(CyHex/EtOAc=10:1)=0.8.

$^1$H NMR (400 MHz, $CDCl_3$): δ=3.36-3.26 (m, 1H, H5), 2.18-2.71 (m, 1H, H2), 2.20 (s, 3H, H12), 2.07 (s, 3H, H8), 181-1.61 (m, 2H, H4, H3), 1.36-1.25 (m, 2H, H4, H9), 0.85 (d, J=8.4 Hz, 3H, H10/H11), 0.76 (d, J=8.4 Hz, 3H, H10/H11).

$^{13}$C NMR (100 MHz, $CDCl_3$): δ=210.9 ($Fe(CO)_3$), 169.4 (C7), 126.8 (C1), 96.7 (C6), 58.9 (C2), 54.4 (C5), 48.3 (C3), 36.0 (C9), 29.7 (C4), 22.2 (C10/C11), 21.0 (C10/C11/C12), 20.8 (C10/C11/C12), 17.2 (C8).

FT-IR (ATR): ṽ [cm$^{-1}$]=2955 (m, ν($C_{sp3}$—H)), 2863 (w, ν($C_{sp3}$—H)), 2043 (s, ν($Fe(CO)_3$)), 1966 (bs, ν($Fe(CO)_3$)), 1762 (s, ν(C=O)), 1488 (w), 1446 (m), 1367 (m), 1204 (s), 1135 (s), 1010 (m), 900 (m).

Example 27

Preparation of (RS)-[η⁴-Cyclohexa-1,3-dien-1-yl-tricarbonyliron(0)] pivalate (rac-80)

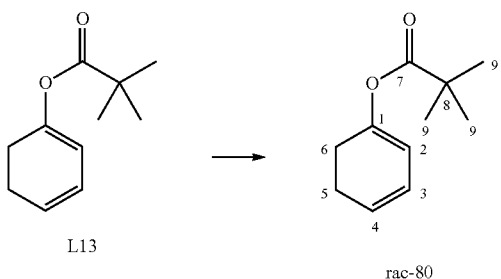

Pursuant to the General Complexation Protocol, diene L13 (700 mg, 3.88 mmol, 1.0 eq) and $Fe_2(CO)_9$ (3.5 g, 9.6 mmol, 2.4 eq) were heated in $Et_2O$ (30 mL) for 16 h. After purification, 895 mg (2.79 mmol, 72%) of inventive complex rac-80 were isolated as a yellow crystalline solid.

TLC: $R_f$(CyHex/EtOAc=10:1)=0.80.

$^1$H NMR (500 MHz, $CDCl_3$): δ=5.39 (d, J=4.0 Hz, 1H, H2), 5.13 (Ψt, J=5.5 Hz, 1H, H3), 3.13-3.08 (m, 1H, H4), 2.18-2.09 (m, 1H, H5/H6), 1.92-1.85 (m, 1H, H5/H6), 1.81-1.74 (m, 1H, H5/H6), 1.74-1.64 (m, 1H, H5/H6), 1.22 (s, 9H, H9).

$^{13}$C NMR (125 MHz, $CDCl_3$): δ=211.4 ($Fe(CO)_3$), 176.7 (C7), 103.4 (C1), 80.4 (C2/C3), 80.3 (C2/C3), 60.2 (C4), 38.9 (C8), 27.0 (C9), 26.5 (C5/C6), 24.0 (C5/C6).

FT-IR (ATR): ṽ [cm$^{-1}$]=2931 (s, ν($C_{sp3}$—H)), 2859 (m, ν($C_{sp3}$—H)), 2047 (s, ν($Fe(CO)_3$)), 1970 (bs, ν($Fe(CO)_3$)), 1739 (s, ν(C=O)), 1455 (w), 1380 (w), 1327 (w), 1277 (m), 1181 (m), 1129 (s), 1004 (w), 904 (m).

EA: Calculated for $C_{14}H_{16}FeO_5$: C, 52.53; H, 5.04. Found: C, 52.36; H, 5.05.

Example 28

Preparation of [η⁴-cholesta-2,4-dien-3-yl tricarbonyliron(0)]acetate (98)

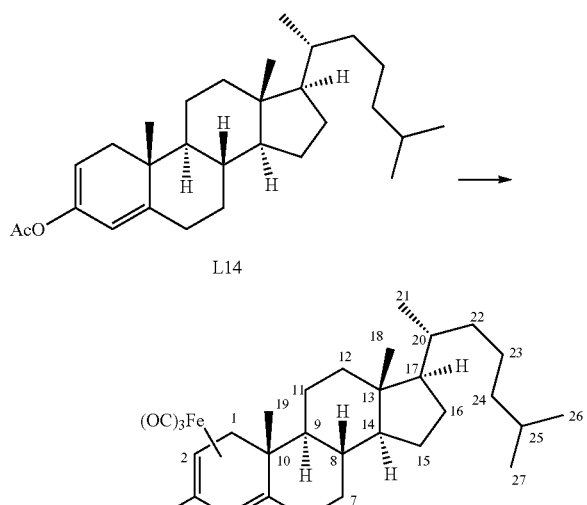

Pursuant to the General Complexation Protocol, diene L14 (400 mg, 0.93 mmol, 1.0 eq) and $Fe_2(CO)_9$ (900 mg, 2.48 mmol, 2.7 eq) were heated in $Et_2O$ (30 mL) for 48 h. After purification (silica gel, CyHex/DCM/Toluol=20:1:5), 324 mg (0.57 mmol, 61%) of inventive complex 98 were isolated as two separated diastereomers having a diastereomeric ratio of 6:1 (278 mg (0.49 mmol, 53%) of the major diastereomer and 46 mg (0.08 mmol, 8%) of the minor diastereomer). Analytic data provided is for the major diastereomer.

TLC: $R_f$(CyHex/EtOAc=10:1)=0.8 for the major diastereomer.

$R_f$(CyHex/EtOAc=10:1)=0.9 for the minor diastereomer.

$^1$H NMR (500 MHz, $CDCl_3$): δ=5.36 (Ψd, J=1.6 Hz, 1H, CH), 3.10 (Pd, J=2.2 Hz, 1H, CH), 2.20-2.14 (m, 1H), 2.17 (s, 3H, $COOCH_3$) 1.94-1.92 (m, 1H), 1.85-1.77 (m, 2H), 1.73-1.69 (m, 1H), 1.65-1.62 (m, 1H), 1.60-1.47 (m, 3H), 1.36-1.29 (m, 3H), 1.23-1.04 (m, 11H), 1.00 (s, 3H, H19), 0.98-0.92 (m, 3H), 0.87 (d, J=6.5 Hz, 3H, H21/26/27), 0.85 (d, J=3.0 Hz, 3H, H21/26/27), 0.83 (d, J=2.5 Hz, 3H, H21/26/27), 0.62 (s, 3H, H18).

$^{13}$C NMR (125 MHz, $CDCl_3$): δ=170.4 ($COOCH_3$), 126.8 (C3), 82.1 (C5), 80.6 (C4), 56.4 (C2), 56.1 (CH), 52.9 (CH), 44.9 ($CH_2$), 42.8 ($C_q$), 40.1, 39.5, 36.4 (CH), 36.1, 35.8 (CH), 32.8, 31.7, 28.2, 28.0 (CH), 25.3 (C19), 24.0, 23.7, 22.8 (C21 (C26/C27), 22.5 (C21/C26/C27), 22.0, 20.9 (COOCH$_3$), 18.67 (C18).

FT-IR (ATR): $\tilde{\nu}$ [cm$^{-1}$]=2931 (m, $\nu$(C$_{sp3}$—H)), 2840 (w, $\nu$(C$_{sp3}$—H)), 2038 (s, $\nu$(Fe(CO)$_3$)), 1961 (bs, $\nu$(Fe(CO)$_3$)), 1761 (m, $\nu$(C=O)), 1461 (w), 1369 (m), 1194 (s), 1039 (w), 1043 (w), 926 (w), 896 (w).

LR-MS (DIP-MS, 70 eV): m/z (%)=510 (7, [M-2CO]$^+$), 482 (47, [M-3CO]$^+$]), 422 (17), 384 (18), 220 (19), 162 (25), 122 (68), 91 (50), 57 (100, [Fe]$^+$).

Example 29

Preparation of (RS)-[$\eta^4$-Cyclohexa-1,3-dien-1,3-diyl-tricarbonyliron(0)] bis(2,2-dimethylpropanoate) (rac-89)

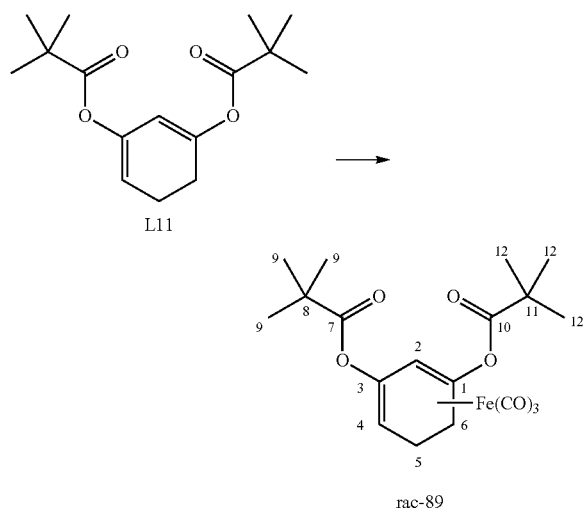

Pursuant to the General Complexation Protocol, a mixture containing diene L11 (prepared pursuant to Example 12) (400 mg, 1.42 mmol, 1.0 eq) and Fe$_2$(CO)$_9$ (1.5 g, 4.12 mmol, 2.9 eq) were heated in Et$_2$O (30 mL) for 16 h. After purification, 251 mg (0.60 mmol, 42%) of inventive complex rac-89 were isolated as a yellow oil.

TLC: R$_f$(CyHex/EtOAc=10:1)=0.52.

$^1$H NMR (600 MHz, CDCl$_3$): δ=5.72-5.55 (m, 1H, H2), 3.26-3.25 (m, 1H, H4), 2.12-1.93 (m, 1H, H6), 1.84-1.81 (m, 2H, H5), 1.69-1.62 (m, 1H, H6), 1.23 (s, 9H, H9/H12), 1.17 (s, 9H, H9/H12).

$^{13}$C NMR (150 MHz, CDCl$_3$): δ=177.7 (C7/C10), 176.7 (C7/C10), 124.1 (C3), 94.9 (C1), 74.9 (C2), 57.1 (C4), 39.1 (C8/C11), 39.0 (C8/C11), 27.0 (C9/C12), 26.9 (C9/C12), 26.2 (C6), 23.6 (C5).

FT-IR (ATR): $\tilde{\nu}$ [cm$^{-1}$]=2974 (m, $\nu$(C$_{sp3}$—H)), 2926 (m, $\nu$(C$_{sp3}$—H)), 2900 (w, $\nu$(C$_{sp3}$—H)), 2052 (s, $\nu$(Fe(CO)$_3$)), 1979 (bs, $\nu$(Fe(CO)$_3$)), 1753 (s, $\nu$(C=O)), 1740 (s, $\nu$(C=O)), 1480 (m), 1460 (m), 1396 (w), 1365 (w), 1276 (m), 1175 (m), 1104 (s), 1045 (w), 1028 (m), 886 (m), 671 (m).

EA: Calculated for C$_{19}$H$_{24}$FeO$_7$: C, 54.30; H, 5.76. Found: C, 54.46; H, 5.78.

Example 30

Preparation of (RS)-[$\eta^4$-(1-(6-hydroxyhexyl)-1H-1,2,3-triazol-4-yl)cyclohexa-1,5-dien-1-yl-tricarbonyliron(0)]acetate (rac-94)

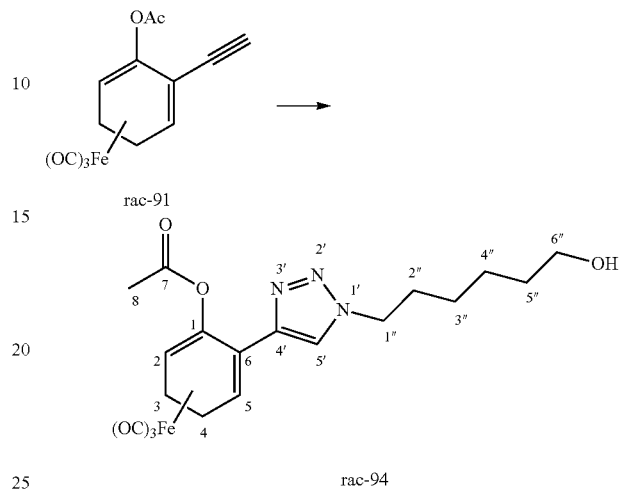

To a solution of inventive complex rac-91 (150 mg, 0.50 mmol, 1.0 eq), 6-azido-hexan-1-ol (216 mg, 1.25 mmol, 2.5 eq) and CuI (19 mg, 9.5 μmol 0.15 eq) in degassed THF (20 mL) was added diisopropylethylamine (1.1 mL, 0.85 g, 6.6 mmol, 13.2 eq); the mixture being stirred for 24 h at 25° C. The solvent was evaporated and the raw product purified by column chromatography (silica gel, CyHex/EtOAc=2:1) to yield 143 mg (0.32 mmol, 64%) of inventive complex rac-94 as a yellow foam.

$^1$H NMR (300 MHz, CDCl$_3$): δ=7.65 (s, 1H, H5'), 4.37 (Ψt, J=4.0 Hz, 2H, H1"), 3.62 (s, 1H, H5), 3.59 (Ψbs, 2H, H6"), 3.35 (s, 1H, H2), 2.26 (s, 3H, H8), 1.90-1.86 (m, 3H, H3, H2"), 1.78-1.69 (m, 3H, H4, H3), 1.51 (Ψbs, 2H, H5"), 1.38 (Ψbs, 2H, H4"), 1.32-1.26 (m, 2H, H3").

$^{13}$C NMR (75 MHz, CDCl$_3$): δ=210.0 (Fe(CO)$_3$), 169.8 (C7), 143.4 (C1), 124.9 (C4'), 121.9 (C5'), 87.4 (C6), 62.4 (C6"), 57.5 (C2), 51.7 (C5), 50.3 (C1"), 32.2 (C5"), 30.1 (C2"), 26.0 (C3"/C4"), 25.0 (C3"/C4"), 24.9 (C3), 24.0 (C4), 21.1 (C8).

FT-IR (ATR): $\tilde{\nu}$ [cm$^{-1}$]=3388 (bm, $\nu$(O—H)), 2938 (s, $\nu$(C$_{sp3}$—H)), 2854 (m, $\nu$(C$_{sp3}$—H)), 2044 (s, $\nu$(Fe(CO)$_3$)), 1972 (bs, $\nu$(Fe(CO)$_3$)), 1765 (s, $\nu$(C=O)), 1456 (m), 1416 (m), 1368 (m), 1199 (s), 1184 (s), 1145 (m), 1088 (m), 1046 (m), 1013 (m), 906 (m), 879 (m).

Example 31

Preparation of (RS)-[$\eta^4$-6-(1-benzyl-1H-1,2,3-triazol-4-yl)cyclohexa-1,5-dien-1-yl-tricarbonyliron(0)] acetate (rac-92)

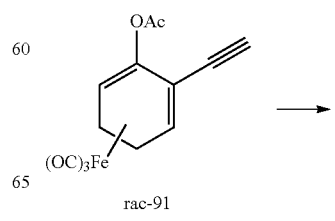

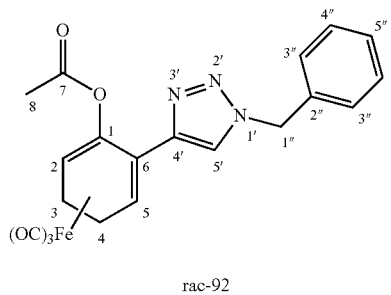

rac-92

To a solution of inventive complex rac-91 (150 mg, 0.50 mmol, 1.0 eq), benzyl azide (216 mg, 1.62 mmol, 3.24 eq) and CuI (19 mg, 9.5 mmol, 0.15 eq) in degassed THF (20 mL) was added diisopropylethylamine (1.1 mL, 0.85 g, 6.6 mmol, 13.2 eq); the mixture being stirred for 24 h at 25° C. The solvent was evaporated and the raw product purified by column chromatography (silica gel, CyHex/EtOAc=2:1) to yield 195 mg (0.45 mmol, 90%) of inventive complex rac-92 as a yellow foam.

$^1$H NMR (600 MHz, CDCl$_3$): δ=7.55 (s, 1H, H5'), 7.36-7.35 (m, 3H, H4", H5"), 7.22-7.21 (m, 2H, H3"), 5.58 (d, J=14.9 Hz, 1H, H1"), 5.50 (d, J=14.9 Hz, 1H, H1"), 3.62 (s, 1H, H5), 3.33 (s, 1H, H2), 2.10 (s, 3H, H8), 1.88-1.85 (m, 1H, H3), 1.76-1.66 (m, 3H, H4, H3).

$^{13}$C NMR (150 MHz, CDCl$_3$): δ=209.9 (Fe(CO)$_3$), 169.1 (C7), 143.9 (C1), 134.5 (C2"), 129.2 (C4"), 128.9 (C5"), 128.1 (C3"), 125.0 (C4'), 122.0 (C5'), 87.4 (C6), 57.6 (C2), 54.3 (C1"), 51.7 (C5), 25.0 (C3), 24.1 (C4), 21.0 (C8).

FT-IR (ATR): ν [cm$^{-1}$]=3143 (w), 2938 (w, ν(C$_{sp3}$—H)), 2850 (w, ν(C$_{sp3}$—H)), 2044 (s, ν(Fe(CO)$_3$)), 1956 (bs, ν(Fe(CO)$_3$)), 1765 (s, ν(C=O)), 1496 (m), 1455 (m), 1413 (m), 1367 (m), 1198 (s), 1183 (s), 1131 (m), 1087 (m), 1044 (m), 1011 (m), 975 (w), 906 (m), 879 (m), 809 (w).

Example 32

Preparation of (RS)-[η$^4$-6-ethynylcyclohexa-1,5-dien-1-yl-tricarbonyliron(0)]acetate (rac-91)

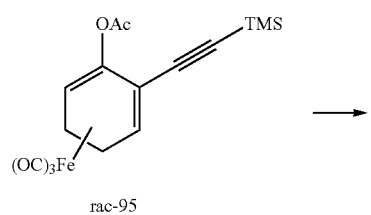

rac-95

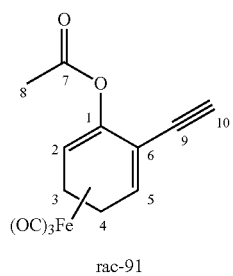

rac-91

To a solution of inventive complex rac-95 (200 mg, 0.53 mmol, 1.0 eq) in THF (20 mL) at −78° C. was added Ac$_2$O (0.15 mL, 1.53 mmol, 2.9 eq) and tetra-n-butylammonium fluoride (1.53 mL, 1.53 mmol, 2.9 eq, 1 M in THF). After stirring at −78° C. (for approximately 3 h), the reaction was quenched by adding saturated aqueous NH$_4$Cl (40 mL). The mixture was extracted with Et$_2$O (100 mL) and the organic phase was washed with water and brine. The combined organic phases were dried over MgSO$_4$. The solvent was evaporated and the raw product was purified by column chromatography (silica gel, CyHex/EtOAc=20:1) to yield 145 mg (0.48 mmol, 90%) of inventive complex rac-91 as a yellow crystalline solid.

$^1$H NMR (300 MHz, CDCl$_3$): δ=3.32-3.30 (m, 1H, H5), 3.02-3.00 (m, 1H, H2), 2.93 (s, 1H, H10), 2.24 (s, 3H, H8), 1.84-1.56 (m, 4H, H3, H4).

FT-IR (ATR): ν [cm$^{-1}$]=2957 (m, ν(C$_{sp3}$—H)), 2898 (w, ν(C$_{sp3}$—H)), 2850 (w, ν(C$_{sp3}$—H)), 2051 (s, ν(Fe(CO)$_3$)), 1979 (bs, ν(Fe(CO)$_3$)), 1768 (s, ν(C=O)), 1457 (w), 1419 (m), 1367 (m), 1249 (m), 1193 (s), 1134 (s), 1082 (w), 1012 (w), 892 (2), 844 (s), 760 (m).

FIG. 1 shows the molecular structure for (RS)-[η$^4$-6-ethynylcyclohexa-1,5-dien-1-yl-tricarbonyliron(0)]acetate (rac-91) obtained by X-ray crystallography.

The X-ray crystal structure analysis of rac-91 provides the following information:

| | | |
|---|---|---|
| Wavelength | 0.71073 Å | |
| Crystal system, space group | Triclinic, P-1 | |
| Unit cell dimensions | a = 7.0707(5) Å | alpha = 90.728(4) deg. |
| | b = 7.4930(5) Å | beta = 100.295(3) deg. |
| | c = 12.7867(8) Å | gamma = 97.072(4) deg. |
| Volume | 661.05(8) Å$^3$ | |
| Z, Calculated density | 2, 1.518 Mg/m$^3$ | |
| Absorption coefficient | 1.152 mm$^{-1}$ | |
| F(000) | 308 | |
| Crystal size | .2 × .07 × .05 mm | |
| Theta range for data collection | 1.62 to 27.00 deg. | |
| Limiting indices | −8 <= h <= 9, −9 <= k <= 9, −16 <= l <= 13 | |
| Reflections collected/unique | 4115/2838 [R(int) = 0.0226] | |
| Reflection observed [I > 2sigma(I)] | 2200 | |
| Completeness to theta = 27.00 | 98.7% | |
| Absorption correction | None | |
| Refinement method | Full-matrix least-squares on F$^2$ | |
| Data/restraints/parameters | 2838/0/173 | |
| Goodness-of-fit on F$^2$ | 1.017 | |
| Final R indices [I > 2sigma(I)] | R1 = 0.0374, wR2 = 0.0789 | |
| R indices (all data) | R1 = 0.0579, wR2 = 0.0911 | |
| Largest diff. peak and hole | 0.549 and −0.623 e.Å$^{-3}$ | |

Example 33

Preparation of (RS)-[η$^4$-4-azidocyclohexa-1,5-dien-1-yl-tricarbonyliron(0)]acetate (rac-90)

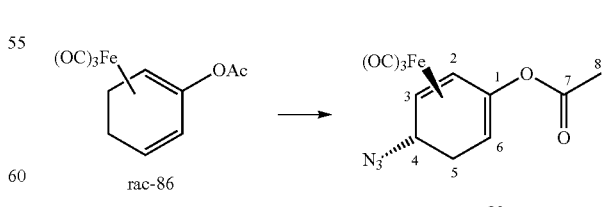

Triphenylmethyl tetrafluoroborate (187 mg, 0.56 mmol, 1.05 eq) was dissolved in DCM (the smallest amount possible) and added dropwise to a solution of inventive complex rac-86 (150 mg, 0.54 mmol, 1 eq) in the same volume of DCM. After 30 min, Et$_2$O (100 mL) was added and a yellow precipitate was filtered off. 240 mg (0.68 mmol, 62%) of the cationic complex, the tetrafluoroborate salt of inventive complex rac-86, were isolated and directly used without further purification.

The isolated tetrafluoroborate salt of inventive complex rac-86 (150 mg, 0.42 mmol) was dissolved in water (5 mL) and added dropwise to a saturated solution of NaN$_3$ in H$_2$O (5 mL). After 30 min at 25° C., the reaction was quenched by addition of Et$_2$O (100 mL). The organic phase was dried over anhydrous MgSO$_4$ and the solvent evaporated. After purification (silica gel, CyHex/EtOAc=20:1), 54 mg (0.17 mmol, 40%) of inventive complex rac-90 were isolated as a yellow oil.

$^1$H NMR (600 MHz, CDCl$_3$): δ=5.56-5.52 (m, 1H, H6), 5.33-5.26 (m, 1H, H5), 4.50-4.44 (m, 1H, H2), 2.89-2.83 (m, 1H, H4), 2.42-2.32 (m, 1H, H3), 2.07 (s, 3H, H8), 1.60-1.53 (m, 1H, H3).

$^{13}$C NMR (150 MHz, CDCl$_3$): δ=169.2 (C7), 101.0 (C1), 82.8 (C5), 78.9 (C6), 59.7 (C2), 54.3 (C4), 31.7 (C3), 21.0 (C8).

FT-IR (ATR): ṽ [cm$^{-1}$]=2150 (s, $v_{as}$(N$_3$)), 2052 (s, v(Fe(CO)$_3$)), 1980 (bs, v(Fe(CO)$_3$)), 1755 (s, v(C=O)), 1430 (w), 1368 (m), 1325 (w), 1211 (s), 1112 (s), 1010 (w), 904 (w).

Example 34

Preparation of (RS)-[η$^4$-(E)-Nona-1,3-dien-2-yl-tricarbonyliron(0)])] pivalate (rac-99)

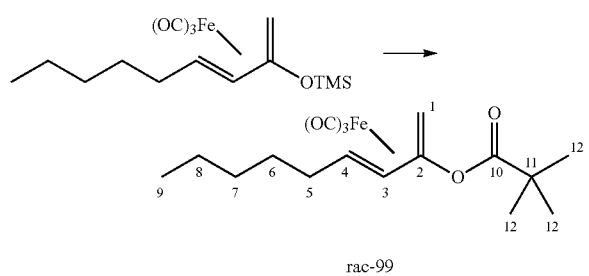

rac-99

(E)-trimethyl(nona-1,3-dien-2-yloxy)silanetricaronyliron (0), prepared by refluxing (E)-trimethyl(nona-1,3-dien-2-yloxy)silane (4.2 g, 25.0 mmol, 1.0 eq) and Fe$_2$(CO)$_9$ (10.5 g, 28.9 mmol, 1.2 eq) in dry n-hexane (30 h), was deprotected by flash chromatography (silica gel, CyHex/EtOAc=20:1) under nitrogen. The solvent was evaporated under argon and the resulting dienolether complex was dissolved in DMF (25 mL) and added dropwise to a suspension of NaH (600 mg, 15.0 mmol, 60% in oil) in DMF (25 mL) at 0° C. The reaction mixture was stirred at 0° C. for 45 min. Pivaloylchloride (1.85 mL, 1.81 g, 15.0 mmol) was then added dropwise at the same temperature. After stirring at 25° C. for 3 h, the reaction mixture was diluted with CyHex/EtOAc=1:1 (30 mL) and washed with H$_2$O and brine. The aqueous phase was extracted with MtBE and the combined organic phases were dried over MgSO$_4$. The solvent was evaporated and the raw product purified by column chromatography (silica gel, CyHex/EtOAc=15:1) to yield 1.06 g (2.91 mmol, 16%) of inventive complex rac-99 as a yellow oil.

TLC: R$_f$(CyHex/EtOAc=10:1)=0.35.

$^1$H NMR (600 MHz, CDCl$_3$): δ=5.43 (d, J=8.1 Hz, 1H, H3), 1.97 (Ψdd, J=1.7, 4.4 Hz, 1H, H1$_{exo}$), 1.72-1.66 (m, 1H, H5), 1.57-1.51 (m, 1H, H5), 1.42-1.35 (m, 2H, H6), 1.31-1.22 (m, 4H, H7, H8), 1.25 (s, 9H, H12), 0.86 (t, J=7.6 Hz, 3H, H9), 0.56 (Ψdd, J=0.6, 4.5 Hz, 1H, H1$_{endo}$), 0.50 (Ψq, J=7.4 Hz, 1H, H4).

$^{13}$C NMR (150 MHz, CDCl$_3$): δ=177.9 (C10), 126.7 (C2), 82.5 (C3), 56.0 (C4), 39.1 (C11), 37.2 (C1), 34.1 (C5), 31.9 (C6), 31.4 (C7), 26.9 (C12), 22.4 (C8), 13.9 (C9).

FT-IR (ATR): ṽ [cm$^{-1}$]=2922 (s, v(C$_{sp3}$—H)), 2848 (s, v(C$_{sp3}$—H)), 2048 (s, v(Fe(CO)$_3$)), 1975 (bs, v(Fe(CO)$_3$)), 1757 (m, v(C=O)), 1449 (m), 1269 (w), 1110 (m), 1028 (w), 899 (w), 854 (w).

LR-MS (DIP-MS, 70 eV): m/z (%)=336 (3, [M-CO]$^+$), 308 (23, [M-2CO]$^+$), 280 (67, [M-3CO]$^+$), 265 (7, [M-3CO—CH$_3$]$^+$), 251 (16), 237 (17), 224 (32, [M-Fe(CO)$_3$]$^+$), 212 (12), 195 (11), 178 (64), 157 (21), 139 (26, [M-Fe(CO)$_3$—OCC(CH$_3$)$_3$]$^+$), 121 (26), 111 (28), 97 (16), 83 (20), 71 (14), 57 (100, [C$_4$H$_9$]$^+$), 56 (30, [Fe]$^+$).

HR-MS (DIP-MS, 70 eV): m/z 308.107±0.0012 (calculated ([M-CO]$^+$): m/z 308.1075).

Example 35

Preparation of (RS)-[η$^4$-cyclohexa-1,5-dien-1-yl-tricarbonyliron(0)] phenylacetate (rac-82)

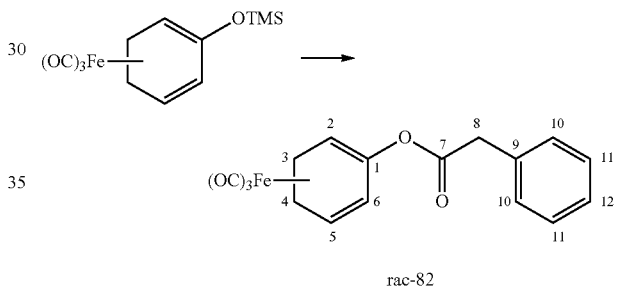

rac-82

(Cyclohexa-1,5-dien-1-yloxy)trimethylsilanetricarbonyliron (0), prepared by refluxing (cyclohexa-1,5-dien-1-yloxy)trimethylsilane (1.13 g, 6.7 mmol, 1.0 eq) and Fe$_2$(CO)$_9$ (3.00 g, 7.95 mmol, 1.2 eq) in Et$_2$O (20 h), was deprotected by flash chromatography (silica gel, CyHex/EtOAc=20:1) under nitrogen. The solvent was evaporated under argon and the resulting dienolether complex was dissolved in DMF (6 mL) and added dropwise to a suspension of NaH (250 mg, 4.18 mmol, 50% in oil) in DMF (6 mL) at 0° C. The reaction mixture was stirred at 0° C. (for approximately 45 min). Phenylacetylchloride (0.6 mL, 1.38 g, 9.0 mmol) was then added dropwise at the same temperature. After stirring at 25° C. (for approximately 3 h), the reaction mixture was diluted with CyHex/EtOAc=1:1 (30 mL) and washed with H$_2$O and brine. The aqueous phase was extracted with MtBE and the combined organic phases were dried over anhydrous MgSO$_4$. The solvent was evaporated and the raw product purified by column chromatography (silica gel, CyHex/EtOAc=20:1) to yield 206 mg (0.58 mmol, 9%) of inventive complex rac-82 as a red oil.

TLC: R$_f$(CyHex/EtOAc=10:1)=0.49.

$^1$H NMR (500 MHz, CDCl$_3$): δ=7.35-7.26 (m, 5H, CH$_{ar}$), 5.49 (Ψdd, J=1.50, 6.62 Hz, 1H, H6), 3.72 (s, 2H, H8), 3.29 (Ψtd, J=2.25, 4.2 Hz, 1H, H2), 2.83-2.81 (m, 1H, H5), 1.81-1.75 (m, 1H, H3), 1.74-1.67 (m, 1H, H3), 1.57-1.48 (m, 2H, H4).

$^{13}$C NMR (125 MHz, CDCl$_3$): δ=171.0 (C7), 132.8 (C1), 129.3 (CH$_{ar}$), 129.3 (C$_{q,ar}$), 128.7 (CH$_{ar}$), 127.5 (CH$_{ar}$), 79.7 (C6), 59.0 (C2), 52.0 (C5), 41.1 (C8), 24.5 (C3), 23.4 (C4).

FT-IR (ATR): ṽ [cm$^{-1}$]=3020 (w, ν(C$_{sp2}$—H)), 2929 (w, ν(C$_{sp3}$—H)), 2860 (w, ν(C$_{sp3}$—H)), 2044 (s, ν(Fe(CO)$_3$)), 1966 (bs, ν(Fe(CO)$_3$)), 1761 (s, ν(C=O)), 1595 (w), 1495 (w), 1454 (m), 1434 (w), 1320 (w), 1229 (m), 1168 (s), 1117 (s), 1072 (w), 1024 (w), 994 (w), 922 (w), 899 (m), 748 (m), 720 (m), 695 (m).

LR-MS (DIP-MS, 70 eV): m/z (%)=326 (3, [M-CO]$^+$), 298 (18, [M-2CO]$^+$], 270 (17, [M-3CO]$^+$), 240 (15), 222 (20), 192 (27), 164 (36), 149 (35), 148 (53), 121 (28), 91 (100, [C$_7$H$_7$]$^+$), 84 (17), 71 (9), 65 (27), 57 (17), 56 (85, [Fe]$^+$).

HR-MS (DIP-MS, 70 eV): m/z 326.023±0.0013 (calculated ([M-CO]$^+$): m/z 326.0241).

Section II
Carbon Monoxide Release, Cytotoxicity and iNOS Inhibition Assays
General Procedure for Carbon Monoxide Release Measurements (Mb-Assay)

Carbon monoxide release was monitored by the absorption change in the Q-band region of the UV/vis spectra of a solution of horse skeletal myoglobin (Mb) in 0.1 M phosphate buffer (as described, for example, in R. Motterlini, J. E. Clark, R. Foresti, P. Sarathchandra, B. E. Mann, C. J. Green, Circ. Res., 90, pp e17-e24 (2002)). For this purpose, a solution of 30 mg Mb in 15 mL buffer was degassed by bubbling with argon for 10 min, then reduced by addition of an excess of Na$_2$S$_2$O$_4$ and degassed again for 10 min. The concentration was determined by measuring a 1:10 diluted solution and using the following equation:

$$A = \epsilon_\lambda \cdot c \cdot l \text{ with } \epsilon_{408\ nm} = 188000 \text{ L mol}^{-1} \text{ cm}^{-1}$$

To determine the carbon monoxide release properties of a complex, 2.3 mL of the Mb solution were filled into a UV cuvette. A stock solution of a complex in DMSO and a solution of the esterase in phosphate buffer were added under argon before the cell was closed to prevent re-oxidation of the Fe(II) in the Mb solution to Fe(III). The cell was heated to 37° C. in a water bath and the carbon monoxide release monitored over time. For all complexes, carbon monoxide release was measured with and without esterase. Equivalents of the esterase are given relative to the inventive complex.

Example 36

Carbon Monoxide Release from rac-86

The Mb solution (c=88 μM) was reduced by the addition of 22 mg (126.4 μmol, 95 eq) of Na$_2$S$_2$O$_4$ in 0.1 mL buffer. 3.4 mg (12 μmol) of rac-86 were dissolved in 300 μL of DMSO to provide a 0.041 M solution. For the measurement, 6 μL (2.45·10$^{-7}$ mol, 1.2 eq) of this solution were added to 2.3 mL of the Mb solution (2.03·10$^{-7}$ mol, 1 eq) and 70 μL (approximately 0.09 eq) of a solution of 5 mg lipase from *Candida rugosa* in 240 μL buffer.

Figure 2:
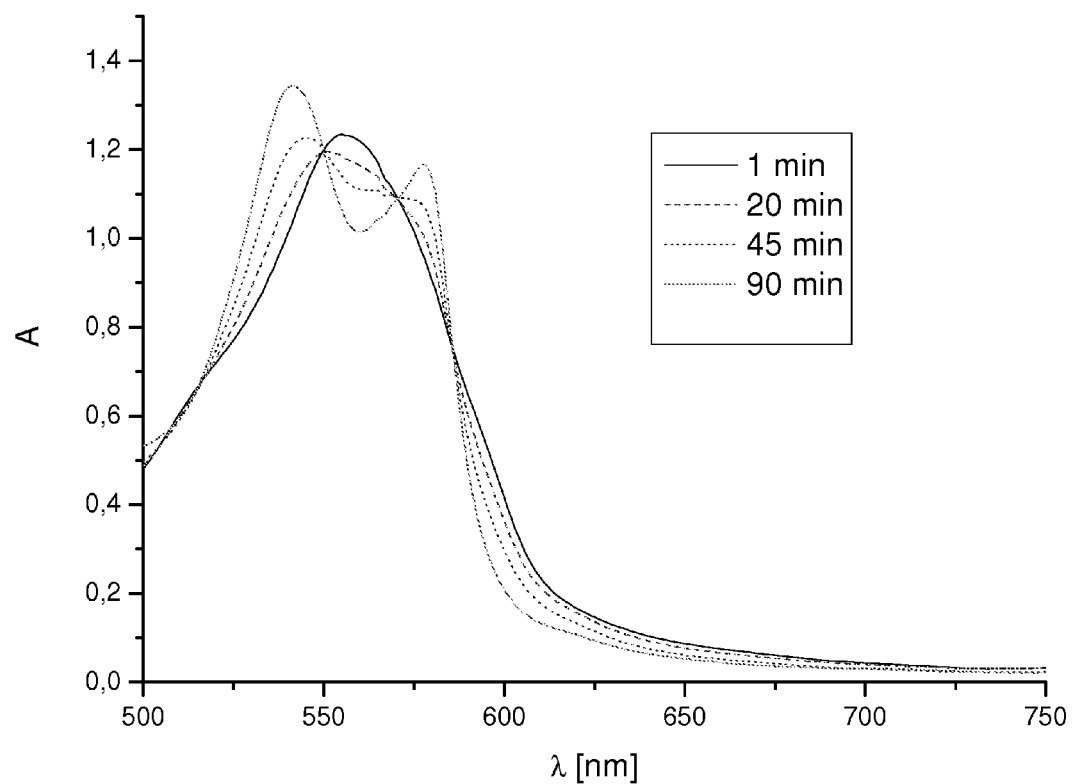
FIG. 2 shows the carbon monoxide release from (RS)-[$\eta$4-Cyclohexa-1,5-dienyl-tricarbonyliron(0)]acetate (rac-86) with lipase *Candida rugosa*.
Figure 3:
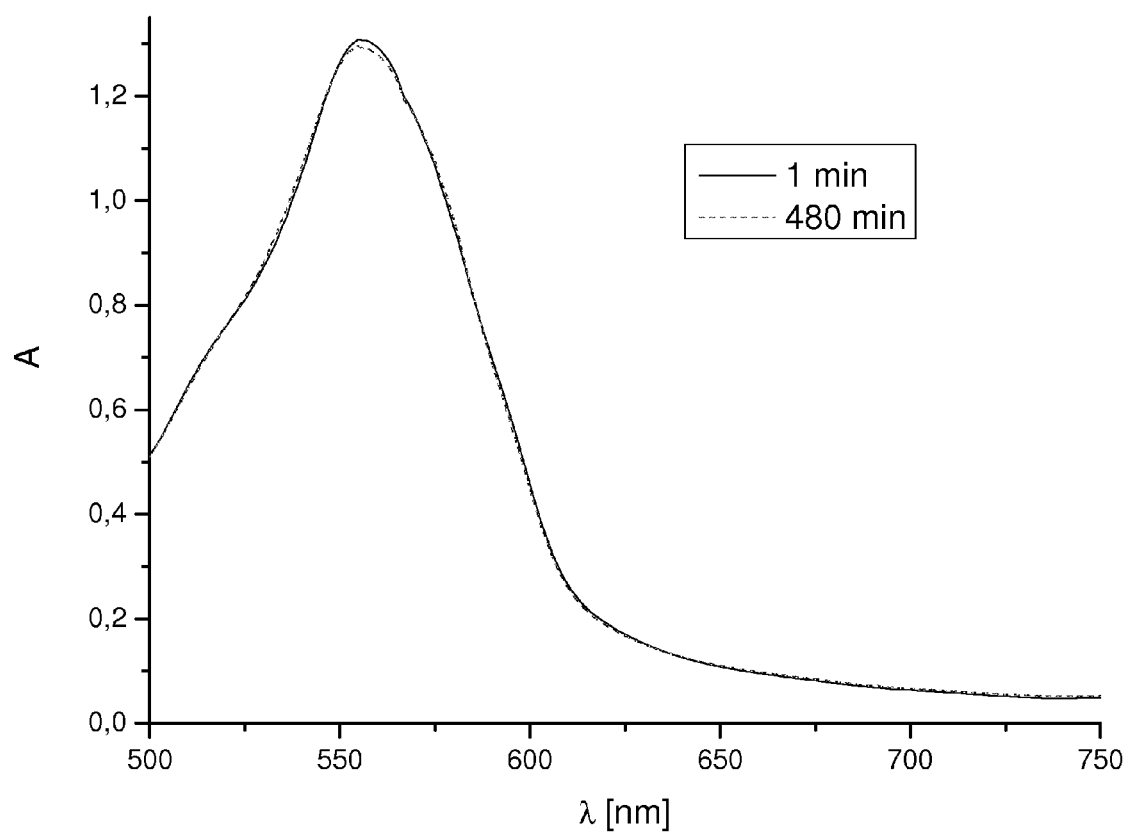
FIG. 3 shows that no carbon monoxide was released from (RS)[$\eta$4-Cyclohexa-1,5-dienyl-tricarbonyliron(0)]acetate (rac-86) without lipase.

FIG. 2 shows the carbon monoxide release from rac-86 with lipase from *Candida rugosa*. FIG. 3 shows that without lipase, no carbon monoxide release from rac-86 was detected.

Example 37

Carbon Monoxide Release from rac-96

The Mb solution (c=76 μM) was reduced by the addition of 23 mg (132.1 μmol, 116 eq) of Na$_2$S$_2$O$_4$ in 0.1 mL buffer. 1.7 mg (6.2 μmol) of rac-96 were dissolved in 160 μL of DMSO to provide a 0.038 M solution. For the measurement, 6 μL (2.29·10$^{-7}$ mol, 1.3 eq) of this solution were added to 2.3 mL of the Mb solution (1.75·10$^{-7}$ mol, 1 eq) and 70 μL (approximately 0.01 eq) of a solution of 0.7 mg pig liver esterase (PLE) in 240 μL buffer.

Figure 4:
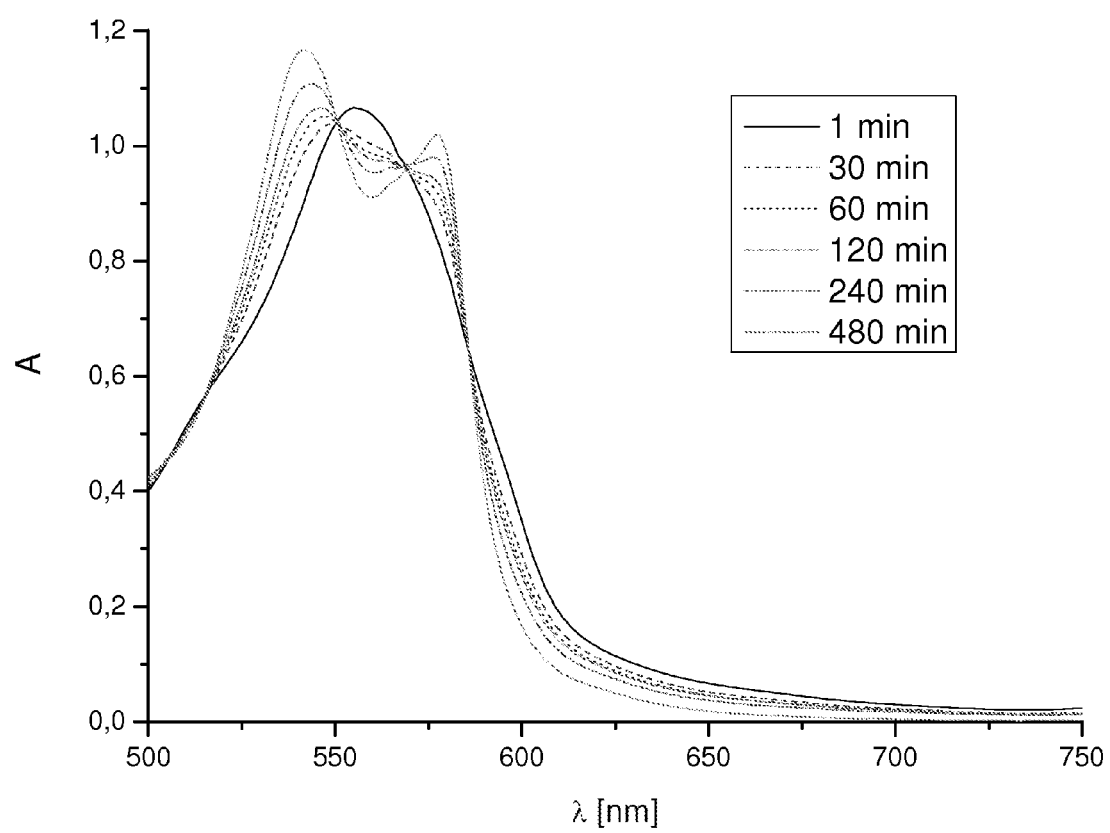
FIG. 4 shows the carbon monoxide release from (RS)-[$\eta$4-Cyclohexa-1,3-dienyl-tricarbonyliron(0)]acetate (rac-86) with pig liver esterase.
Figure 5:
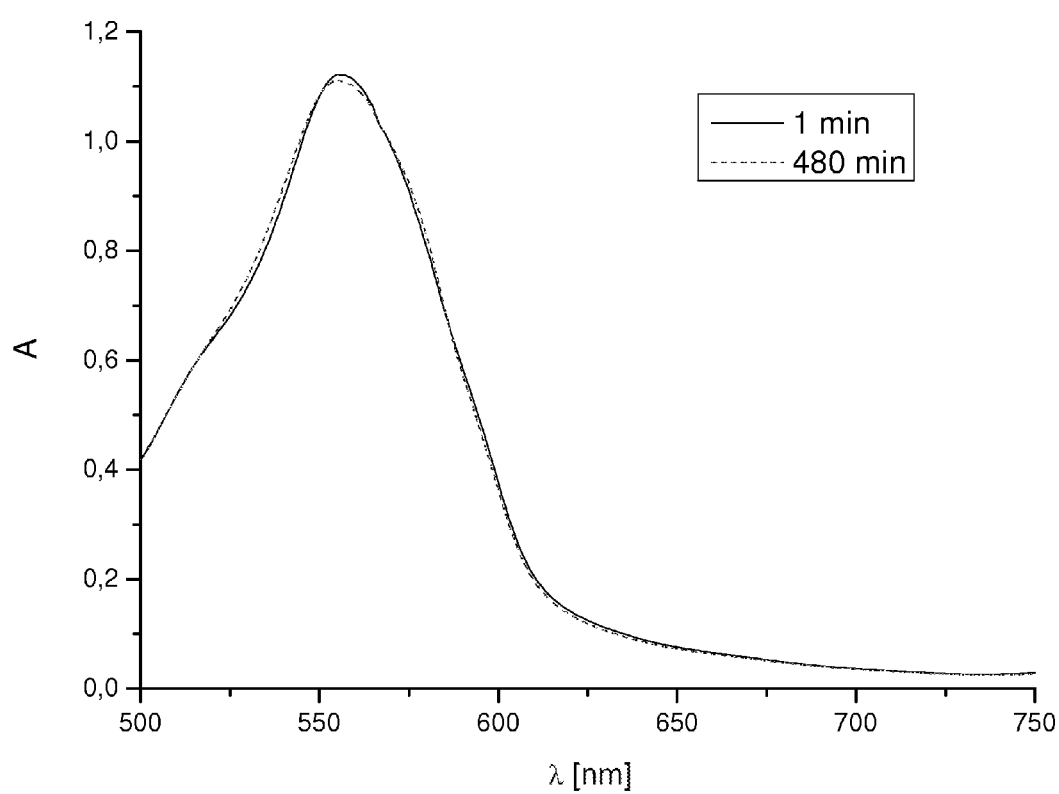
FIG. 5 shows that no carbon monoxide was released from (RS)-[$\eta$4-Cyclohexa-1,3-dienyl-tricarbonyliron(0)]acetate (rac-86) without esterase.

FIG. 4 shows the carbon monoxide release from rac-96 with pig liver esterase. FIG. 5 shows that without esterase, no carbon monoxide release from rac-96 was detected.

Example 38

Carbon Monoxide Release from rac-13

The Mb solution (c=56 μM) was reduced by the addition of 22 mg (126.4 μmol, 151 eq) of Na$_2$S$_2$O$_4$ in 0.1 mL buffer. 1.1 mg (3.0 μmol) of rac-13 were dissolved in 100 μL of DMSO to provide a 0.030 M solution. For the measurement, 3 μL (9.06·10$^{-8}$ mol, 0.7 eq) of this solution were added to 2.3 mL of the Mb solution (1.28·10$^{-7}$ mol, 1 eq) and 70 μL (approximately 0.01 eq) of a solution of 0.6 mg PLE in 240 μL buffer.

Figure 6:
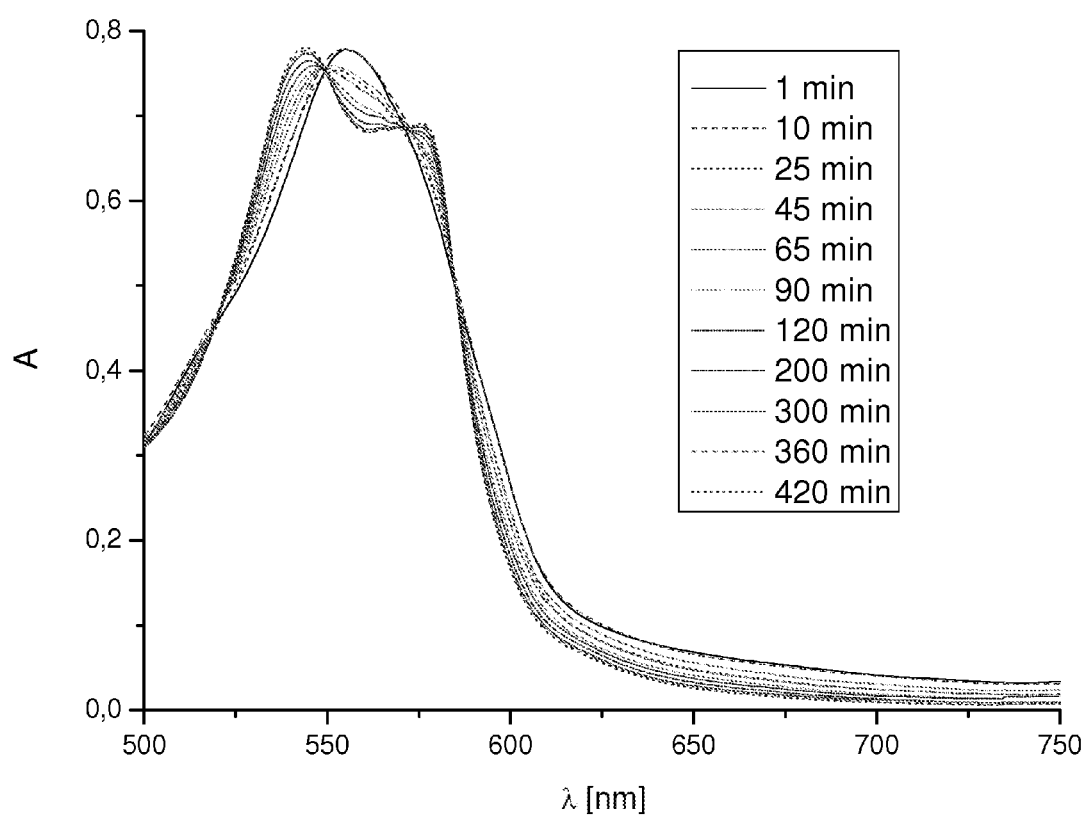
FIG. 6 shows the carbon monoxide release from rac-13 with pig liver esterase.
Figure 7:
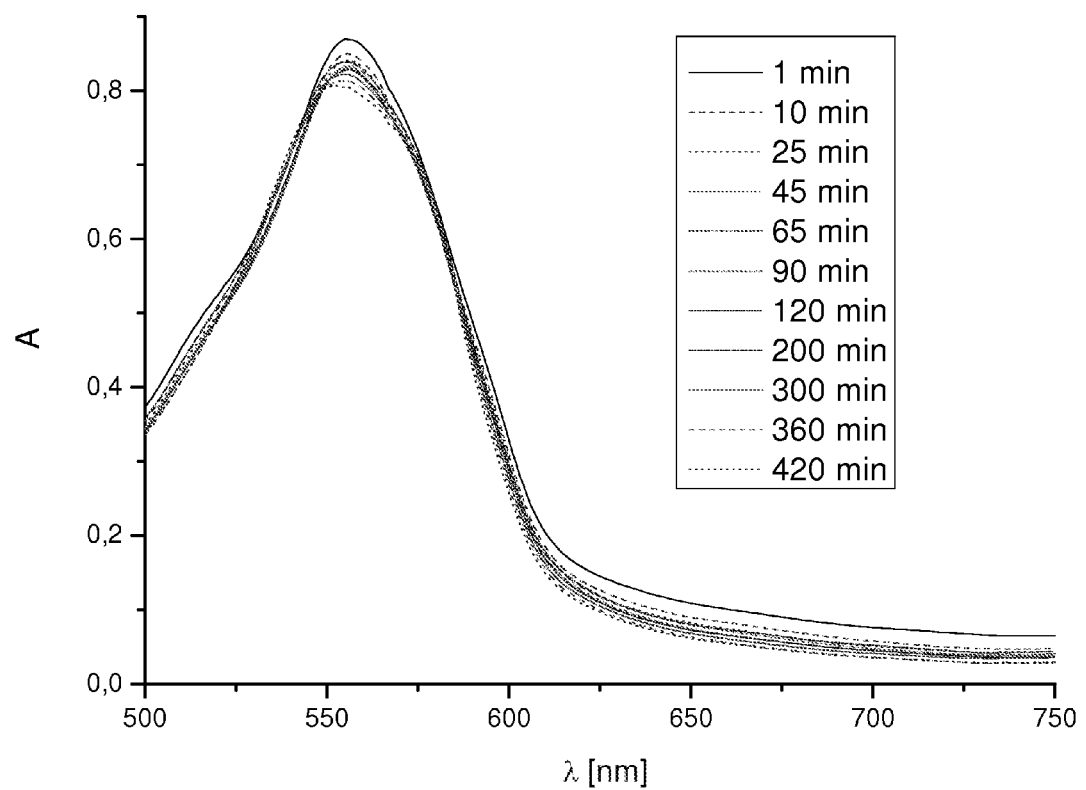
FIG. 7 shows that no significant amount of carbon monoxide was released from rac-13 without esterase.

FIG. 6 shows the carbon monoxide release from rac-13 with pig liver esterase. FIG. 7 shows that without esterase, only very small spectral changes could be detected; i.e., no significant amount of carbon monoxide release could be detected without esterase.

Example 38 shows for the first time that the known complex rac-13 can be enzymatically activated to release carbon monoxide.

Example 39

Carbon Monoxide Release from rac-87

The Mb solution (c=95 μM) was reduced by the addition of 23 mg (132.1 μmol, 92 eq) of Na$_2$S$_2$O$_4$ in 0.1 mL buffer. 1.8 mg (5.6 μmol) of rac-87 were dissolved in 180 μL of DMSO to provide a 0.031 M solution. For the measurement, 12 μL (3.74·10$^{-7}$ mol, 2.2 eq) of this solution were added to 2.3 mL of the Mb solution (2.19·10$^{-7}$ mol, 1 eq) and 140 μL (approximately 0.17 eq) of a solution of 15 mg lipase from *Candida rugosa* in 500 μL buffer. There was no carbon monoxide release in the closed cell, so the cell was opened to air for 2 s after 360 min.

Figure 8:
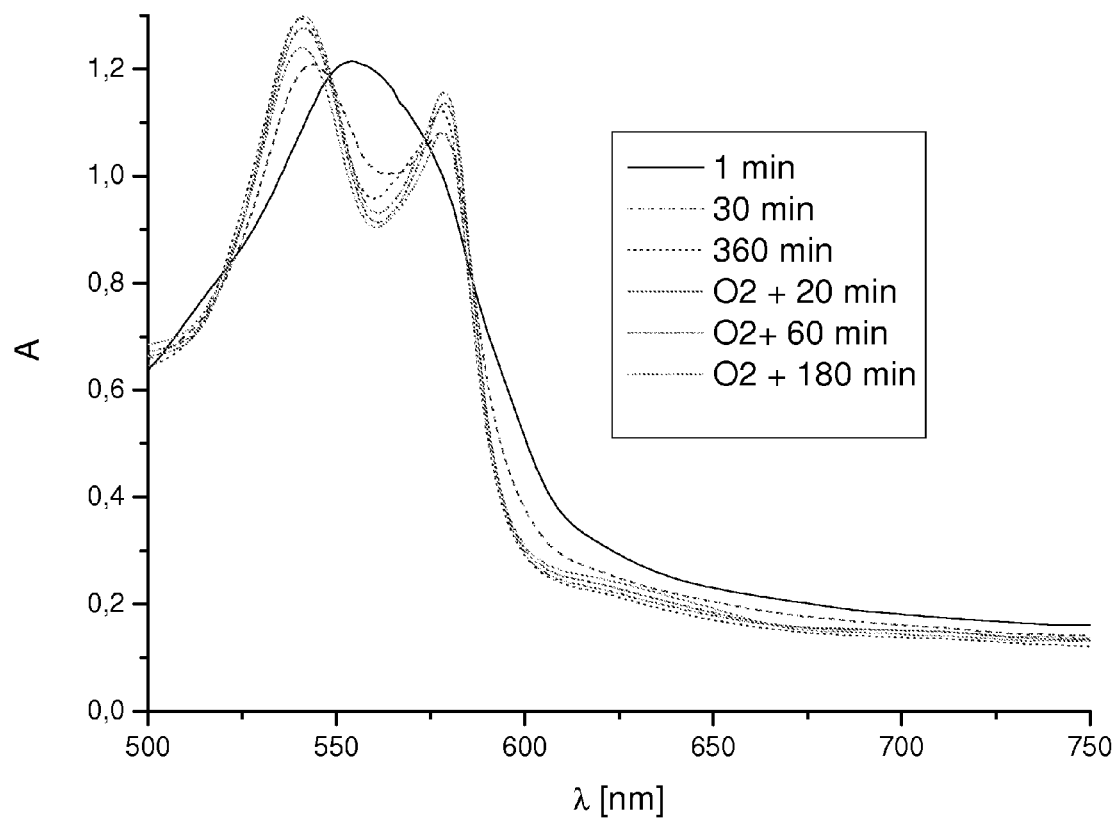
FIG. 8 shows the carbon monoxide release from (RS)-[$\eta^4$-Cyclohexa-1,5-dien-1-yl-tricarbonyliron(0)] pivalate (rac-87) with lipase from *Candida rugosa*.
Figure 9:
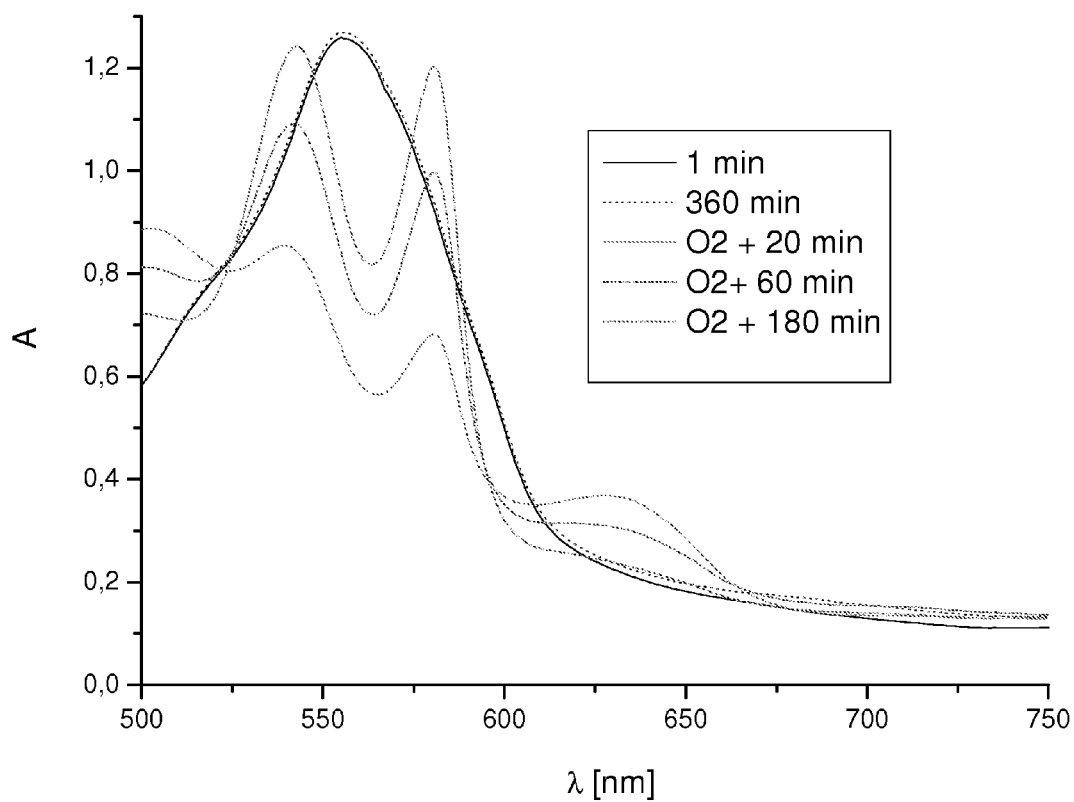
FIG. 9 shows that no carbon monoxide was released from (RS)-[$\eta^4$-Cyclohexa-1,5-dien-1-yl-tricarbonylifon(0)]pivalate (rac-87) without lipase.

FIG. 8 shows the carbon monoxide release from rac-87 with lipase from *Candida rugosa*. FIG. 9 shows that without lipase, no carbon monoxide release from rac-87 was detected. An Mb-O$_2$ species was detected after exposure to air. With lipase from *Candida rugosa*, the conversion of Mb-O$_2$ to MbCO was detected. Without lipase, no carbon monoxide release was detected while oxidation of the Mb solution occurred.

Example 40

Comparative

Carbon Monoxide Release from 2-methoxycyclohexa-1,3-dienetricarbonyliron (0)

The Mb solution (c=93 μM) was reduced by the addition of 22 mg (126.4 μmol, 91 eq) of Na$_2$S$_2$O$_4$ in 0.1 mL buffer. 0.7 mg (2.8 μmol) of 2-methoxycyclohexa-1,3-dienetricarbonyliron (0) were dissolved in 70 μL of DMSO to provide a 0.039 M solution. For the measurement, 6 μL (2.39·10$^{-7}$ mol, 1.3 eq) of this solution were added to 2.3 mL of the Mb solution ($2.14 \cdot 10^{-7}$ mol, 1 eq). There was no carbon monoxide release in the closed cell, so the cell was opened to air for 2 s after 480 min.

Figure 10:
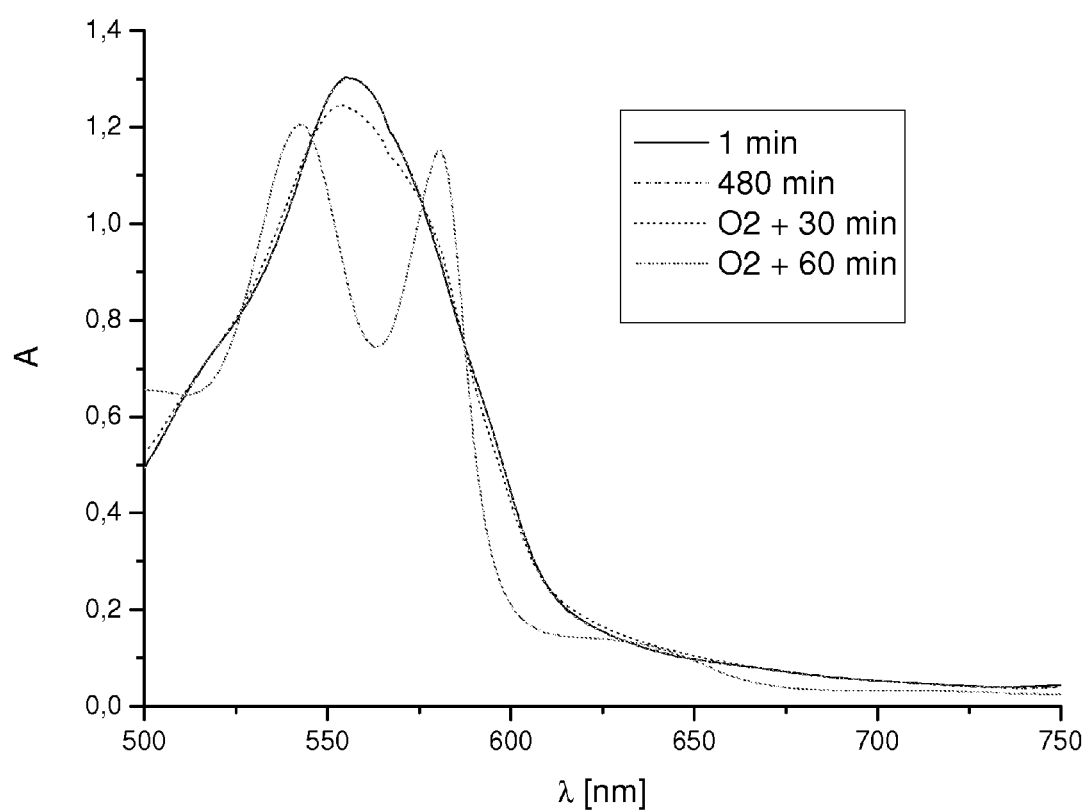
FIG. 10 shows that no carbon monoxide was released from 2-methoxycyclohexa-1,3-diene tricarbonyliron(0) without esterase.
Figure 11:
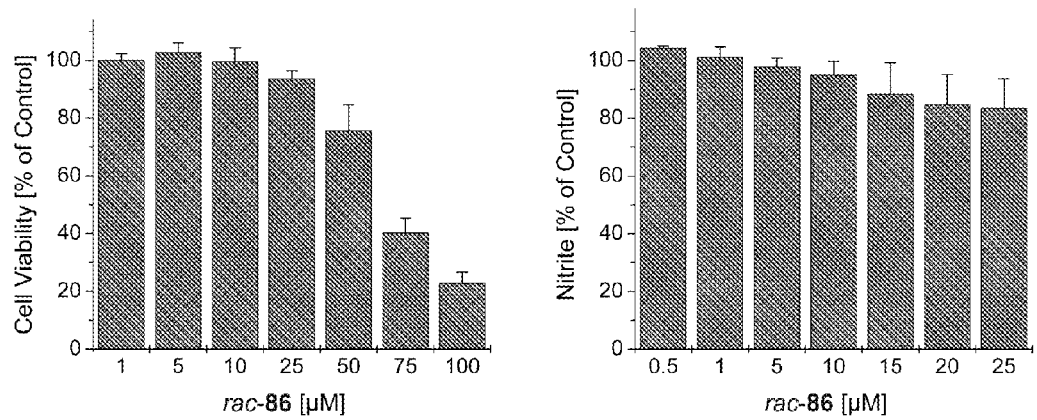
FIG. 11 shows cell viability on the left and nitric oxide production on the right for rac-86.
Figure 12:
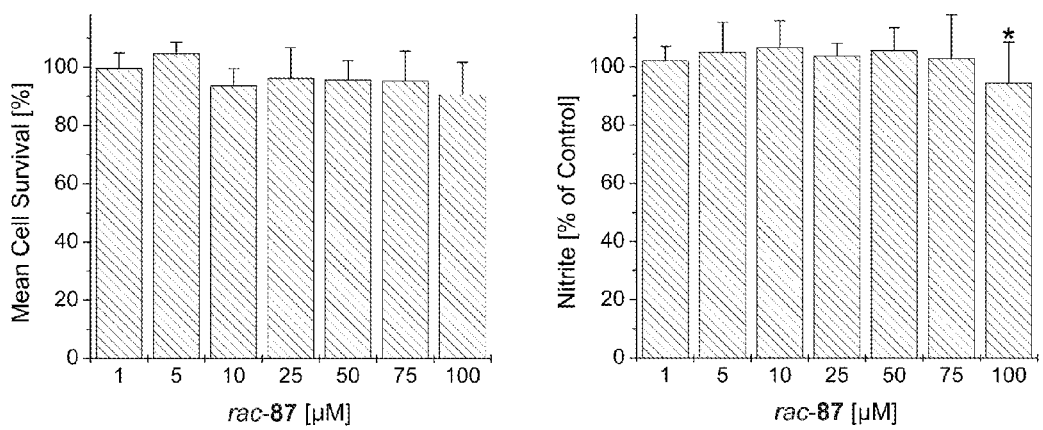
FIG. 12 shows cell viability on the left and nitric oxide production on the right for rac-87.
Figure 13:
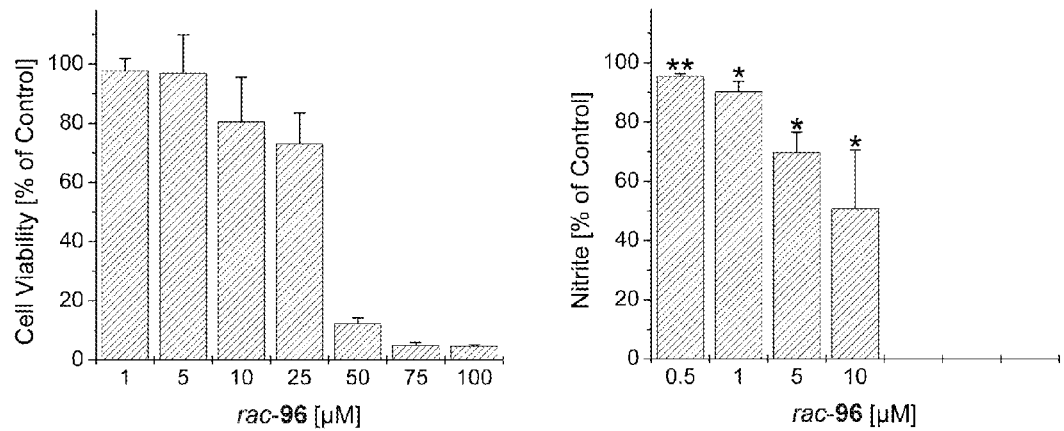
FIG. 13 shows cell viability on the left and nitric oxide production on the right for rac-96.
Figure 14:
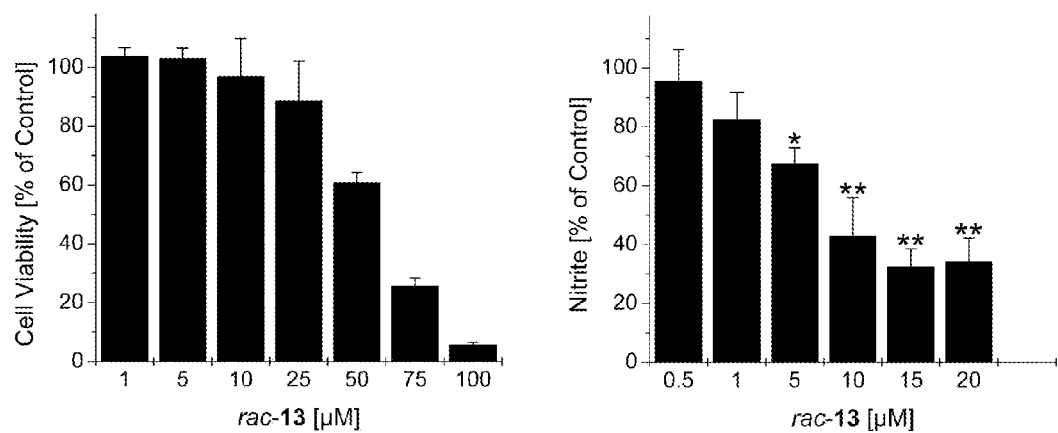
FIG. 14 shows cell viability on the left and nitric oxide production on the right for rac-13.
Figure 15:
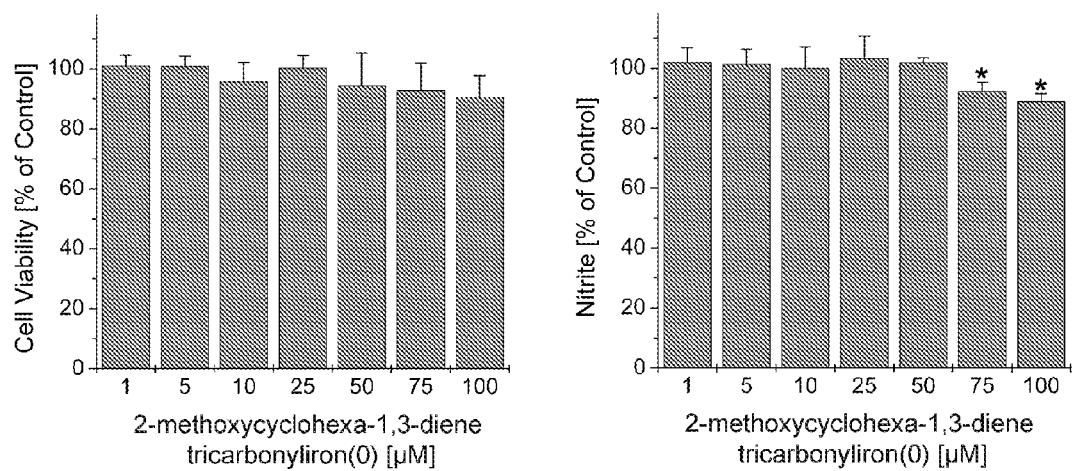
FIG. 15 shows cell viability on the left and nitric oxide production on the right for 2-methoxycyclohexa-1,3-diene tricarbonyliron(0).

FIG. 10 shows that no carbon monoxide was released because the compound has no enzymatically cleavable substituent. Only the Mb-$O_2$ species was therefore detected.

General Procedure I for Studying the Enzymatic Ester Hydrolysis of the Complexes (Kinetic Resolution)

In a Schlenk tube, 36 µmol of the complex and 23 mg (132 µmol, 3.7 eq) of $Na_2S_2O_4$ were dissolved in 0.5 mL of DMSO, and 5 mL of phosphate buffer (0.1 M, pH=7.4) were added. After taking a first sample as the starting point, the enzyme was added and the reaction was monitored by taking samples at certain time intervals. For this purpose, 0.5 mL of the reaction mixture were extracted with 5 mL of a solution of 160 mg of bromobenzene in 100 mL of MtBE. The organic phase was separated, dried over $MgSO_4$ and the solvent was evaporated. The residue was dissolved in n-hexane and the conversion and the enantiomeric excess was determined by chiral HPLC (chiral GC-MS for inventive complex rac-86). Specific inventive complexes were reacted with PLE and lipase from *Candida rugosa*. 2-methoxycyclohexa-1,3-dienetricarbonyliron (0) was reacted with PLE and lipase to provide comparative data.

Table 9 shows which complex is cleaved by which esterase. "+" indicates kinetic racemic resolution, while "−" means that no reaction took place.

TABLE 9

| Enzyme | rac-86 | rac-87 | rac-96 | rac-13 | 2-methoxycyclohexa-1,3-dienetricarbonyliron (0) |
|---|---|---|---|---|---|
| PLE | − | − | + | + | − |
| *Candida rugosa* | + | + | + | − | − |

Table 10 and Table 11 show the results of monitoring the conversion and the enantiomeric excess of the remaining starting material (acyloxy complex). Table 10 shows the inventive reaction of complexes rac-96 and rac-13 with pig liver esterase. Table 11 shows the inventive reaction of complexes rac-86, rac-87 and rac-96 with lipase from *Candida rugosa*. The enantiomeric excess of rac-96 could not be exactly determined, because separation of the enantiomers' base line via HPLC or GC-MS was not successful. Comparative complex 2-methoxycyclohexa-1,3-dienetricarbonyliron (0) did not react with PLE or lipase from *Candida rugosa*.

TABLE 10

| Complex | rac-96 | | rac-13 | |
|---|---|---|---|---|
| m complex (mg) | 10 | | 13 | |
| m enzyme (mg) | 1 | | 0.8 | |
| time (min) | conversion (%)/ee (%) | time (min) | conversion (%)/ee (%) | |
| 0 | 0/5 | 5 | —/10 | |
| 120 | 28/11 | 15 | 3/13 | |
| 180 | 45/17 | 30 | 12/18 | |
| 300 | 52/35 | 45 | 54/27 | |
| 420 | 77/69 | 150 | 64/37 | |
| 540 | 84/73 | 210 | 80/100 | |
| 660 | 89/74 | | | |

TABLE 11

| Complex | rac-86 | rac-87 | rac-87 | rac-96 |
|---|---|---|---|---|
| m complex (mg) | 10 | 11.5 | 12 | 12 |
| m enzyme (mg) | 8 | 8 | 15 | 15 |
| time (min) | conversion (%)/ee (%) | conversion (%)/ee (%) | conversion (%)/ee (%) | conversion (%)/ee (%) |
| 0 | 0/0 | 0/0 | 0/0 | 0/0 |
| 15 | 32/51 | | | 43/20 |
| 30 | 68/75 | 4/2 | | 57/30 |
| 60 | 82/93 | 6/5 | | 76/50 |
| 110 | 93/100 | 8/6 | 47/14 | 83/70 |
| 240 | 98/100 | 12/11 | 60/20 | |
| 24 h | | 47/38 | 73/58 | |

General Procedure II for Studying the Enzymatic Ester Hydrolysis of the Complexes (Kinetic Resolution)

In an open tube, 10 mg (35.966 µmol) of the complex were dissolved in 0.5 mL of DMSO and 5 mL of phosphate buffer (0.1 M, pH=7.4) were added. After taking a first sample as a starting point, the enzyme was added and the reaction monitored by taking samples over a certain time. From time to time, samples of 0.5 mL were taken and extracted with 5 mL of a solution of 160 mg of bromobenzene in 100 mL of MtBE. The organic phase was separated, dried over $MgSO_4$ and the solvent evaporated. The residue was dissolved in n-hexane and the conversion and the enantiomeric excess were determined by chiral HPLC (chiral GC-MS for complex rac-86). The enantiomeric excess of rac-96 could not be exactly determined, because it was not possible to base-line separate the enantiomers through HPLC or GC-MS.

Table 12 shows the conversion and enantiomeric excess for the enzymatic reactions (kinetic enzymatic resolution of rac-86 and rac-96).

TABLE 12

| Complex | rac-86 | | rac-96 | |
|---|---|---|---|---|
| m complex (mg) | 10 | | 10 | |
| m lipase from *Candida rugosa* (mg) | 20 mg | | 20 mg | |
| time (min) | conversion (%)/ee (%) | time (min) | conversion (%)/ee (%) | |
| 0 | 0/0 | 0 | 0/0 | |
| 15 | 60/62 | 15 | 65**/43 | |
| 30 | 79/67 | 30 | 77/71 | |
| 60 | 85/70 | 60 | 79/96 | |
| 110 | 97/70 | 110 | 81/100 | |

**corrected value.

Cells and Cell Culture

The murine macrophage cell line RAW264.7 (as described, for example, in W. C. Raschke, S. Baird, P. Ralphm, I. Nakoinz, Cell, 15, pp 261-267 (1978)) was kept under standard cell culture conditions using RPMI 1640 with 10% heat-inactivated fetal calf serum (FCS) and 2 mM glutamine (Invitrogen, Karlsruhe, Germany).

Determination of Cell Viability by MTT Assay

Cell viability was evaluated by MTT assays as described, for example, in T. Mosmann: J. Immunol. Methods, 65, pp 55-63 (1983). This assay is based upon the conversion of the yellow MTT (3-(4,5-dimethylthiazol-2-yl)-2,5-diphenyltetrazoliumbromid) by mitochondrial dehydrogenases to a violet formazan dye, which can then be photometrically quantified.

Cells were thereby seeded in 96-well plates at a density of $5 \times 10^3$ per well and cultured for 24 h. The cells were then incubated for another 24 h with a medium supplemented with complexes and 10 ng/mL LPS (*Escherichia coli* serotype 111:B4, Sigma). Controls received only culture medium with LPS, or solvent and LPS, respectively.

Supernatants were then removed and 100 µL MTT solution (0.4 mg/mL in culture medium) was added to each well. The cells were incubated for another 3 h at 37° C. Subsequently, 100 µl of a SDS-solution (10% in phosphate buffered saline) was added, and the formazan crystals were allowed to dissolve overnight. Absorbance was determined with a multi-well plate photometer (TiterTek) at 560 nm.

Determination of Cell Proliferation by Crystal Violet Staining

Crystal violet is used to stain the nuclei of cells. The photometrically measured intensity of the dye thereby directly correlates with the number of cells as is described, for example, in R. Gillies, N. Didier, M. Denton, Anal. Biochem, 159, pp 109-113 (1986).

According to the MTT assays, cells were seeded in 96-well plates at a density of $5 \times 10^3$ per well and cultured for 24 h. The cells were then incubated for another 24 h with medium supplemented with the complexes and 10 ng/mL LPS (*Escherichia coli* serotype 111:B4, Sigma). Controls received only culture medium with LPS, or solvent and LPS, respectively.

Supernatants were then removed and the cells were stained with 30 µL crystal violet solution (0.5% crystal violet in 20% methanol) per well for 10 min. The crystal violet solution was removed, and the cells were washed twice with 200 µL water and then air-dried overnight. Crystal violet was then solubilized by adding 100 µL EtOH/Na-Citrate-solution (EtOH+ 0.1 M Na-citrate, (v/v) 1:1) per well. The absorbance was then determined at 560 nm.

Measurement of Nitrite Production by Griess Assay

The generation of nitric oxide (NO) was determined by measuring the accumulation of nitrite in the cell culture medium by a microplate assay method based on the Griess reaction and performed as described, for example, in E. Park, M. R. Quinn, J. Leukoc. Biol., 54, pp 119-124 (1993).

Cells were thereby seeded in 96-well plates at a density of $8 \times 10^4$ per well and cultured for 24 h. The cells were then incubated for another 24 h with a medium supplemented with the complexes and 10 ng/mL LPS (*Escherichia coli* serotype 111:B4). Controls received only culture medium with LPS, or solvent and LPS, respectively. A volume of 100 µl culture supernatant was then mixed with 100 µl Griess reagent (1% sulfanilamide, 0.1% naphthylethylene-diamine dihydrochloride in 2% phosphoric acid). After a 15 min incubation at room temperature, the absorbance was determined at 560 nm. The nitrite content was determined by using sodium nitrite as a standard.

FIGS. 11-15 show the results of the in vitro assays performed with RAW264.7 cells stimulated with 10 ng/mL of LPS for complexes rac-86, rac-87, rac-96 and rac-13 and comparative complex 2-methoxycyclohexa-1,3-dienetricarbonyliron (0), respectively. Charts on the left show cell viability as a percentage of the control as determined by MTT tests or, in the case of rac-87, acrystal violet assay, after an incubation time of 24 h at various concentrations. Charts on the right show the influence of complexes on nitric oxide production as a percentage of the control as determined by a Griess assay. The data set forth represents three independent experiments performed in quadruplicates. Levels of significance: * $p \leq 0.05$,  $p \leq 0.01$, * $p \leq 0.001$.

Experiments were carried out with four parallels and repeated independently at least three times. Results are expressed as mean±SD and are depicted as a percentage of untreated controls. A sigmoidal logistic function was used to fit dose-response curves and to determine $IC_{50}$ and $IC_{20}$ values, using an excel calculation sheet (Ed50plus, MH Vargas). Statistical analysis was performed using the software Prism (GraphPad Software). Quantitative data was tested with a two-tailed Student's t-test referring to the untreated control. Levels of significance: $p < 0.05$ (*), $p < 0.01$ (), $p < 0.001$ (*).

Although the present invention has been described and illustrated with reference to specific embodiments thereof, it is not intended that the present invention be limited to those illustrative embodiments. Those skilled in that art will recognize that variations and modifications can be made without departing from the true scope of the present invention as defined by the claims that follow. It is therefore intended to include within the present invention all such variations and modifications as fall within the scope of the appended claims and equivalents thereof.

What is claimed is:

1. A $\eta^4$-1,3-diene-Fe(CO)$_3$ complex having the formula (I):

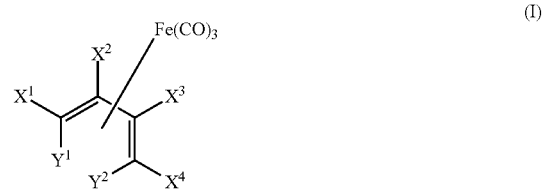

where,
$X^1$, $X^2$, $X^3$, $X^4$, $Y^1$ and $Y^2$ are, independently of each other, H, halogen, $N_3$, cyano, alkyl, alkenyl, alkynyl, aryl, hetero-aryl, alkoxy, aryloxy, alkylsulfido, arylsulfido, alkylamino, arylamino, acyl, alkoxylcarbonyl, acylsulfanyl, acyloxy (—OC(=O)R$^1$, acylamino (—N(R$^2$)C(=O) R$^3$ or phosphoryloxy (OP(=O)(R$^4$)(R$^5$), wherein,
R$^1$ is H, alkyl, alkenyl, alkynyl, aryl, hetero-aryl, alkoxy, aryloxy, alkylamino, arylamino, alkylacyl, or arylacyl,
R$^2$ and R$^3$ are, independently of each other, H, alkyl, alkenyl, alkynyl, aryl, hetero-aryl, alkoxy, aryloxy, alkylamino, arylamino, alkylacyl, or arylacyl,
R$^4$ and R$^5$ are, independently of each other, OH, O$^-$ (as a salt), H, alkyl, alkenyl, alkynyl, aryl, hetero-aryl, alkoxy, aryloxy, alkylamino, arylamino,
each of the alkyl, the alkenyl, the alkylnyl, the aryl, the hetero-aryl, the alkoxy, the aryloxy, the alkylsulfido, the arylsulfido, the alkylamino, the arylamino, the acyl and the acylsulfanyl can be substituted by at least one of alkyl, alkenyl, alkynyl, aryl, heteroaryl, alkoxy, aryloxy, acyl, hydroxy, amino, alkylamino, arylamino, halogeno, azido, oxo, imino, cyano and sulfanyl, two or more of $X^1, X^2, X^3, X^4, Y^1$ and $Y^2$ may be connected to form a cyclic or polycyclic structure with an overall ring size of 5 to 20, at least one of $X^1, X^2, X^3, X^4, Y^1$ and $Y^2$ must be at least one of acyloxy (—OC(=O)$R^1$) and phosphoryloxy (OP(=O)($R^4$)($R^5$)), wherein each of $R^1, R^4$ and $R^5$ have the meaning as defined above, and the following complexes are specifically excluded:

a) complexes having the formula (II):

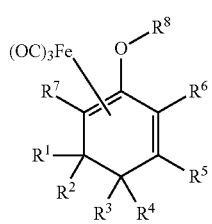

(II)

wherein $R^1, R^2, R^3, R^4, R^5, R^6, R^7$ and $R^8$ are, with respect to complexes 1-15, as set forth in Table 1:

TABLE 1

| No. | $R^1$ | $R^2$ | $R^3$ | $R^4$ | $R^5$ | $R^6$ | $R^7$ | $R^8$ |
|---|---|---|---|---|---|---|---|---|
| 1 | H | H | $CH_3$ | $CH_3$ | H | H | H | COMe |
| 2 | H | H | $CH_3$ | $CH_3$ | H | H | H | P(O)(OEt)$_2$ |
| 3 | H | H | $CH_3$ | $CH_3$ | H | H | H | P(O)(Oi-Pr)$_2$ |
| 4 | H | H | $CH_3$ | $CH_3$ | H | H | H | P(O)(OPh)$_2$ |
| 5 | H | H | $CH_3$ | $CH_3$ | H | H | H | P(O)(NMe$_2$)$_2$ |
| 6 | H | H | H | H | $CH_3$ | H | H | P(O)(OEt)$_2$ |
| 7 | $CH_3$ | H | H | H | $CH_3$ | H | H | P(O)(OEt)$_2$ |
| 8 | $CH_3$ | $CH_3$ | H | H | $CH_3$ | H | H | P(O)(OEt)$_2$ |
| 9 | H | H | H | H | H | H | H | P(O)(OEt)$_2$ |
| 10 | H | H | H | H | H | H | H | R* |
| 11 | H | H | H | H | H | H | H | ent-R* |
| 12 | H | H | H | H | OAc | H | H | COMe |
| 13 | $CH_3$ | $CH_3$ | H | H | OAc | H | H | COMe |
| 14 | H | H | $CH_3$ | H | H | H | H | R* |
| 15 | H | H | $CH_3$ | H | H | H | H | ent-R* | b) complexes having the formula (III):

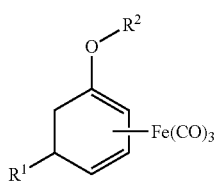

(III)

wherein $R^1$ and $R^2$ are, with respect to complexes 16-18, as set forth in Table 2:

TABLE 2

| No | $R^1$ | $R^2$ |
|---|---|---|
| 16 | H | R* |
| 17 | H | ent-R* |
| 18 | $CH_3$ | COMe | c) complexes having the formula (IV):

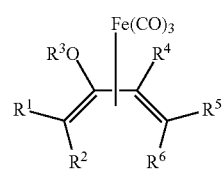

(IV)

wherein $R^1, R^2, R^3, R^4, R^5$ and $R^6$ are, with respect to complexes 19-29, as set forth in Table 3:

TABLE 3

| No. | $R^1$ | $R^2$ | $R^3$ | $R^4$ | $R^5$ | $R^6$ |
|---|---|---|---|---|---|---|
| 19 | $CH_3$ | H | P(O)(OEt)$_2$ | H | $C_6H_5$ | H |
| 20 | $CH_3$ | H | P(O)(OEt)$_2$ | H | $CH_3$ | H |
| 21 | H | H | P(O)(OEt)$_2$ | H | H | H |
| 22 | H | H | P(O)(OEt)$_2$ | H | i-Pr | H |
| 23 | H | H | P(O)(OEt)$_2$ | H | $C_6H_5$ | H |
| 24 | H | H | COMe | H | H | H |
| 25 | H | H | COPh | H | H | H |
| 26 | H | H | R* | H | i-Pr | H |
| 27 | H | H | R* | H | $C_6H_5$ | H |
| 28 | H | H | ent-R* | H | i-Pr | H |
| 29 | H | H | ent-R* | H | $C_6H_5$ | H | d) complexes having the formula (V):

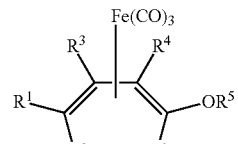

(V)

wherein $R^1, R^2, R^3, R^4, R^5$ and $R^6$ are, with respect to complexes 30-36, as set forth in Table 4:

TABLE 4

| No. | $R^1$ | $R^2$ | $R^3$ | $R^4$ | $R^5$ | $R^6$ |
|---|---|---|---|---|---|---|
| 30 | H | $CO_2Me$ | H | H | COMe | H |
| 31 | H | COMe | H | H | COME | H |
| 32 | H | COPh | H | H | COME | H |
| 33 | H | H | H | H | COMe | H |
| 34 | H | H | H | H | COPh | H |
| 35 | $CH_3$ | H | H | H | R* | H |
| 36 | $CH_3$ | H | H | H | ent-R* | H | e) complexes having the formula (VI):

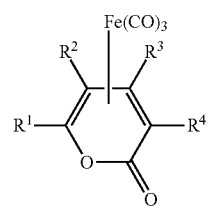

(VI)

wherein $R^1$, $R^2$, $R^3$ and $R^4$ are, with respect to complexes 37-46, as set forth in Table 5:

TABLE 5

| No. | $R^1$ | $R^2$ | $R^3$ | $R^4$ |
|---|---|---|---|---|
| 37 | H | H | H | H |
| 38 | CH₃ | H | Cl | H |
| 39 | CH₃ | H | CH₃ | H |
| 40 | CH₃ | H | I | H |
| 41 | H | H | Cl | H |
| 42 | CH₃ | H | H | H |
| 43 | CH₃ | H | Br | H |
| 44 | H | Br | H | H |
| 45 | H | C₆H₅ | H | H |
| 46 | H | C₆H₅-4-OMe | H | H | f) complexes having the formula (VII):

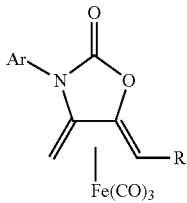

(VII)

wherein Ar and R are, with respect to complexes 47-63, as set forth in Table 6:

TABLE 6

| No. | Ar | R |
|---|---|---|
| 47 | C₆H₅ | H |
| 48 | C₆H₅ | H |
| 49 | C₆H₅ | H |
| 50 | C₆H₄-2-Me | H |
| 51 | C₆H₄-4-Me | H |
| 52 | C₆H₄-3-Cl | H |
| 53 | C₆H₄-4-Cl | H |
| 54 | C₆H₅ | Me |
| 55 | C₆H₄-2-Me | Me |
| 56 | C₆H₄-4-Me | Me |
| 57 | C₆H₄-3-Cl | Me |
| 58 | C₆H₄-4-Cl | Me |
| 59 | C₆H₅ | Et |
| 60 | C₆H₄-2-Me | Et |
| 61 | C₆H₄-4-Me | Et |
| 62 | C₆H₄-3-Cl | Et |
| 63 | C₆H₄-4-Cl | Et | g) complexes having the formula (VIII):

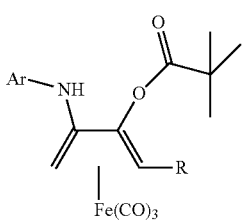

(VIII)

wherein Ar and R are, with respect to complexes 64-67, as set forth in Table 7:

TABLE 7

| No. | Ar | R |
|---|---|---|
| 64 | C₆H₅ | H |
| 65 | C₆H₅ | Me |
| 66 | C₆H₄-4-Cl | Me |
| 67 | C₆H₅ | Et | h) complexes having the formula (X):

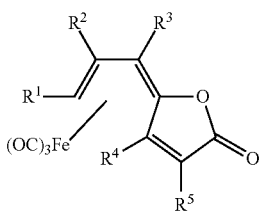

(X)

wherein $R^1$, $R^2$, $R^3$, $R^4$ and $R^5$ are, with respect to complexes 68-70, as set forth in Table 8:

TABLE 8

| Nr. | $R^1$ | $R^2$ | $R^3$ | $R^4$ | $R^5$ |
|---|---|---|---|---|---|
| 68 | H | C₆H₅ | C₆H₅ | C₆H₅ | C₆H₅ |
| 69 | C₆H₅ | H | t-Bu | C₆H₅ | CO₂Et |
| 70 | C₆H₅ | H | t-Bu | C₆H₅ | SO₂Me | and i) complexes 71-73 below:

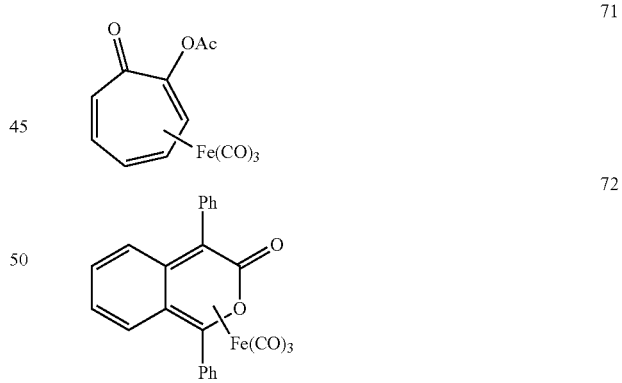

wherein for complexes 1-73, Ac is acetyl, Bu is butyl, Me is methyl, Et is Ethyl, NME is N-methylamide, i-Pr is isopropyl, Pr is propyl, Ph is phenyl, R* is a substituent of the formula

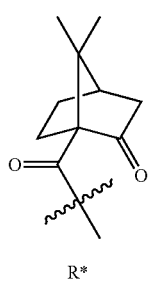 [SMILES: *C(=O)C12CCC(CC1=O)C2(C)C]

R* and ent-R* is an enantiomer of R*.

2. The complex as recited in claim 1, wherein in formula (I), $Y^1$ and $Y^2$ are connected to each other to form a carbocyclic or a heterocyclic ring with a ring size of 5 to 20.

3. The complex as recited in claim 1, wherein formula (I) includes stereoisomers and enantiomers arising from the complexation of non-symmetric diene ligands.

4. The complex as recited in claim 1, wherein the complex is at least one of complexes 80 to 99 and stereoisomers thereof:

80

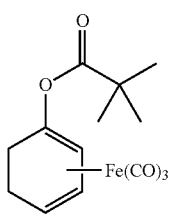

81

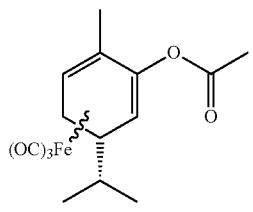

82

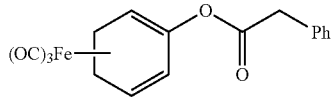

83

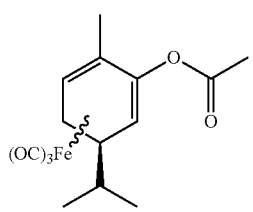

84

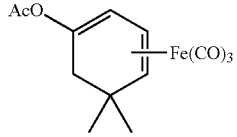

85

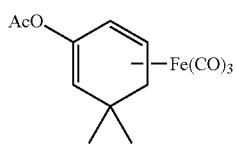

86

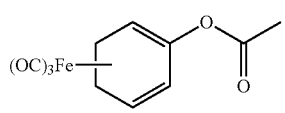

87

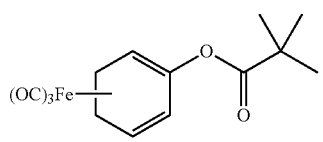

88

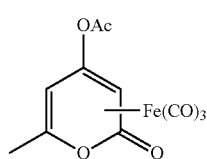

89

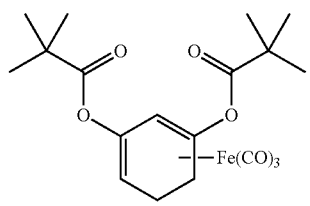

90

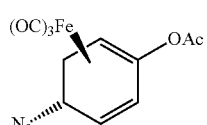

91

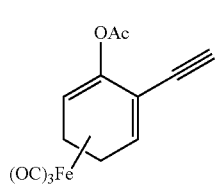

92

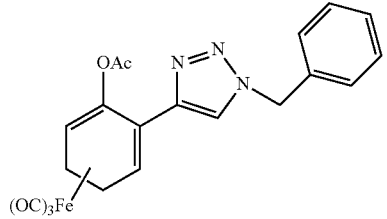

93

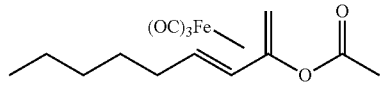

94

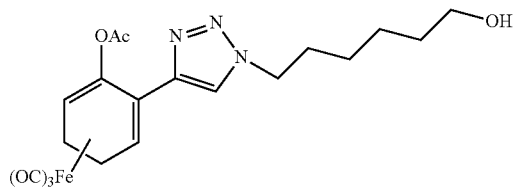

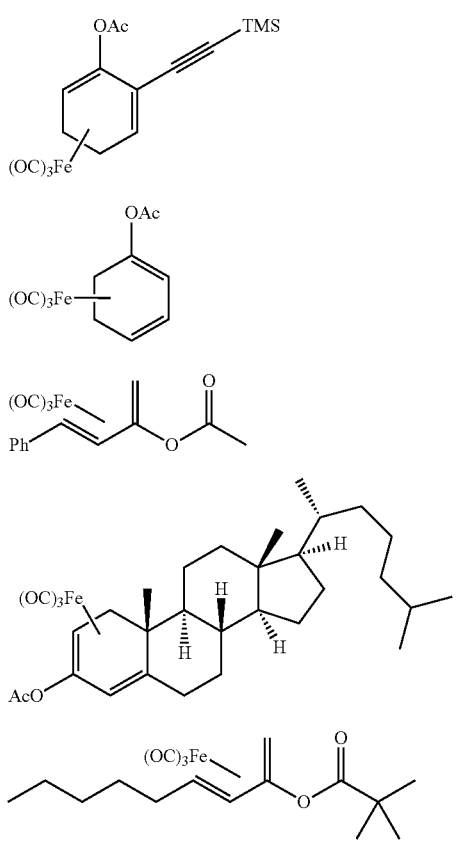

wherein Ph is phenyl, Ac is acetyl and TMS is trimethylsilyl.

5. A method of manufacturing the complex recited in claim 1, the method comprising at least one of methods a) to e):
a) providing a dienylester ligand;
   providing a Fe(CO)$_3$ transfer reagent; and
   complexing the dienylester ligand with the Fe(CO)$_3$ transfer reagent to obtain the complex;
b) providing an intermediate dienol-Fe(CO)$_3$ complex; and
   at least one of acylating and phosphorylating the intermediate dienol-Fe(CO)$_3$ complex to obtain the complex;
c) providing an intermediate acyloxy-diene complex; and
   transesterifying the intermediate acyloxy-diene complex to obtain the complex;
d) providing an acyl- or phosphoryloxy-substituted cationic pentadienyl-Fe(CO)$_3$ complex; and
   reacting the acyl- or phosphoryloxy-substituted cationic pentadienyl-Fe(CO)$_3$ with a nucleophile to obtain the complex; and
e) providing an intermediate acyloxy- or phosphoryloxy-diene-Fe(CO)$_3$ complex substituted with a reactive functional group; and
   further reacting the intermediate acyloxy- or phosphoryloxy-diene-Fe(CO)$_3$ complex substituted with a reactive functional group to obtain the complex.

6. The method as recited in claim 5, wherein the dienylester ligand in a) is an acyloxy-diene or phosphoryloxydiene.

7. The method as recited in claim 5, wherein the intermediate dienol-Fe(CO)$_3$ complex in b) is a complex having the formula (I):

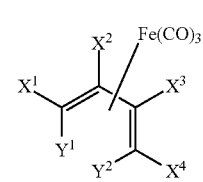

where,
  $X^1$, $X^2$, $X^3$, $X^4$, $Y^1$ and $Y^2$ are, independently of each other, H, halogen, $N_3$, cyano, alkyl, alkenyl, alkynyl, aryl, hetero-aryl, alkoxy, aryloxy, alkylsulfido, arylsulfido, alkylamino, arylamino, acyl, alkoxylcarbonyl, acylsulfanyl, acyloxy (—OC(=O)R$^1$, acylamino (—N(R$^2$)C(=O)R$^3$ or phosphoryloxy (OP(=O)(R$^4$)(R$^5$),
wherein,
  R$^1$ is H, alkyl, alkenyl, alkynyl, aryl, hetero-aryl, alkoxy, aryloxy, alkylamino, arylamino, alkylacyl, or arylacyl,
  R$^2$ and R$^3$ are, independently of each other, H, alkyl, alkenyl, alkynyl, aryl, hetero-aryl, alkoxy, aryloxy, alkylamino, arylamino, alkylacyl, or arylacyl,
  R$^4$ and R$^5$ are, independently of each other, OH, O$^-$ (as a salt), H, alkyl, alkenyl, alkynyl, aryl, hetero-aryl, alkoxy, aryloxy, alkylamino, arylamino,
  each of the alkyl, the alkenyl, the alkylnyl, the aryl, the hetero-aryl, the alkoxy, the aryloxy, the alkylsulfido, the arylsulfido, the alkylamino, the arylamino, the acyl and the acylsulfanyl can be substituted by at least one of alkyl, alkenyl, alkynyl, aryl, heteroaryl, alkoxy, aryloxy, acyl, hydroxy, amino, alkylamino, arylamino, halogeno, azido, oxo, imino, cyano and sulfanyl,
  two or more of $X^1$, $X^2$, $X^3$, $X^4$, $Y^1$ and $Y^2$ may be connected to form a cyclic or polycyclic structure with an overall ring size of 5 to 20, and
  at least one of $X^1$, $X^2$, $X^3$, $X^4$ is OH,
or the intermediate acyloxy-diene complex in c) is a complex having the formula (I):

(I)

where,
  $X^1$, $X^2$, $X^3$, $X^4$, $Y^1$ and $Y^2$ are, independently of each other, H, halogen, $N_3$, cyano, alkyl, alkenyl, alkynyl, aryl, hetero-aryl, alkoxy, aryloxy, alkylsulfido, arylsulfido, alkylamino, arylamino, acyl, alkoxylcarbonyl, acylsulfanyl, acyloxy (—OC(=O)R$^1$, acylamino (—N(R$^2$)C(=O)R$^3$ or phosphoryloxy (OP(=O)(R$^4$)(R$^5$),
wherein,
  R$^1$ is H, alkyl, alkenyl, alkynyl, aryl, hetero-aryl, alkoxy, aryloxy, alkylamino, arylamino, alkylacyl, or arylacyl,
  R$^2$ and R$^3$ are, independently of each other, H, alkyl, alkenyl, alkynyl, aryl, hetero-aryl, alkoxy, aryloxy, alkylamino, arylamino, alkylacyl, or arylacyl,
  R$^4$ and R$^5$ are, independently of each other, OH, O$^-$ (as a salt), H, alkyl, alkenyl, alkynyl, aryl, hetero-aryl, alkoxy, aryloxy, alkylamino, arylamino, each of the alkyl, the alkenyl, the alkylnyl, the aryl, the hetero-aryl, the alkoxy, the aryloxy, the alkylsulfido, the arylsulfido, the alkylamino, the arylamino, the acyl and the acylsulfanyl can be substituted by at least one of alkyl, alkenyl, alkynyl, aryl, heteroaryl, alkoxy, aryloxy, acyl, hydroxy, amino, alkylamino, arylamino, halogeno, azido, oxo, imino, cyano and sulfanyl, two or more of $X^1, X^2, X^3, X^4, Y^1$ and $Y^2$ may be connected to form a cyclic or polycyclic structure with an overall ring size of 5 to 20, and at least one of $X^1, X^2, X^3, X^4$ contains at least one of acyloxy ($-OC(=O)R^1$).

8. The method as recited in claim 5, wherein the reactive functional group in e) with which the intermediate acyloxy- or phosphoryloxy-diene-Fe(CO)$_3$ complex is substituted is at least one of an alkynyl, a carboxyl, a ketone, an aldehyde, an amino, an azido and a hydroxy group.

9. A kit for producing a pharmaceutical solution, the kit comprising the complex as recited in claim 1 in solid form as an active ingredient and a pharmaceutically acceptable solvent.

\* \* \* \* \*